US010781491B2

(12) United States Patent
Coppola et al.

(10) Patent No.: US 10,781,491 B2
(45) Date of Patent: Sep. 22, 2020

(54) MICRORNA SIGNATURE FOR PREDICTING PROGRESSION OF BARRETT'S ESOPHAGUS

(71) Applicant: H. LEE MOFFITT CANCER CENTER AND RESEARCH INSTITUTE, INC., Tampa, FL (US)

(72) Inventors: Domenico Coppola, Tampa, FL (US); Xiaotao Qu, Yardley, PA (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 164 days.

(21) Appl. No.: 15/125,625

(22) PCT Filed: Mar. 16, 2015

(86) PCT No.: PCT/US2015/020759
§ 371 (c)(1),
(2) Date: Sep. 13, 2016

(87) PCT Pub. No.: WO2015/156964
PCT Pub. Date: Oct. 15, 2015

(65) Prior Publication Data
US 2017/0002423 A1  Jan. 5, 2017

Related U.S. Application Data

(60) Provisional application No. 61/953,887, filed on Mar. 16, 2014.

(51) Int. Cl.
C12Q 1/68 (2018.01)
C12Q 1/6886 (2018.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 4,843,155 | A | 6/1989 | Chomczynski | |
|---|---|---|---|---|
| 8,415,102 | B2* | 4/2013 | Geiss | G06F 19/22 435/287.2 |
| 2010/0015607 | A1 | 1/2010 | Geiss et al. | |
| 2010/0047924 | A1 | 2/2010 | Webster et al. | |
| 2010/0261026 | A1 | 10/2010 | Ferree et al. | |
| 2011/0053158 | A1 | 3/2011 | Mambo et al. | |
| 2013/0280720 | A1 | 10/2013 | Christenson et al. | |
| 2014/0162888 | A1 | 6/2014 | Kuslich et al. | |
| 2014/0363469 | A1* | 12/2014 | Meyers | A61K 39/245 424/231.1 |

FOREIGN PATENT DOCUMENTS

| WO | 2007/076129 | 7/2007 |
|---|---|---|
| WO | 2007/076132 | 7/2007 |
| WO | 2008/124847 | 10/2008 |
| WO | 2010/019826 | 2/2010 |

OTHER PUBLICATIONS

De Andres et al. Biotechniques 18:42-44, (1995).
Fassan, et al., "MicroRNA expression profiling in human Barrett's carcinogenesis," International Journal of Cancer, 2010, vol. 129, pp. 1661-1670.
Feber A, et al. MicroRnA expression profiles of esophageal cancer. J Thorac Cardiovasc Surg. 2008;135:255-60.
Griffiths-Jones S, Saini HK, van DS, and Enright AJ. miRBase: tools for microRNA genomics. Nucleic Acids Res 2008; 36(Database issue): D154-D158.
Kan T and Meltzer SJ. MicroRNAs in Barrett's esophagus and esophageal adenocarcinoma. Curr Opinion Pharmacol. 2009;9:727-32.
Kresty LA, Clarke J, Ezell K, Exum A, Howell AB, Guettouche T. MicroRNA alterations in Barrett's esophagus, esophageal adenocarcinoma cell lines following cranberry extract treatment: insights for chemoprevention. J Carcinog 2011;10:34-40.
Li Y, Kong D, Wang Z, and Sarkar FH. Regulation of microRNAs by natural agents: an emerging field in chemoprevention and chemotherapy research. Pharm Res 2010; 27(6): 1027-1041.
Maru DM et al. MicroRNA-196a is a potential marker of progression during Barrett's metaplasia-dysplasia-invasive adenocarcinoma sequence in esophagus. Am J Pathol. 2009. 174(5):1940-8.
Mathé EA et al. MiRNA expression in squamous cell carcinoma nad adenocarcinoma of the esophagus and associations with survival. Clin Cancer Res. 2009;15(19):6192-200.
Revila-Nuin et al., "Predictive Value of MicroRNAs in the Progression of Barrett Esophagus to Adenocarcinoma in a Long-Term Follow-up Study", Annals of Surgery, vol. 257, No. 05, pp. 886-893.
Rupp and Locker, Lab invest. 56:A67, (1987).
Siegel, R., Naishadham, D. and Jemal, A. (2013), Cancer statistics, 2013. CA: A Cancer Journal for Clinicians, 63: 11-30.
Smith CM, et al. MicroRNAs, development of Barrett's esophagus, and progression to esophageal adenocarcinoma. World J Gastroenterol. 2010;16(5):531-7.
Wang et al., "Predicting Neoplastic Progression in Barrett's Esophagus", Annals of Gastroentology and Hepatology, 1(1), pp. 1-18.

(Continued)

*Primary Examiner* — Jehanne S Sitton
(74) *Attorney, Agent, or Firm* — Meunier Carlin & Curfman LLC

(57) ABSTRACT

Biomarkers, methods, assays, and kits are provided for predicting the progression of Barrett esophagus in a subject to esophageal cancer. The method can therefore also be used to select the appropriate treatment for a subject diagnosed with Barrett esophagus. Disclosed are methods for predicting the progression of Barrett esophagus in a subject to esophageal cancer. The method can therefore also be used to select the appropriate treatment for a subject diagnosed with Barrett esophagus. For example, the disclosed biomarkers, methods, assays, and kits can be used to predict the benefit of surgery, laser treatment, radiofrequency ablation, radiation therapy, chemotherapy, or any combination thereof for a subject diagnosed with Barrett esophagus based on whether they are predicted to progress to esophageal cancer.

4 Claims, 2 Drawing Sheets

(56) References Cited

OTHER PUBLICATIONS

Wang Z, et al. Drug Resist Update 2010 13(4-5):109-18.
Wijnhoven BPL, et al. MicroRNA profiling of Barrett's oesophagus and oesophageal adenocarcinoma. Br J Surg. 2010;97:853-61.
Wu X, Ajani JA, Gu J. MicroRNA Expression Signatures during malignant progression fromBarrett's esophagus to esophageal adenocarcinoma. Cancer Prev Res 2013;6:196-205.
Yang H, et al. MicroRNA expression Signatures in Barrett's Esophagus and Esophageal Adenocarcinoma. Clin Cancer Res. 2009;15(18):5744-52.
International Search Report and Written Opinion issued in International Application No. PCT/US2015/020759, dated Jun. 18, 2015.

\* cited by examiner

MICRORNA SIGNATURE FOR PREDICTING PROGRESSION OF BARRETT'S ESOPHAGUS

CROSS-REFERENCE TO RELATED APPLICATIONS

This application claims benefit of U.S. Provisional Application No. 61/953,887, filed Mar. 16, 2014, which is hereby incorporated herein by reference in its entirety.

BACKGROUND

The overall survival of patients diagnosed with esophageal cancer is the worst among human malignancies. In 2013 there were 17,990 new cases diagnosed in the U.S. and 15,210 deaths from the disease. Chronic gastroesophageal reflux disease, which leads to Barrett esophagus, is the most common risk factor for development of esophageal adenocarcinoma [Feber A, et al. J Thorac Cardiovasc Surg. 2008 135:255-60]. Progression of Barrett esophagus to adenocarcinoma occurs via a stepwise progression from intestinal metaplasia to low-grade dysplasia to high-grade dysplasia to adenocarcinoma [Feber A, et al. J Thorac Cardiovasc Surg. 2008 135:255-60]. Currently, monitoring the progression or status of an individual's Barrett esophagus is accomplished by periodic gastroesophagoduodenoscopy (EGD) with biopsies. This procedure is costly, time-consuming, uncomfortable to patients, and limited by sampling error which is compounded by the fact that the distribution of metaplasia/dysplasia/carcinoma is heterogenous within any given patch of Barrett's esophagus. The discovery of effective tools for predicting which cases of dysplasia are likely to progress to adenocarcinoma would help prevent over- or under-treatment.

SUMMARY

Biomarkers, methods, assays, and kits are provided for predicting the progression of Barrett esophagus in a subject to esophageal cancer. The method can therefore also be used to select the appropriate treatment for a subject diagnosed with Barrett esophagus. For example, the disclosed biomarkers, methods, assays, and kits can be used to predict the benefit of surgery, laser treatment, photodynamic therapy, radiofrequency ablation, radiation therapy, chemotherapy, or any combination thereof for a subject diagnosed with Barrett esophagus based on whether they are predicted to progress to esophageal cancer. In particular, the assays and kits can contain primers, probes, or binding agents for detecting expression at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of miRNA selected from the group consisting of hsa-miR-143-3p, hsa-miR-145-5p, hsa-miR-150-5p, hsa-miR-199a-3p+/hsa-miR-199b-3p, hsa-miR-126-3p, hsa-miR-142-3p, hsa-miR-4516, hsa-miR-125b-5p, hsa-miR-26a-5p, hsa-let-7e-5p, hsa-miR-26b-5p, hsa-miR-130a-3p, hsa-miR-199b-5p, hsa-miR-100-5p, hsa-miR-29b-3p, hsa-miR-30a-5p, hsa-miR-30b-5p, hsa-miR-199a-5p, hsa-miR-223-3p, hsa-miR-342-3p, hsa-miR-361-5p, hsa-miR-1915-3p, hsa-miR-497-5p, hsa-miR-34a-5p, hsa-miR-125a-5p, hsa-miR-195-5p, hsa-miR-374b-5p, hsa-miR-376a-3p, hsa-miR-423-5p, hsa-miR-720, hsa-miR-132-3p, hsa-miR-4508, and hsa-miR-3195.

The disclosed method can involve obtaining a biological sample (e.g., biopsy) from the subject and determining levels of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the disclosed miRNA in the biological sample. In some embodiments, elevated levels of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 of the disclosed miRNA compared to control values is an indication that the subject is likely the Barrett esophagus is likely going to progress to dysplasia. In some embodiments, the method involves comparing the miRNA expression levels to control values to produce an miRNA profile. The method can then comprise calculating a risk score from the gene profile. For example, in some embodiments, a high risk score is an indication that the subject is likely to develop esophageal cancer.

In particular, the biological sample can be RNA derived from formalin fixed paraffin embedded tissue. These slides are routinely collected for histology and can be used as source of RNA to measure miRNA expression levels.

If the subject has normal or low miRNA expression levels and/or a low risk score that they will progress to low grade dysplasia, the method can involve reducing the frequency of endoscopy monitory, e.g., every 1, 2, 3, 4, or 5 years. However, if the subject has elevated miRNA expression levels and/or a high risk score that they will progress to low grade dysplasia, the method can further involve treating the subject with surgery, laser treatment, radiofrequency ablation, chemotherapy, or any combination thereof. The method can further involve monitoring the subject for progression by endoscopy more frequently, e.g., every six months to a year.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
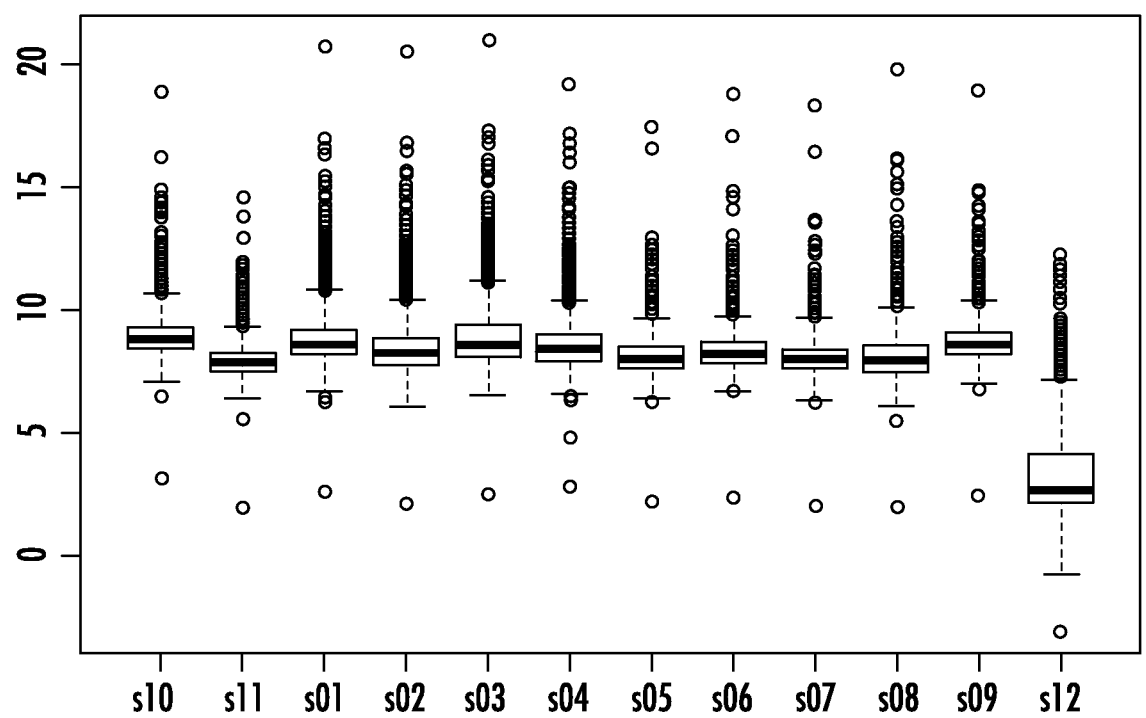
FIG. 1 is a box plot showing 33 out of 800 miRNA tested in 11 samples (disregard S12) have similar distribution after normalization.

Barrett esophagus, sometimes called Barrett syndrome or columnar epithelium lined lower oesophagus (CELLO), refers to an abnormal change (metaplasia) in the cells of the lower portion of the esophagus. This involves the replacement of normal stratified squamous epithelium lining of the esophagus with simple columnar epithelium with goblet cells. The main cause of Barrett esophagus is thought to be an adaptation to chronic acid exposure from reflux esophagitis. Barrett esophagus is found in 5-15% of patients who seek medical care for heartburn (gastroesophageal reflux disease, GERD), although a large subgroup of patients with Barrett esophagus do not have symptoms. It is considered to be a premalignant condition because it is associated with an increased risk of esophageal cancer (more specifically, adenocarcinoma) of about 0.5% per patient-year. The cells of Barrett esophagus, after biopsy by esophagogastroduodenoscopy, are classified into four general categories: non-dysplastic, low-grade dysplasia, high-grade dysplasia, and frank carcinoma. High-grade dysplasia and early stages of adenocarcinoma can be treated by endoscopic resection and new endoscopic therapies such as radiofrequency ablation; whereas advanced stages (submucosal) are generally advised to undergo surgical treatment. Non-dysplastic and low-grade patients are generally advised to undergo annual observation with endoscopy, with radiofrequency ablation as a therapeutic option. In high-grade dysplasia, the risk of developing cancer might be at 10% per patient-year or greater. After the initial diagnosis of Barrett esophagus is rendered, affected persons undergo annual surveillance to detect development of dysplasia.

Treatment options for high-grade dysplasia include surgical removal of the esophagus (esophagectomy) or endoscopic treatments such as endoscopic mucosal resection or ablation (destruction). Balloon-based radiofrequency ablation has an efficacy of 80-90% or greater with respect to complete clearance of Barrett's esophagus and dysplasia with durability up to 5 years and a favorable safety profile. Laser treatment can be used in severe dysplasia, while overt malignancy may require surgery, radiation therapy, or systemic chemotherapy. Additionally, a recent 5-year random-controlled trial has shown that photodynamic therapy using photofrin is statistically more effective in eliminating dysplastic growth areas than sole use of a proton pump inhibitor. Endoscopic mucosal resection (EMR) has also been evaluated as a management technique. Additionally, an operation known as a Nissen fundoplication can reduce the reflux of acid from the stomach into the esophagus. In a variety of studies, non-steroidal anti-inflammatory drugs (NSAIDS), like aspirin, have shown evidence of preventing esophageal cancer in Barrett esophagus patients.

Disclosed are methods for predicting the progression of Barrett esophagus in a subject to esophageal cancer. The method can therefore also be used to select the appropriate treatment for a subject diagnosed with Barrett esophagus. For example, the disclosed biomarkers, methods, assays, and kits can be used to predict the benefit of surgery, laser treatment, radiofrequency ablation, radiation therapy, chemotherapy, or any combination thereof for a subject diagnosed with Barrett esophagus based on whether they are predicted to progress to esophageal cancer. The assays and kits can contain primers, probes, or binding agents for detecting expression at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 miRNA selected from the group consisting of hsa-miR-143-3p, hsa-miR-145-5p, hsa-miR-150-5p, hsa-miR-199a-3p+/hsa-miR-199b-3p, hsa-miR-126-3p, hsa-miR-142-3p, hsa-miR-4516, hsa-miR-125b-5p, hsa-miR-26a-5p, hsa-let-7e-5p, hsa-miR-26b-5p, hsa-miR-130a-3p, hsa-miR-199b-5p, hsa-miR-100-5p, hsa-miR-29b-3p, hsa-miR-30a-5p, hsa-miR-30b-5p, hsa-miR-199a-5p, hsa-miR-223-3p, hsa-miR-342-3p, hsa-miR-361-5p, hsa-miR-1915-3p, hsa-miR-497-5p, hsa-miR-34a-5p, hsa-miR-125a-5p, hsa-miR-195-5p, hsa-miR-374b-5p, hsa-miR-376a-3p, hsa-miR-423-5p, hsa-miR-720, hsa-miR-132-3p, hsa-miR-4508, and hsa-miR-3195.

The disclosed method can involve obtaining a biological sample from the subject and determining levels of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 disclosed miRNA in the biological sample. In some embodiments, elevated levels of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33 disclosed miRNA compared to control values is an indication that the subject is likely the Barrett esophagus is likely going to progress to dysplasia. In some embodiments, the method involves comparing the miRNA expression levels to control values to produce an miRNA profile. The method can then comprise calculating a risk score from the gene profile. For example, in some embodiments, a high risk score is an indication that the subject is likely to develop esophageal cancer. Routine statistical methods can be used to develop calculations for risk scores, e.g., using the miRNA values shown in Table 1 or Table 2, or a subset thereof.

The biological sample may comprise any clinically relevant tissue sample, such as a tissue biopsy. The sample may be taken from a human, or, in a veterinary context, from non-human animals such as ruminants, horses, swine or sheep, or from domestic companion animals such as felines and canines. Additionally, the samples may be from frozen or archived formalin-fixed, paraffin-embedded (FFPE) tissue samples.

General methods for RNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker, Lab Invest. 56:A67, (1987); and De Andres et al. Biotechniques 18:42-44, (1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MASTERPURE™ Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). Total RNA from FFPE can be isolated, for example, using High Pure FFPE RNA Microkit, Cat No. 04823125001 (Roche Applied Science, Indianapolis, Ind.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155).

Gene Expression Assays

Methods of "determining miRNA expression levels" include methods that quantify levels of miRNA. A measured expression level may be expressed as any quantitative value, for example, a fold-change in expression, up or down, relative to a control miRNA or relative to the same miRNA in another sample, or a log ratio of expression, or any visual representation thereof, such as, for example, a "heatmap" where a color intensity is representative of the amount of gene expression detected. Exemplary methods for detecting the level of expression of a miRNA include, but are not limited to, Northern blotting, dot or slot blots, reporter gene matrix, nuclease protection, RT-PCR, microarray profiling, differential display, 2D gel electrophoresis, SELDI-TOF, ICAT, enzyme assay, antibody assay, and MNAzyme-based detection methods. Optionally a miRNA whose level of expression is to be detected may be amplified, for example by methods that may include one or more of: polymerase chain reaction (PCR), strand displacement amplification (SDA), loop-mediated isothermal amplification (LAMP), rolling circle amplification (RCA), transcription-mediated amplification (TMA), self-sustained sequence replication (3SR), nucleic acid sequence based amplification (NASBA), or reverse transcription polymerase chain reaction (RT-PCR).

A number of suitable high throughput formats exist for evaluating expression patterns and profiles of the disclosed biomarkers. Numerous technological platforms for performing high throughput expression analysis are known. Generally, such methods involve a logical or physical array of the subject samples, the biomarkers, or both. Common array formats include both liquid and solid phase arrays. For example, assays employing liquid phase arrays, e.g., for hybridization of nucleic acids, binding of antibodies or other receptors to ligand, etc., can be performed in multiwell or microtiter plates. Microtiter plates with 96, 384 or 1536 wells are widely available, and even higher numbers of wells, e.g., 3456 and 9600 can be used. In general, the choice of microtiter plates is determined by the methods and equipment, e.g., robotic handling and loading systems, used for sample preparation and analysis. Exemplary systems include, e.g., xMAP® technology from Luminex (Austin, Tex.), the SECTOR® Imager with MULTI-ARRAY® and MULTI-SPOT® technologies from Meso Scale Discovery (Gaithersburg, Md.), the ORCA™ system from Beckman-Coulter, Inc. (Fullerton, Calif.) and the ZYMATE™ systems from Zymark Corporation (Hopkinton, Mass.), miRCURY LNA™ microRNA Arrays (Exiqon, Woburn, Mass.).

Alternatively, a variety of solid phase arrays can favorably be employed to determine expression patterns in the context of the disclosed methods, assays and kits. Exemplary formats include membrane or filter arrays (e.g., nitrocellulose, nylon), pin arrays, and bead arrays (e.g., in a liquid "slurry"). Typically, probes corresponding to nucleic acid or protein reagents that specifically interact with (e.g., hybridize to or bind to) an expression product corresponding to a member of the candidate library, are immobilized, for example by direct or indirect cross-linking, to the solid support. Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In one embodiment, the array is a "chip" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Microarray expression may be detected by scanning the microarray with a variety of laser or CCD-based scanners, and extracting features with numerous software packages, for example, IMAGENE™ (Biodiscovery), Feature Extraction Software (Agilent), SCANLYZE™ (Stanford Univ., Stanford, Calif.), GENEPIX™ (Axon Instruments).

In some embodiments, the nCounter® Analysis system (Nanostring Technologies, Seattle, Wash.) is used to detect intrinsic gene expression. This system is described in International Patent Application Publication No. WO 08/124,847 and U.S. Pat. No. 8,415,102, which are each incorporated herein by reference in their entireties for the teaching of this system. The basis of the nCounter® Analysis system is the unique code assigned to each nucleic acid target to be assayed. The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system.

Specific reporter and capture probes are synthesized for each target. Briefly, sequence-specific DNA oligonucleotide probes are attached to code-specific reporter molecules. Preferably, each sequence specific reporter probe comprises a target specific sequence capable of hybridizing to no more than one miRNA of Table 2 and optionally comprises at least two, at least three, or at least four label attachment regions, said attachment regions comprising one or more label monomers that emit light. Capture probes are made by ligating a second sequence-specific DNA oligonucleotide for each target to a universal oligonucleotide containing biotin. Reporter and capture probes are all pooled into a single hybridization mixture, the "probe library". Preferably, the probe library comprises a probe pair (a capture probe and reporter) for each of the miRNA in Table 2.

The relative abundance of each target is measured in a single multiplexed hybridization reaction. The method comprises contacting a biological sample with a probe library, the library comprising a probe pair for the miRNA in Table 2, such that the presence of the target in the sample creates a probe pair-target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies).

Purified reactions are deposited by the Prep Station into individual flow cells of a sample cartridge, bound to a streptavidin-coated surface via the capture probe, electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. Data is output in simple spreadsheet format listing the number of counts per target, per sample.

This system can be used along with nanoreporters. Additional disclosure regarding nanoreporters can be found in International Publication No. WO 07/076,129 and WO 07/076,132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No. 2010/0047924, incorporated herein by reference in its entirety.

Calculation of Risk Score

From the disclosed miRNA expression values, a dataset can be generated and inputted into an analytical classification process that uses the data to classify the biological sample with a risk score.

The data may be obtained via any technique that results in an individual receiving data associated with a sample. For example, an individual may obtain the dataset by generating the dataset himself by methods known to those in the art. Alternatively, the dataset may be obtained by receiving a dataset or one or more data values from another individual or entity. For example, a laboratory professional may generate certain data values while another individual, such as a medical professional, may input all or part of the dataset into an analytic process to generate the result.

Prior to input into the analytical process, the data in each dataset can be collected by measuring the values for each marker, usually in duplicate or triplicate or in multiple replicates. The data may be manipulated, for example raw data may be transformed using standard curves, and the average of replicate measurements used to calculate the average and standard deviation for each patient. These values may be transformed before being used in the models.

For example, it is often useful to pre-process miRNA expression data, for example, by addressing missing data, translation, scaling, normalization, weighting, etc. Multivariate projection methods, such as principal component analysis (PCA) and partial least squares analysis (PLS), are so-called scaling sensitive methods. By using prior knowledge and experience about the type of data studied, the quality of the data prior to multivariate modeling can be enhanced by scaling and/or weighting. Adequate scaling and/or weighting can reveal important and interesting variation hidden within the data, and therefore make subsequent multivariate modeling more efficient. Scaling and weighting may be used to place the data in the correct metric, based on knowledge and experience of the studied system, and therefore reveal patterns already inherently present in the data.

If possible, missing data, for example gaps in column values, should be avoided. However, if necessary, such missing data may replaced or "filled" with, for example, the mean value of a column ("mean fill"); a random value ("random fill"); or a value based on a principal component analysis ("principal component fill").

"Translation" of the descriptor coordinate axes can be useful. Examples of such translation include normalization and mean centering. "Normalization" may be used to remove sample-to-sample variation. Some commonly used methods for calculating normalization factor include: (i) global normalization that uses all genes on the array; (ii) housekeeping genes normalization that uses constantly expressed housekeeping/invariant genes; and (iii) internal controls normalization that uses known amount of exogenous control genes added during hybridization. In some embodiments, the intrinsic genes disclosed herein can be normalized to control housekeeping genes. It will be understood by one of skill in the art that the methods disclosed herein are not bound by normalization to any particular housekeeping genes, and that any suitable housekeeping gene(s) known in the art can be used.

Many normalization approaches are possible, and they can often be applied at any of several points in the analysis. In one embodiment, data is normalized using the LOWESS method, which is a global locally weighted scatter plot smoothing normalization function. In another embodiment, data is normalized to the geometric mean of set of multiple housekeeping genes.

"Mean centering" may also be used to simplify interpretation. Usually, for each descriptor, the average value of that descriptor for all samples is subtracted. In this way, the mean of a descriptor coincides with the origin, and all descriptors are "centered" at zero. In "unit variance scaling," data can be scaled to equal variance. Usually, the value of each descriptor is scaled by 1/StDev, where StDev is the standard deviation for that descriptor for all samples. "Pareto scaling" is, in some sense, intermediate between mean centering and unit variance scaling. In pareto scaling, the value of each descriptor is scaled by 1/sqrt(StDev), where StDev is the standard deviation for that descriptor for all samples. In this way, each descriptor has a variance numerically equal to its initial standard deviation. The pareto scaling may be performed, for example, on raw data or mean centered data.

"Logarithmic scaling" may be used to assist interpretation when data have a positive skew and/or when data spans a large range, e.g., several orders of magnitude. Usually, for each descriptor, the value is replaced by the logarithm of that value. In "equal range scaling," each descriptor is divided by the range of that descriptor for all samples. In this way, all descriptors have the same range, that is, 1. However, this method is sensitive to presence of outlier points. In "autoscaling," each data vector is mean centered and unit variance scaled. This technique is a very useful because each descriptor is then weighted equally, and large and small values are treated with equal emphasis. This can be important for genes expressed at very low, but still detectable, levels.

The methods described herein may be implemented and/or the results recorded using any device capable of implementing the methods and/or recording the results. Examples of devices that may be used include but are not limited to electronic computational devices, including computers of all types. When the methods described herein are implemented and/or recorded in a computer, the computer program that may be used to configure the computer to carry out the steps of the methods may be contained in any computer readable medium capable of containing the computer program. Examples of computer readable medium that may be used include but are not limited to diskettes, CD-ROMs, DVDs, ROM, RAM, and other memory and computer storage devices. The computer program that may be used to configure the computer to carry out the steps of the methods and/or record the results may also be provided over an electronic network, for example, over the internet, an intranet, or other network.

This data can then be input into the analytical process with defined parameter. The analytic classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm.

Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2 or more. In some embodiments, it is 3 or more, 4 or more, 10 or more, or between 10 and 74. Depending on the degree of certainty sought, however, the number of features used in an analytical process can be more or less, but in all cases is at least 2. In one embodiment, the number of features that may be used by an analytical process to classify a test subject is optimized to allow a classification of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. Such algorithms classify complex spectra from biological materials to distinguish subjects as normal or as possessing biomarker levels characteristic of a particular disease state. In other embodiments, a data analysis algorithm of the disclosure comprises ANOVA and nonparametric equivalents, linear discriminant analysis, logistic regression analysis, nearest neighbor classifier analysis, neural networks, principal component analysis, quadratic discriminant analysis, regression classifiers and support vector machines. While such algorithms may be used to construct an analytical process and/or increase the speed and efficiency of the application of the analytical process and to avoid investigator bias, one of ordinary skill in the art will realize that computer-based algorithms are not required to carry out the methods of the present disclosure.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

EXAMPLES

Example 1

Nanostring Analysis of miRNA Profiles in Patients with Barrett's Esophagus without Progression to Dysplasia as Compared to Those with Barrett's Esophagus Progressed to Dysplasia and Carcinoma Introduction Recent gene expression studies identified a set of small number of genes that are differentially expressed in esophageal cancer but no information is available for assessing their impact on disease prognosis. In recent years there has been a dramatic increase in the discovery of microRNAs (miRNAs) that are associated with cancer aggressiveness. The miRNAs are naturally occurring small non-coding molecules found in humans that regulate gene expression and consequently have a potential functional role in a wide array of cellular processes, including differentiation, proliferation, and apoptosis [Li Y, et al. Pharm Res 2010 27(6): 1027-1041; Wang Z, et al. Drug Resist Updat 2010 13(4-5):109-18].

To date, less than 20 publications in this field are available and all investigated the miRNA expression profiles of Barrett's esophagus (using actual tissue from the esophagus), comparing normal squamous mucosa or normal gastric cardiac mucosa with Barrett's esophagus (intestinal metaplasia without dysplasia), low-grade dysplasia, high-grade dysplasia, and adenocarcinoma in paired tissue [Feber A, et al. J Thorac Cardiovasc Surg. 2008 135:255-60; Smith C M, et al. World J Gastroenterol. 2010 16(5):531-7; Kan T and Meltzer S J. Curr Opinion Pharmacol. 2009 9:727-32; Maru D M, et al. Am J Pathol. 2009 174(5):1940-8; Mathé E A, et al. Clin Cancer Res. 2009 15(19):6192-200; Wijnhoven B P L, et al. Br J Surg. 2010 97:853-61; Yang H, et al. Clin Cancer Res. 2009 15(18):5744-52; Wu X, et al. Cancer Prev Res 2013 6:196-205; Kresty L A, et al. J Carcinog 2011 10:34-40]. Some of these studies show that expression of some miRNAs is consistently altered with this progression and that the histology of a given tissue can be reliably predicted based on miRNA expression profile alone most of the time. A criticism that could be raised to all of these studies is that the endoscopic and gross appearance of BE with dysplasia or early carcinoma is indistinguishable from Barrett esophagus without dysplasia. Different endoscopic protocols were designed to obtain the appropriate number of biopsies and to minimize the sampling issue. However, the possibility that a patient classified as having Barrett's esophagus without dysplasia may harbor an unrecognized focus of dysplasia/carcinoma cannot be completely excluded.

The disclosed study used samples from patients that have had Barrett's esophagus without progression to dysplasia and carcinoma for >7 years. These patients were followed with periodic endoscopies as recommended by the American Gastroenterological Association guidelines. These samples are compared to samples from patients with Barrett's esophagus that later progressed to dysplasia/carcinoma. Nanostring technology is used to identify miRNAs that select patients with Barrett's esophagus prone to progress to dysplasia and carcinoma from those harboring the type of Barrett's esophagus that has a less likelihood to progress to dysplasia/carcinoma. The use of these miRNAs allow closer follow up of those patients at high risk to develop Barrett's dysplasia/cancer and early detection of progression. This is of extreme importance as fully established Barrett's carcinomas have a dismal prognosis regardless of treatment.

Nanostring technology is used to identify miRNAs able to discriminate between patients with Barrett's esophagus prone to progress to dysplasia and carcinoma from those harboring the type of Barrett's esophagus that has a less likelihood to progress to dysplasia/carcinoma. The discovered miRNAs can be used to test the biopsy tissues for patient stratification.

Materials & Methods

Nanostring miRNA analysis was performed on existing formalin-fixed paraffin-embedded tissue blocks from patients with Barrett's esophagus which later progressed to low-grade dysplasia, high-grade dysplasia, and/or esophageal adenocarcinoma (n=5) and from patients with Barrett's esophagus which remained stable without progression to dysplasia and carcinoma for >7 years (n=4).

After macrodissection, RNA was extracted from formalin-fixed, paraffin-embedded tissue using the Qiagen miRNEasy FFPE kit to isolate RNA molecules larger than 14 nucleotides. Briefly, the sample was de-paraffinized and de-crosslinked using Qiagen Deparaffinaization Solution, followed by DNase digestion and Proteinase K treatment. Finally, the samples were purified by a Qiagen RNEasy MinElute column and RNA quality was evaluated on an Agilent High BioAnalyzer RNA 6000 Nano Kit. 100 ng of total RNA was processed and hybridized to the NanoString nCounter miRNA Expression Assay according to the manufacturer's protocol, miRNA expression values were normalized to the geometric mean of the 100 highest expressing probes using the nSolver data analysis software.

Results.

The results for all 800 miRNA tested are shown in Table 1, miRNA that differentially expressed with statistical significance among the 2 subset were selected using the following criteria.

1. T-test p-value<0.05
2. Log ration fold change>=1

33 out of 800 miRNA were selected, and they are all up-regulated in the group of Barrett that progressed to dysplasia/carcinoma (Table 2). The FDR was calculated. As shown in FIG. 1, a box plot of the 11 samples (disregard S12) have similar distribution after normalization, demonstrating that the data is correct.

Figure 2:
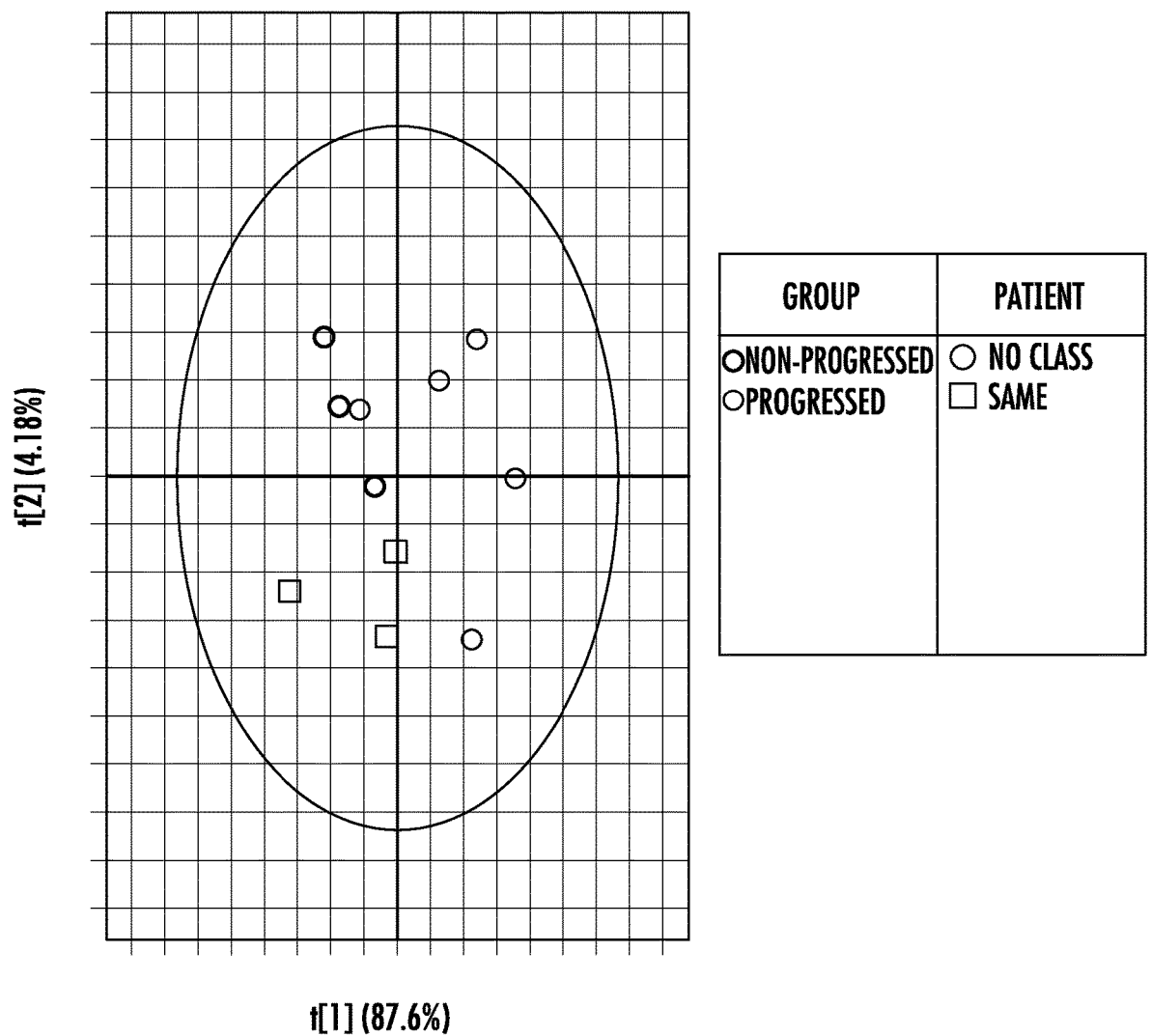
FIG. 2 is a plot showing results of PCA analysis of eleven Barrett's Esophagus (BE) patients using 33 selected miRNAs. Blue—Denotes patients that do not progress to cancer (N=5), Green—Denotes patients that do progress to cancer (N=4).

The PCA analysis using the 33 selected miRNAs shows that the first component accounts for almost 90% of variation, which is very good (FIG. 2). However, one of the samples from the group of Barrett that progressed (green circle) overlaps with the samples of the Barrett that did not progress (blue circles). Review of the pathology slides for this sample showed that low grade dysplasia was diagnosed in error by the pathologist.

CONCLUSION

The importance of identifying miRNA that can discriminate between Barrett patients that are likely to progress to dysplasia and cancer and those that will not progress will impact the current management of Barrett's patients allowing for a more rigid follow up of patient at risk of developing dysplasia and cancer. In addition, identification of these patients may offer opportunity for early intervention.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

TABLE 1

| mirna | Results from 800 miRNA tested | | | | | | | | | | | P-value (t-test) | Q-value (FDR) | log2 fold change* |
|---|---|---|---|---|---|---|---|---|---|---|---|---|---|---|
| | s01 | s02 | s03 | s04 | s05 | s06 | s07 | s08 | s09 | s10 | s11 | | | |
| hsa-miR-363-3p | 6.2018 | 7.0147 | 7.405 | 2.8094 | 2.2265 | 6.7859 | 7.3656 | 7.3211 | 9.5605 | 8.73 | 8.7152 | 0.051 | 0.8772 | -2.9482 |
| hsa-miR-1283 | 10.385 | 8.7371 | 8.9575 | 2.8094 | 2.2265 | 9.2807 | 10.2677 | 2 | 9.3957 | 9.9524 | 9.1402 | 0.4442 | 0.9763 | -1.7163 |
| hsa-miR-4443 | 9.8552 | 9.9843 | 10.1705 | 4.8099 | 9.0219 | 9.4245 | 9.2136 | 9.6574 | 10.7499 | 10.3834 | 9.8792 | 0.3365 | 0.9689 | -1.1163 |
| hsa-miR-532-5p | 8.6612 | 2.1077 | 9.3183 | 8.643 | 7.928 | 8.2091 | 7.825 | 7.3568 | 8.7269 | 9.2743 | 7.7677 | 0.5566 | 0.981 | -0.8617 |
| hsa-miR-203 | 11.5357 | 13.6401 | 11.939 | 11.9213 | 9.6538 | 14.5673 | 12.3151 | 14.9032 | 11.0303 | 11.2272 | 9.0688 | 0.6976 | 0.9848 | -0.4474 |
| hsa-miR-205-5p | 10.6055 | 13.7628 | 12.2003 | 12.4966 | 8.2499 | 14.805 | 13.5672 | 16.0276 | 9.0114 | 9.8315 | 8.0264 | 0.8086 | 0.9868 | -0.4152 |
| hsa-miR-1273f | 6.9388 | 6.1077 | 7.0217 | 6.5106 | 6.6869 | 6.85 | 6.7442 | 6.8066 | 7.6115 | 7.6686 | 6.4838 | 0.1826 | 0.9442 | -0.3743 |
| hsa-miR-2277-5p | 8.3717 | 7.8357 | 8.1705 | 7.9394 | 7.5129 | 8.0544 | 7.9744 | 8.0436 | 8.8509 | 8.9524 | 8.0264 | 0.1725 | 0.9411 | -0.351 |
| hsa-miR-636 | 7.3172 | 7.062 | 6.4981 | 7.5106 | 7.1817 | 7.684 | 6.7986 | 7.4586 | 7.7635 | 8.0519 | 6.9603 | 0.2279 | 0.9548 | -0.3389 |
| hsa-miR-607 | 8.0091 | 7.8082 | 8.1985 | 8.3647 | 8.0854 | 8.5932 | 8.1311 | 8.303 | 8.7083 | 8.8999 | 7.9145 | 0.0999 | 0.9025 | -0.3318 |
| hsa-miR-598 | 10.0844 | 9.7516 | 10.1128 | 9.3647 | 9.4563 | 9.5744 | 9.9744 | 9.8129 | 10.7725 | 10.6288 | 9.7351 | 0.2303 | 0.9552 | -0.3291 |
| hsa-miR-539-5p | 7.6168 | 6.8627 | 7.5425 | 6.6175 | 7.2718 | 7.7859 | 7.3291 | 7.1285 | 7.8678 | 7.8455 | 7.0478 | 0.2329 | 0.9557 | -0.3185 |
| hsa-miR-449b-5p | 7.9388 | 7.3557 | 7.405 | 7.8101 | 7.4754 | 7.8501 | 7.7716 | 7.2471 | 7.7635 | 8.6996 | 8.1302 | 0.2075 | 0.9505 | -0.3133 |
| hsa-miR-520g | 7.7867 | 7.3557 | 7.405 | 7.9394 | 7.2275 | 7.8183 | 7.1729 | 7.1691 | 8.2489 | 8.6369 | 7.2823 | 0.2915 | 0.9643 | -0.3125 |
| hsa-miR-620 | 7.7042 | 7.3932 | 7.8201 | 7.3951 | 7.0854 | 7.9412 | 7.5983 | 7.3568 | 7.8678 | 8.3545 | 7.6327 | 0.1376 | 0.9272 | -0.3123 |
| hsa-miR-675-5p | 7.9388 | 7.1078 | 7.0217 | 7.9394 | 6.9824 | 7.8501 | 7.2531 | 7.5537 | 7.901 | 8.315 | 7.3526 | 0.2982 | 0.9651 | -0.3062 |
| hsa-miR-544b | 8.0091 | 7.6313 | 7.405 | 7.7171 | 7.9554 | 7.9703 | 7.7161 | 7.6139 | 8.5076 | 8.467 | 7.9145 | 0.1635 | 0.9381 | -0.288 |
| hsa-miR-891b | 8.6168 | 8.4476 | 8.7835 | 8.302 | 8.5129 | 8.7859 | 8.4699 | 8.7134 | 9.287 | 9.1894 | 8.4681 | 0.1208 | 0.9179 | -0.2864 |
| hsa-miR-766-3p | 8.4497 | 7.3932 | 8.0527 | 7.9801 | 7.0349 | 7.8501 | 7.6584 | 7.9764 | 8.486 | 8.5373 | 7.8672 | 0.3708 | 0.9717 | -0.2805 |
| hsa-miR-1205 | 8.3447 | 7.7225 | 8.142 | 8.058 | 7.6538 | 8.0544 | 8.3291 | 7.8321 | 8.529 | 8.6996 | 8.0896 | 0.1776 | 0.9427 | -0.2714 |
| hsa-miR-378h | 7.6168 | 7.5996 | 8.1128 | 8.1321 | 7.7193 | 8.0544 | 7.9744 | 7.4586 | 8.2995 | 8.7889 | 8.0264 | 0.2501 | 0.9586 | -0.2642 |
| hsa-miR-1254 | 8.3447 | 7.8626 | 8.226 | 7.9394 | 7.437 | 8.0814 | 8.2531 | 7.9299 | 8.1695 | 9.0277 | 7.8429 | 0.305 | 0.9658 | -0.2555 |
| hsa-miR-576-5p | 8.2335 | 7.6623 | 8.3561 | 8.0956 | 7.6538 | 7.6484 | 8.066 | 8.0436 | 8.9173 | 8.873 | 7.9827 | 0.3477 | 0.9699 | -0.2553 |
| hsa-miR-761 | 9.2607 | 8.9781 | 9.1705 | 8.8545 | 8.751 | 9.0269 | 8.8119 | 8.9534 | 9.7834 | 9.8729 | 9.0478 | 0.2762 | 0.9624 | -0.2461 |
| hsa-miR-4521 | 8.0762 | 7.7225 | 8.0216 | 8.058 | 7.315 | 8.2807 | 7.8766 | 7.9299 | 8.3242 | 8.145 | 7.9376 | 0.1905 | 0.9464 | -0.2437 |
| hsa-miR-767-5p | 7.7042 | 7.3932 | 7.668 | 7.0581 | 7.2275 | 7.4557 | 7.5355 | 7.2846 | 7.7934 | 8.1894 | 7.5149 | 0.2259 | 0.9544 | -0.2421 |
| hsa-miR-1299 | 8.3172 | 8.1301 | 8.5205 | 8.4826 | 8.2048 | 8.7188 | 8.2725 | 8.2086 | 8.7269 | 9.3738 | 8.11 | 0.294 | 0.9646 | -0.2374 |
| hsa-miR-3123 | 8.3981 | 8.085 | 8.331 | 8.2025 | 7.928 | 8.5163 | 8.4187 | 8.339 | 8.3484 | 8.8455 | 8.0688 | 0.1155 | 0.9145 | -0.2339 |
| hsa-miR-556-3p | 7.3172 | 7.1078 | 7.3054 | 7.2696 | 7.1817 | 7.4557 | 7.2136 | 6.906 | 7.9334 | 8.1894 | 7.0896 | 0.3209 | 0.9674 | -0.2283 |
| hsa-miR-1277-3p | 9.0431 | 9.1078 | 9.2663 | 9.2364 | 8.2499 | 9.3926 | 9.1522 | 8.9417 | 9.6989 | 9.8865 | 9.1402 | 0.2001 | 0.9488 | -0.2234 |
| hsa-miR-548x-3p | 8.7461 | 8.8891 | 8.8379 | 8.9187 | 8.7194 | 9.0544 | 8.7161 | 8.5841 | 9.3484 | 9.7149 | 8.8429 | 0.2636 | 0.9607 | -0.2213 |
| hsa-miR-548ac | 6.7043 | 6.5 | 7.6274 | 7.7171 | 6.6869 | 7.1845 | 6.9017 | 7.1285 | 7.8338 | 7.8455 | 6.7152 | 0.5128 | 0.9794 | -0.2211 |
| hsa-miR-548al | 10.3583 | 9.8289 | 10.0906 | 10.0098 | 9.7973 | 10.0679 | 9.9979 | 10.0215 | 10.8035 | 10.5201 | 10.0156 | 0.2333 | 0.9558 | -0.2208 |
| hsa-miR-1183 | 9.7867 | 9.2777 | 9.746 | 9.0581 | 9.3568 | 9.2923 | 9.3835 | 9.2846 | 10.1489 | 10.2948 | 9.5897 | 0.3634 | 0.9711 | -0.2206 |
| hsa-miR-671-3p | 7.4748 | 7.1952 | 7.1985 | 7.2696 | 7.1817 | 7.4557 | 6.9017 | 7.3915 | 7.6115 | 8.2743 | 7.2456 | 0.3104 | 0.9664 | -0.2161 |
| hsa-miR-548w | 8.3172 | 7.9657 | 8.331 | 8.2696 | 8.2275 | 8.2807 | 7.9979 | 8.339 | 8.529 | 9.0277 | 8.4522 | 0.2057 | 0.9501 | -0.2155 |
| hsa-miR-2053 | 9.0262 | 8.7943 | 8.6879 | 7.7409 | 8.5313 | 9.1078 | 8.8251 | 8.3742 | 9.4639 | 9.6208 | 8.436 | 0.3771 | 0.9722 | -0.2152 |
| hsa-miR-147b | 8.6829 | 8.2976 | 8.3561 | 8.1321 | 8.2499 | 8.4139 | 8.1934 | 8.339 | 8.7991 | 9.2535 | 8.3526 | 0.2832 | 0.9633 | -0.2149 |
| hsa-miR-508-5p | 7.9388 | 8.0619 | 8.253 | 8.2025 | 8.0854 | 8.3265 | 7.7986 | 8.0215 | 8.5913 | 9.0519 | 8.1302 | 0.3117 | 0.9665 | -0.2117 |
| hsa-miR-380-3p | 7.9388 | 7.5996 | 8.0831 | 8.4248 | 7.5494 | 8.4964 | 7.7161 | 7.6716 | 8.4188 | 8.4304 | 8.0264 | 0.3757 | 0.9721 | -0.2075 |
| hsa-miR-610 | 8.7043 | 8.3746 | 8.4754 | 7.8101 | 8.336 | 8.6663 | 8.2335 | 8.3915 | 8.3242 | 9.003 | 7.8429 | 0.4272 | 0.9753 | -0.2065 |
| hsa-miR-23c | 8.1404 | 7.6313 | 7.8201 | 7.9394 | 6.9279 | 7.684 | 7.5983 | 7.6996 | 9.5229 | 8.5026 | 7.6041 | 0.4643 | 0.9773 | -0.2044 |
| hsa-miR-671-5p | 9.1087 | 8.9406 | 9.2396 | 8.6681 | 8.6537 | 8.8183 | 8.9263 | 8.8065 | 9.5184 | 9.6686 | 9.0047 | 0.3199 | 0.9673 | -0.2034 |
| hsa-miR-325 | 9.0762 | 8.9279 | 9.3183 | 8.643 | 8.5673 | 9.0269 | 8.7019 | 8.8695 | 8.9493 | 9.6528 | 8.8792 | 0.3619 | 0.971 | -0.2016 |
| hsa-miR-614 | 8.7253 | 8.0146 | 8.5642 | 8.302 | 8.3773 | 8.2091 | 8.2136 | 8.4254 | 8.9493 | 9.3738 | 8.3866 | 0.4104 | 0.9744 | -0.1963 |
| hsa-miR-629-5p | 8.5476 | 8.0619 | 8.4288 | 8.2696 | 8.2275 | 8.6303 | 8.1098 | 8.2471 | 8.9493 | 8.873 | 8.2082 | 0.2845 | 0.9634 | -0.1959 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-548c-3p | 7.8262 | 7.8357 | 8.1128 | 8.2025 | 7.5129 | 8.1844 | 7.9263 | 7.9992 | 8.6704 | 8.2325 | 7.5453 | 0.344 | 0.9696 | −0.195 |
| hsa-miR-216a | 8.2892 | 7.8626 | 8.5425 | 8.3337 | 7.6538 | 8.2334 | 8.066 | 8.1691 | 8.529 | 8.8999 | 8.0478 | 0.4012 | 0.9738 | −0.1878 |
| hsa-miR-655 | 7.4748 | 7.1952 | 7.3054 | 7.454 | 6.751 | 7.414 | 6.9017 | 7.0866 | 8.1964 | 7.8455 | 7.0896 | 0.4675 | 0.9774 | −0.1862 |
| hsa-miR-892b | 8.4497 | 7.9406 | 8.668 | 8.1677 | 7.585 | 8.4762 | 8.0881 | 8.228 | 8.2229 | 8.8455 | 8.2271 | 0.4287 | 0.9754 | −0.1857 |
| hsa-miR-302c-3p | 7.7461 | 7.4297 | 7.5856 | 7.5106 | 7.0854 | 7.8183 | 7.5983 | 7.4911 | 8.3723 | 7.6044 | 7.0478 | 0.4032 | 0.9739 | −0.1839 |
| hsa-miR-1289 | 8.1404 | 7.5672 | 8.0527 | 8.1321 | 7.8124 | 7.9115 | 7.8511 | 7.8321 | 8.3242 | 8.6686 | 8.1501 | 0.3235 | 0.9677 | −0.182 |
| hsa-miR-769-5p | 9.2315 | 8.9406 | 9.5856 | 8.8545 | 8.7353 | 8.8811 | 8.8251 | 9.0326 | 9.9254 | 9.9652 | 8.8792 | 0.5168 | 0.9795 | −0.1819 |
| hsa-miR-525-5p | 8.3172 | 8.237 | 8.1128 | 8.454 | 8.1817 | 8.5553 | 8.436 | 8.1077 | 8.8678 | 9.1223 | 7.5453 | 0.4805 | 0.978 | −0.1785 |
| hsa-miR-518f-3p | 7.6612 | 6.7517 | 6.8904 | 7.2024 | 6.5494 | 7.0269 | 6.7442 | 6.7541 | 7.5708 | 7.8999 | 7.1302 | 0.5307 | 0.9801 | −0.1767 |
| hsa-miR-371b-5p | 8.1087 | 7.6927 | 8.1705 | 7.5106 | 7.8124 | 7.8811 | 7.9263 | 7.643 | 8.0854 | 8.6686 | 8.0047 | 0.374 | 0.9719 | −0.1758 |
| hsa-miR-371a-3p | 8.4748 | 8.3932 | 8.4523 | 8.6175 | 8.3974 | 8.5744 | 8.3291 | 8.2846 | 8.8166 | 9.1674 | 8.6468 | 0.2718 | 0.9618 | −0.1694 |
| hsa-miR-1269b | 7.4242 | 6.6928 | 7.142 | 6.98 | 7.1344 | 7.1845 | 6.9017 | 7.1285 | 7.3957 | 7.8455 | 7.0047 | 0.3803 | 0.9724 | −0.1688 |
| hsa-miR-296-3p | 7.2017 | 6.9658 | 7.4981 | 6.3951 | 6.2275 | 6.6485 | 6.5032 | 8.1285 | 7.4859 | 7.73 | 7.0896 | 0.6057 | 0.9825 | −0.1685 |
| hsa-miR-665 | 8.4994 | 8.1301 | 8.8379 | 8.0956 | 8.2048 | 8.4557 | 8.436 | 6.9534 | 8.901 | 9.0519 | 8.1501 | 0.4467 | 0.9764 | −0.167 |
| hsa-miR-1245a | 7.4748 | 6.7517 | 7.3561 | 7.5651 | 6.6869 | 7.1338 | 7.0436 | 8.2321 | 7.7991 | 7.8999 | 7.1697 | 0.5228 | 0.9798 | −0.1664 |
| hsa-miR-936 | 8.2262 | 8.2777 | 8.2795 | 7.1321 | 7.7193 | 8.0269 | 7.5983 | 7.3915 | 8.2229 | 8.4304 | 7.9376 | 0.5314 | 0.9801 | −0.1611 |
| hsa-miR-1266 | 8.0091 | 7.5996 | 8.226 | 7.7643 | 7.585 | 8.0544 | 7.7161 | 7.3915 | 8.6704 | 8.6996 | 7.4521 | 0.5668 | 0.9813 | −0.1605 |
| hsa-miR-1291 | 7.8647 | 7.8357 | 8.0527 | 7.9801 | 7.8124 | 8.1078 | 7.7161 | 7.7541 | 8.6115 | 8.6369 | 7.55 | 0.4532 | 0.9767 | −0.1578 |
| hsa-miR-509-3-5p | 8.0091 | 7.6313 | 7.668 | 6.717 | 7.2718 | 7.7859 | 7.4012 | 7.3568 | 8.0265 | 7.467 | 7.6607 | 0.5438 | 0.9805 | −0.1569 |
| hsa-miR-2054 | 7.8262 | 7.5672 | 7.8904 | 7.3951 | 6.9824 | 7.7188 | 7.7716 | 7.2471 | 7.7991 | 8.467 | 7.1302 | 0.5529 | 0.9808 | −0.1567 |
| hsa-miR-585 | 8.0091 | 7.6623 | 7.9575 | 8.2364 | 8.3422 | 7.9412 | 8.1098 | 7.7805 | 8.3484 | 8.6044 | 7.7932 | 0.3713 | 0.9717 | −0.1547 |
| hsa-miR-548j | 8.2607 | 8.0146 | 8.226 | 8.0956 | 7.7821 | 8.3488 | 8.0881 | 7.7805 | 8.5708 | 8.6996 | 7.8911 | 0.4028 | 0.9739 | −0.154 |
| hsa-miR-765 | 7.4748 | 7.534 | 7.7835 | 7.9801 | 7.5129 | 7.7188 | 7.6584 | 7.1691 | 8.2744 | 8.467 | 7.575 | 0.5041 | 0.979 | −0.1534 |
| hsa-miR-1913 | 7.5237 | 7.4297 | 7.4981 | 7.6175 | 6.4754 | 7.6118 | 7.5673 | 7.2471 | 7.6115 | 8.0519 | 6.6608 | 0.612 | 0.9827 | −0.1495 |
| hsa-miR-4425 | 8.8066 | 8.7943 | 8.7076 | 9.1139 | 8.751 | 9.0679 | 8.8381 | 8.5227 | 9.236 | 9.5713 | 8.8607 | 0.4234 | 0.9751 | −0.1481 |
| hsa-miR-1297 | 8.0431 | 7.9904 | 8.0831 | 7.6681 | 7.9824 | 8.1078 | 7.5355 | 7.906 | 8.5501 | 8.73 | 7.7677 | 0.4956 | 0.9787 | −0.1461 |
| hsa-miR-659-3p | 9.1867 | 8.6469 | 8.8904 | 9.2859 | 8.4754 | 9.0947 | 8.673 | 8.7936 | 9.3957 | 9.8174 | 8.4839 | 0.5814 | 0.9818 | −0.146 |
| hsa-miR-548g-3p | 8.2018 | 7.7802 | 8.6479 | 8.5106 | 8.0854 | 8.3037 | 8.1934 | 8.1489 | 8.7635 | 8.9264 | 8.0047 | 0.5186 | 0.9796 | −0.1449 |
| hsa-miR-605 | 8.6612 | 8.3557 | 8.6066 | 8.6681 | 8.3974 | 8.8022 | 8.3656 | 8.3742 | 8.7635 | 9.3149 | 8.4681 | 0.408 | 0.9742 | −0.1436 |
| hsa-miR-553 | 8.8836 | 8.534 | 8.3055 | 8.6928 | 8.4943 | 8.3926 | 8.5194 | 8.4586 | 8.9334 | 9.467 | 8.575 | 0.4838 | 0.9782 | −0.1423 |
| hsa-miR-499a-5p | 8.4497 | 8.4297 | 8.4981 | 8.1677 | 7.8999 | 8.3709 | 8.8766 | 8.507 | 8.6115 | 9.2111 | 8.0047 | 0.5485 | 0.9807 | −0.1413 |
| hsa-miR-502-3p | 8.8066 | 8.2976 | 8.5205 | 8.3337 | 8.1101 | 8.6119 | 8.2916 | 8.507 | 8.7814 | 8.9264 | 8.2082 | 0.4121 | 0.9745 | −0.1407 |
| hsa-miR-548d-5p | 7.6168 | 7.1078 | 7.668 | 7.6175 | 7.0349 | 7.5744 | 7.5031 | 7.3211 | 7.5708 | 8.0992 | 7.2082 | 0.4831 | 0.9781 | −0.1371 |
| hsa-miR-943 | 8.4748 | 7.8357 | 8.1705 | 7.1321 | 8.0604 | 8.2807 | 7.8511 | 7.5841 | 8.1695 | 8.6996 | 7.9827 | 0.5041 | 0.979 | −0.1315 |
| hsa-miR-548n | 8.4748 | 8.5835 | 8.5856 | 8.643 | 7.9824 | 8.2091 | 8.1311 | 8.6574 | 8.9493 | 9.3738 | 8.1891 | 0.5973 | 0.9822 | −0.1311 |
| hsa-miR-1268b | 7.3717 | 7.0147 | 7.142 | 7.2024 | 7.3568 | 7.6484 | 7.2916 | 7.0866 | 8.5383 | 7.6686 | 6.8672 | 0.4065 | 0.9741 | −0.131 |
| hsa-miR-1208 | 9.1246 | 8.7516 | 8.5425 | 8.643 | 8.437 | 8.7015 | 8.7986 | 8.5383 | 9.1558 | 9.467 | 8.3179 | 0.5479 | 0.9807 | −0.1301 |
| hsa-miR-1295a | 7.9022 | 7.2777 | 7.5856 | 7.3951 | 7.437 | 7.9115 | 7.3656 | 7.2086 | 9.1558 | 8.0519 | 7.6327 | 0.4621 | 0.9772 | −0.13 |
| hsa-miR-508-3p | 7.8262 | 7.7516 | 7.7076 | 7.3337 | 7.0854 | 8.0544 | 6.6875 | 6.6875 | 7.727 | 8.1894 | 7.7677 | 0.6498 | 0.9837 | −0.1285 |
| hsa-miR-548b-5p | 7.6168 | 6.8083 | 7.142 | 7.7171 | 7.0854 | 7.9115 | 6.9979 | 6.9979 | 7.727 | 8.0992 | 7.0478 | 0.6138 | 0.9827 | −0.1283 |
| hsa-miR-323b-5p | 7.7867 | 7.9657 | 8.0216 | 7.6681 | 7.5129 | 7.8501 | 7.5673 | 7.4911 | 8.2744 | 8.8455 | 7.4838 | 0.5479 | 0.9807 | −0.1277 |
| hsa-miR-1273e | 8.2892 | 7.9151 | 8.226 | 7.9394 | 6.6198 | 8.2091 | 7.5031 | 7.906 | 8.4188 | 8.8175 | 7.8911 | 0.6142 | 0.9819 | −0.1264 |
| hsa-miR-1294 | 8.4242 | 8.4297 | 8.4981 | 8.565 | 7.7513 | 8.1338 | 8.1311 | 7.9764 | 8.529 | 8.9779 | 7.8429 | 0.5868 | 0.9822 | −0.126 |
| hsa-miR-616-3p | 8.0091 | 7.3557 | 7.9899 | 7.9394 | 7.3568 | 8.1338 | 7.7441 | 7.5537 | 7.6894 | 8.2325 | 7.6882 | 0.5955 | 0.9799 | −0.1232 |
| hsa-miR-1278 | 7.7461 | 7.6623 | 7.7835 | 7.3337 | 7.3974 | 7.684 | 7.5673 | 7.1691 | 8.2995 | 8.2325 | 7.2823 | 0.5884 | 0.982 | −0.1212 |
| hsa-miR-372 | 8.3717 | 8.0385 | 8.3561 | 8.2025 | 8.1124 | 8.3037 | 7.9017 | 8.0653 | 8.8339 | 8.5713 | 7.9827 | 0.5278 | 0.98 | −0.1202 |
| hsa-miR-518d-3p | 7.3717 | 6.6312 | 7.0831 | 7.2024 | 6.8125 | 7.1845 | 6.2135 | 6.8571 | 7.5708 | 8.145 | 6.8672 | 0.7042 | 0.9849 | −0.1195 |
| hsa-miR-1301 | 7.9744 | 7.3932 | 7.7835 | 7.9801 | 7.1817 | 7.6484 | 7.6584 | 7.4586 | 8.2229 | 8.2743 | 7.4197 | 0.609 | 0.9826 | −0.1178 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-3144-5p | 8.2018 | 7.5001 | 7.8557 | 7.8976 | 7.8422 | 8.0269 | 7.6584 | 7.4911 | 8.486 | 8.3545 | 7.8429 | 0.5621 | 0.9812 | -0.1171 |
| hsa-miR-591 | 7.1404 | 7.7225 | 8.0831 | 7.1321 | 7.0349 | 7.2807 | 7.3291 | 6.5228 | 8.1964 | 8.0519 | 7.8429 | 0.7332 | 0.9855 | -0.1147 |
| hsa-miR-517a-3p | 8.6392 | 8.822 | 8.8904 | 8.2364 | 8.4173 | 8.8811 | 8.436 | 8.5383 | 9.0415 | 8.9779 | 8.4032 | 0.5256 | 0.9799 | -0.1119 |
| hsa-miR-524-5p | 8.4748 | 7.8626 | 8.4288 | 8.3647 | 8.0349 | 8.3265 | 7.9744 | 8.9764 | 8.6314 | 9.0277 | 8.1302 | 0.6071 | 0.9825 | -0.1113 |
| hsa-miR-520f | 8.3717 | 8.3366 | 8.5856 | 8.565 | 9.6198 | 8.4557 | 8.0881 | 7.8572 | 8.5076 | 8.7597 | 11.1673 | 0.8451 | 0.9874 | -0.1102 |
| hsa-miR-346 | 8.2018 | 7.6313 | 7.9243 | 8.1321 | 7.7511 | 8.1844 | 7.5355 | 7.4911 | 8.5913 | 8.7597 | 7.6607 | 0.6775 | 0.9843 | -0.109 |
| hsa-miR-3180-5p | 7.9022 | 8.085 | 8.0831 | 8.1677 | 8.336 | 8.0544 | 8.0437 | 7.7541 | 8.6314 | 8.6996 | 8.1501 | 0.5385 | 0.9803 | -0.1074 |
| hsa-miR-563 | 8.7253 | 8.1521 | 8.2795 | 8.643 | 7.8422 | 8.5553 | 8.2916 | 7.9299 | 8.7635 | 9.003 | 8.0688 | 0.6588 | 0.9839 | -0.1069 |
| hsa-miR-3168 | 8.3717 | 8.3932 | 8.5425 | 8.4248 | 7.585 | 8.3265 | 8.2531 | 8.189 | 8.6895 | 9.0992 | 7.6607 | 0.6957 | 0.9847 | -0.1062 |
| hsa-miR-1269a | 7.7461 | 7.2371 | 7.7076 | 7.6175 | 7.5129 | 7.4557 | 7.4012 | 7.5537 | 8.0854 | 8.393 | 7.1302 | 0.6358 | 0.9833 | -0.1057 |
| hsa-miR-4421 | 8.6829 | 8.534 | 8.7076 | 8.8976 | 8.437 | 8.3488 | 8.6876 | 8.3742 | 9.128 | 9.2948 | 8.7018 | 0.5735 | 0.9815 | -0.104 |
| hsa-miR-548p | 9.3982 | 8.9657 | 9.4868 | 9.3493 | 9.1582 | 9.5163 | 9.1098 | 8.9649 | 9.6607 | 9.9652 | 9.0371 | 0.5963 | 0.9822 | -0.104 |
| hsa-miR-661 | 8.5237 | 8.0146 | 8.3561 | 8.0196 | 8.336 | 8.5359 | 8.0881 | 8.1285 | 8.7269 | 8.7597 | 7.8672 | 0.5942 | 0.9829 | -0.101 |
| hsa-miR-1273d | 8.3717 | 8.085 | 8.226 | 8.4248 | 8.2048 | 8.3709 | 8.2335 | 7.7541 | 8.8509 | 8.8999 | 8.0688 | 0.62 | 0.9836 | -0.1006 |
| hsa-miR-1273c | 6.4241 | 6.6312 | 6.746 | 6.98 | 6.5494 | 7.0814 | 6.3656 | 6.2472 | 6.7634 | 7.3929 | 6.7152 | 0.6479 | 0.9847 | -0.0948 |
| hsa-miR-3676-3p | 8.3172 | 8.3932 | 8.3561 | 7.9801 | 7.6869 | 8.5359 | 7.9017 | 8.4586 | 8.2995 | 8.73 | 7.5149 | 0.6937 | 0.9856 | -0.0934 |
| hsa-miR-2110 | 8.3717 | 8.2777 | 8.5856 | 8.5106 | 7.585 | 8.4139 | 8.0881 | 8.1285 | 8.7083 | 9.0992 | 7.7152 | 0.7381 | 0.9857 | -0.0928 |
| hsa-miR-548an | 8.3717 | 8.0385 | 8.1985 | 8.3647 | 7.4754 | 8.0269 | 7.9979 | 7.7541 | 8.5076 | 8.5713 | 7.8429 | 0.7002 | 0.9848 | -0.0928 |
| hsa-miR-1224-3p | 7.4242 | 6.8083 | 6.9576 | 6.98 | 6.4754 | 7.0814 | 6.7442 | 6.2472 | 7.5708 | 7.0519 | 6.7152 | 0.6614 | 0.9839 | -0.0908 |
| hsa-miR-769-3p | 8.6612 | 7.9657 | 8.82 | 8.6928 | 7.6869 | 8.2091 | 8.066 | 8.2086 | 9.0114 | 9.2111 | 8.0264 | 0.6776 | 0.9863 | -0.0901 |
| hsa-miR-548s | 8.0091 | 8.085 | 8.3561 | 8.4248 | 7.8422 | 8.0269 | 8.2531 | 7.6716 | 8.6314 | 8.7889 | 8.0264 | 0.6688 | 0.9841 | -0.0896 |
| hsa-miR-1256 | 8.3717 | 8.1301 | 8.0216 | 7.9394 | 7.9824 | 8.1844 | 7.8321 | 7.8321 | 8.5076 | 8.8999 | 7.3179 | 0.7191 | 0.9852 | -0.0895 |
| hsa-miR-1243 | 8.3172 | 7.2777 | 7.9575 | 7.7643 | 6.6199 | 7.3264 | 7.5673 | 7.2471 | 7.9962 | 8.6044 | 7.3179 | 0.8136 | 0.9869 | -0.0892 |
| hsa-miR-516b-5p | 8.571 | 8.1521 | 8.226 | 8.3337 | 8.2048 | 8.3709 | 8.3105 | 7.9992 | 8.6314 | 9.2111 | 7.7932 | 0.6971 | 0.9847 | -0.0885 |
| hsa-miR-371b-3p | 7.6168 | 7.8626 | 8.3055 | 7.5106 | 7.7511 | 8.0269 | 7.0436 | 7.5537 | 8.114 | 8.5373 | 8.11 | 0.7367 | 0.9856 | -0.0883 |
| hsa-miR-577 | 7.8262 | 7.2777 | 8.3055 | 7.8546 | 7.6869 | 7.8501 | 7.1729 | 7.9992 | 8.486 | 8.2743 | 7.4838 | 0.7431 | 0.9857 | -0.0875 |
| hsa-miR-1244 | 8.9206 | 8.2976 | 8.6274 | 8.302 | 8.0349 | 8.4762 | 8.3474 | 8.2659 | 8.8166 | 9.1223 | 8.11 | 0.6999 | 0.9848 | -0.0866 |
| hsa-miR-518e-5p | 8.7461 | 8.085 | 8.746 | 8.2696 | 8.2696 | 8.3709 | 8.2725 | 8.3742 | 8.9961 | 8.9524 | 8.2641 | 0.6649 | 0.984 | -0.0856 |
| hsa-miR-300 | 8.2018 | 7.8357 | 7.5425 | 8.3951 | 7.8422 | 8.1078 | 7.7441 | 8.1077 | 8.1695 | 8.6996 | 7.6327 | 0.6973 | 0.9847 | -0.0854 |
| hsa-miR-876-5p | 7.2607 | 7.5996 | 8.0216 | 8.0216 | 7.9824 | 7.4557 | 7.2531 | 8.0215 | 8.0265 | 8.393 | 7.9145 | 0.7263 | 0.9854 | -0.0827 |
| hsa-miR-548z | 9.0762 | 8.3366 | 8.8556 | 7.8976 | 8.6704 | 8.7359 | 8.3474 | 7.4911 | 9.2097 | 8.924 | 8.6327 | 0.6759 | 0.9843 | -0.0823 |
| hsa-miR-11184 | 7.5237 | 6.6312 | 7.7076 | 7.1321 | 7.437 | 6.9115 | 7.0436 | 7.2846 | 7.727 | 8.1894 | 7.0478 | 0.7761 | 0.9863 | -0.081 |
| hsa-miR-548ah-5p | 8.8263 | 8.5835 | 8.941 | 8.9599 | 8.6025 | 8.85 | 8.7716 | 8.6716 | 8.8845 | 9.6045 | 8.3866 | 0.6814 | 0.9844 | -0.0788 |
| hsa-miR-548c-5p | 8.2607 | 7.8891 | 8.3055 | 8.2364 | 7.7821 | 8.1844 | 8.021 | 8.0215 | 8.3957 | 8.73 | 7.6882 | 0.6751 | 0.9843 | -0.0787 |
| hsa-miR-2133 | 8.1404 | 7.5001 | 7.5856 | 7.5106 | 7.2275 | 7.5744 | 7.2531 | 7.4911 | 7.9962 | 8.467 | 7.2456 | 0.757 | 0.9859 | -0.0784 |
| hsa-miR-11185-5p | 9.3447 | 8.8626 | 8.9244 | 8.8545 | 8.5673 | 8.9114 | 9.0437 | 8.3915 | 9.3119 | 9.5713 | 8.6882 | 0.7317 | 0.9855 | -0.0756 |
| hsa-miR-892a | 8.2018 | 7.4297 | 8.0216 | 8.0196 | 7.7821 | 7.9989 | 7.9017 | 7.6716 | 8.2229 | 8.2325 | 7.7677 | 0.6596 | 0.9839 | -0.0749 |
| hsa-miR-1245b-5p | 8.3981 | 7.7225 | 7.9243 | 7.5106 | 7.7193 | 8.1338 | 7.8511 | 7.4254 | 7.7991 | 8.4304 | 7.9376 | 0.7237 | 0.9853 | -0.0746 |
| hsa-miR-559 | 8.4748 | 8.4116 | 8.5205 | 7.8101 | 7.9554 | 8.5932 | 7.5031 | 8.1691 | 8.651 | 8.9524 | 7.9827 | 0.7826 | 0.9864 | -0.0741 |
| hsa-miR-1249 | 7.7461 | 7.6313 | 7.4981 | 8.0956 | 7.8999 | 8.1594 | 7.47 | 7.7541 | 8.0563 | 8.0992 | 7.5453 | 0.659 | 0.9839 | -0.0732 |
| hsa-miR-1245b-3p | 7.8647 | 7.1078 | 7.5425 | 7.5106 | 7.0854 | 7.7188 | 7.5031 | 7.5227 | 7.9334 | 7.8455 | 7.4197 | 0.7881 | 0.9865 | -0.0723 |
| hsa-miR-583 | 8.0431 | 7.3172 | 8.0831 | 7.6681 | 7.3974 | 7.5744 | 7.2916 | 7.2846 | 8.2229 | 8.6369 | 7.6327 | 0.7979 | 0.9866 | -0.0721 |
| hsa-miR-506-3p | 8.1404 | 8.085 | 8.5205 | 7.3951 | 7.7821 | 8.1844 | 7.825 | 7.7541 | 7.9962 | 8.6686 | 7.7778 | 0.7778 | 0.9863 | -0.0719 |
| hsa-miR-2114-5p | 8.6612 | 8.0619 | 8.5205 | 8.2364 | 8.1582 | 8.2334 | 8.1098 | 8.303 | 8.529 | 8.9779 | 7.9827 | 0.6984 | 0.9848 | -0.0713 |
| hsa-miR-548ab | 7.6168 | 7.3932 | 7.8904 | 7.3951 | 7.5494 | 7.8501 | 7.2531 | 7.0866 | 7.8338 | 8.393 | 7.4197 | 0.7544 | 0.9859 | -0.0704 |
| hsa-miR-1273a | 8.3447 | 8.0619 | 8.3561 | 8.0196 | 7.4754 | 8.2572 | 7.825 | 7.6996 | 8.4415 | 9.0519 | 7.4521 | 0.8139 | 0.9869 | -0.0697 |
| hsa-miR-557 | 8.3717 | 7.6927 | 8.1705 | 8.2025 | 7.4754 | 8.1844 | 7.7161 | 7.5841 | 8.1695 | 8.7889 | 7.8672 | 0.7844 | 0.9864 | -0.0691 |
| hsa-miR-520d-3p | 7.5237 | 7.6927 | 7.7835 | 7.2696 | 7.6538 | 7.7859 | 7.6286 | 7.2471 | 7.6894 | 8.145 | 7.4197 | 0.6716 | 0.9842 | -0.068 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-490-5p | 7.9744 | 7.3557 | 8.0216 | 7.454 | 7.1817 | 7.3264 | 7.6286 | 7.2846 | 7.901 | 8.4304 | 7.4197 | 0.79 | 0.9865 | -0.0676 |
| hsa-miR-129-5p | 7.8262 | 7.3557 | 7.4981 | 7.5651 | 7.437 | 7.6118 | 7.1729 | 7.5227 | 7.8678 | 8.2743 | 7.1697 | 0.7367 | 0.9856 | -0.0668 |
| hsa-miR-1908 | 8.8066 | 8.2976 | 8.1128 | 8.643 | 8.2275 | 8.4762 | 8.5031 | 8.3742 | 8.6115 | 8.8455 | 8.0896 | 0.7032 | 0.9849 | -0.0658 |
| hsa-miR-1321 | 8.3172 | 7.8082 | 7.8201 | 8.3647 | 8.0854 | 7.9703 | 7.9506 | 8.7065 | 8.3723 | 8.7597 | 8.0047 | 0.7368 | 0.9856 | -0.0649 |
| hsa-miR-1972 | 8.5941 | 8.2163 | 8.331 | 8.6175 | 8.0854 | 7.8811 | 8.2531 | 8.8818 | 8.3957 | 9.1674 | 8.0047 | 0.7958 | 0.9866 | -0.0618 |
| hsa-miR-890 | 8.9387 | 8.5835 | 8.331 | 8.454 | 8.1344 | 8.7359 | 8.1522 | 8.228 | 8.6895 | 9.0758 | 8.4197 | 0.7597 | 0.986 | -0.0618 |
| hsa-miR-548k | 9.1087 | 8.5996 | 8.7649 | 8.8102 | 8.3773 | 8.7859 | 8.4012 | 8.4586 | 9.114 | 9.4118 | 8.5897 | 0.7689 | 0.9862 | -0.0614 |
| hsa-miR-1471 | 8.2315 | 7.7802 | 7.9575 | 8.0196 | 7.7821 | 7.8183 | 8.1311 | 7.5537 | 8.0854 | 8.7597 | 7.7417 | 0.761 | 0.986 | -0.0608 |
| hsa-miR-576-3p | 7.5237 | 7.4653 | 7.8201 | 7.3951 | 7.315 | 7.4964 | 7.2916 | 7.2086 | 7.8678 | 8.0992 | 7.4197 | 0.7271 | 0.9854 | -0.0601 |
| hsa-miR-548t-5p | 8.7461 | 8.4297 | 8.5205 | 8.5381 | 7.7821 | 8.3488 | 8.1311 | 8.0653 | 8.8509 | 9.1894 | 8.1891 | 0.8164 | 0.9869 | -0.0592 |
| hsa-miR-2276 | 8.8456 | 8.2163 | 8.7269 | 8.8762 | 8.3568 | 8.4557 | 8.6135 | 8.3567 | 8.9651 | 9.0519 | 8.5301 | 0.7516 | 0.9858 | -0.0578 |
| hsa-miR-518c-3p | 8.571 | 7.8943 | 8.8379 | 8.8325 | 8.5129 | 8.8342 | 8.4866 | 8.4749 | 8.9493 | 9.2535 | 8.6041 | 0.6982 | 0.9848 | -0.0574 |
| hsa-miR-384 | 9.7767 | 9.4476 | 8.899 | 9.8436 | 9.0978 | 9.6663 | 9.4949 | 9.4668 | 9.7453 | 10.3049 | 9.3353 | 0.7922 | 0.9866 | -0.056 |
| hsa-miR-875-3p | 8.1714 | 7.9657 | 8.1128 | 8.3337 | 7.8124 | 8.2572 | 7.825 | 7.7541 | 8.5913 | 8.8999 | 7.4838 | 0.7597 | 0.987 | -0.056 |
| hsa-miR-520a-3p | 8.4242 | 6.8083 | 8.0216 | 8.7643 | 7.6869 | 7.9115 | 7.9744 | 8.0436 | 8.3242 | 8.5713 | 7.7932 | 0.8217 | 0.9861 | -0.0544 |
| hsa-miR-1261 | 7.0763 | 7.8891 | 7.4981 | 7.3337 | 7.1817 | 7.8183 | 6.9506 | 6.5841 | 7.142 | 9.1223 | 7.9376 | 0.844 | 0.9873 | -0.0544 |
| hsa-miR-4484 | 8.3717 | 7.5996 | 8.5856 | 8.0956 | 7.9824 | 8.435 | 7.4012 | 8.0436 | 8.3484 | 8.8175 | 8.1501 | 0.8311 | 0.9872 | -0.0538 |
| hsa-miR-297 | 9.1087 | 8.7077 | 8.331 | 9.41 | 8.585 | 9.013 | 8.7019 | 8.8818 | 9.1558 | 9.3738 | 7.2456 | 0.7832 | 0.9864 | -0.0524 |
| hsa-miR-1263 | 8.4242 | 7.7225 | 8.7269 | 7.9801 | 8.0349 | 8.1078 | 8.0881 | 8.4911 | 8.6704 | 8.5713 | 7.5149 | 0.8356 | 0.9872 | -0.0515 |
| hsa-miR-941 | 9.0262 | 8.3366 | 8.8019 | 8.7124 | 8.2719 | 8.4762 | 8.7441 | 8.303 | 8.9651 | 9.3349 | 8.4032 | 0.8593 | 0.9876 | -0.0514 |
| hsa-miR-1914-5p | 8.0762 | 7.9151 | 8.0216 | 7.9394 | 7.6538 | 7.9989 | 7.9017 | 7.3568 | 8.2489 | 8.8999 | 7.4197 | 0.8219 | 0.987 | -0.0506 |
| hsa-miR-138-5p | 7.8262 | 7.3932 | 7.6274 | 7.5651 | 7.3568 | 7.684 | 7.2916 | 7.4586 | 8.0854 | 8.2325 | 6.8672 | 0.8453 | 0.9874 | -0.0497 |
| hsa-miR-625-5p | 8.4748 | 8.0146 | 7.8201 | 8.1677 | 7.6538 | 7.7188 | 7.6876 | 7.9534 | 8.3957 | 8.9264 | 7.7677 | 0.8322 | 0.9872 | -0.0495 |
| hsa-miR-34b-3p | 8.7043 | 8.1738 | 8.4523 | 8.058 | 7.3568 | 8.2572 | 7.5983 | 7.8321 | 8.5076 | 9.0758 | 7.9145 | 0.8477 | 0.9874 | -0.0487 |
| hsa-miR-640 | 7.571 | 7.5001 | 7.8557 | 6.8976 | 7.5129 | 7.3709 | 7.436 | 7.5841 | 7.8338 | 8.145 | 6.7152 | 0.8815 | 0.9879 | -0.0485 |
| hsa-miR-626 | 9.156 | 8.7802 | 8.9244 | 8.565 | 8.5494 | 8.5932 | 8.5355 | 8.6574 | 9.4416 | 9.4118 | 8.4032 | 0.857 | 0.9876 | -0.0467 |
| hsa-miR-215 | 11.0966 | 11.9087 | 11.2696 | 8.3951 | 9.1582 | 7.7859 | 7.7986 | 8.8818 | 12.8668 | 14.2568 | 10.8762 | 0.8417 | 0.9873 | -0.0455 |
| hsa-miR-520e | 7.1404 | 6.8083 | 7.4523 | 7.3951 | 6.4754 | 7.0269 | 6.851 | 6.8066 | 7.2995 | 7.8455 | 6.7677 | 0.973 | 0.989 | -0.0454 |
| hsa-miR-1293 | 7.1404 | 6.7517 | 7.1985 | 7.2696 | 6.8714 | 7.0814 | 6.6286 | 6.7541 | 7.0854 | 7.7889 | 7.2082 | 0.8606 | 0.9876 | -0.0452 |
| hsa-miR-615-3p | 7.8262 | 7.4297 | 7.9575 | 7.454 | 7.4754 | 7.7188 | 7.0881 | 7.3211 | 8.2229 | 7.8455 | 7.8429 | 0.823 | 0.987 | -0.0448 |
| hsa-miR-937 | 8.1087 | 8.4828 | 8.2795 | 8.454 | 7.9824 | 8.2572 | 8.1934 | 7.8065 | 8.6314 | 8.73 | 8.2082 | 0.8281 | 0.9871 | -0.0446 |
| hsa-miR-550a-5p | 8.571 | 7.9151 | 8.2795 | 8.0196 | 8.1714 | 7.7527 | 7.9979 | 7.906 | 8.5501 | 8.5026 | 8.3353 | 0.8034 | 0.9867 | -0.043 |
| hsa-miR-374c-5p | 7.9388 | 7.4297 | 7.746 | 7.8546 | 7.0349 | 7.3709 | 7.6584 | 7.4254 | 7.8678 | 7.9524 | 7.575 | 0.8257 | 0.9871 | -0.0428 |
| hsa-miR-1237 | 8.1404 | 8.085 | 8.4288 | 7.8546 | 8.3974 | 8.2091 | 7.9263 | 7.9534 | 8.6115 | 8.6686 | 7.9603 | 0.8372 | 0.9873 | -0.0409 |
| hsa-miR-1264 | 8.3717 | 7.7516 | 7.9899 | 8.302 | 7.8422 | 7.9703 | 7.7986 | 8.0653 | 8.1964 | 8.5373 | 7.9827 | 0.8231 | 0.9871 | -0.0403 |
| hsa-miR-1539 | 8.4242 | 8.2777 | 8.5425 | 8.8325 | 8.1101 | 8.5932 | 8.0881 | 8.2086 | 8.7991 | 9.003 | 8.1697 | 0.8084 | 0.9868 | -0.0403 |
| hsa-miR-3175 | 8.2018 | 8.0385 | 8.4288 | 8.5106 | 7.928 | 8.4557 | 8.2531 | 8.3915 | 8.3242 | 8.9264 | 8.2082 | 0.8452 | 0.9874 | -0.0396 |
| hsa-miR-92b-3p | 7.8647 | 7.1522 | 7.5856 | 8.1677 | 7.5129 | 7.9989 | 7.436 | 7.2846 | 8.0265 | 8.003 | 7.4197 | 0.873 | 0.9878 | -0.0383 |
| hsa-miR-219-5p | 8.4497 | 8.7943 | 8.8379 | 8.4248 | 8.4943 | 8.4964 | 8.1311 | 8.5537 | 9.2229 | 9.1223 | 8.3001 | 0.8679 | 0.9877 | -0.0382 |
| hsa-miR-1265 | 7.2607 | 7.5001 | 7.405 | 7.1321 | 7.315 | 7.1338 | 7.2916 | 7.2471 | 7.4415 | 7.7889 | 7.2456 | 0.8569 | 0.9876 | -0.0376 |
| hsa-miR-519b-3p | 7.9744 | 7.8082 | 8.0831 | 7.8101 | 8.0349 | 7.8501 | 8.066 | 7.9764 | 8.066 | 8.315 | 7.5149 | 0.763 | 0.986 | -0.0355 |
| hsa-miR-452-5p | 7.7867 | 7.9904 | 8.0216 | 7.8546 | 7.8999 | 7.8811 | 7.825 | 7.643 | 8.142 | 8.6369 | 7.575 | 0.7872 | 0.9865 | -0.0352 |
| hsa-miR-3934 | 8.7867 | 8.8759 | 9.1705 | 8.6175 | 8.2719 | 8.9114 | 8.4699 | 8.643 | 9.0998 | 9.4849 | 8.0688 | 0.8379 | 0.9873 | -0.0351 |
| hsa-miR-1234 | 8.8836 | 8.5835 | 8.4288 | 8.6681 | 8.2936 | 8.3709 | 8.3105 | 9.1285 | 8.5076 | 9.1674 | 8.1501 | 0.8921 | 0.988 | -0.0343 |
| hsa-miR-2682-5p | 8.9918 | 8.766 | 8.8731 | 9.2025 | 8.8999 | 8.7859 | 8.9263 | 8.6857 | 9.0998 | 9.6996 | 8.6882 | 0.8494 | 0.9874 | -0.0343 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-1267 | 8.0762 | 6.9152 | 6.9576 | 6.8102 | 6.9824 | 7.0814 | 6.7442 | 7.1285 | 7.1964 | 7.8455 | 7.0896 | 0.9095 | 0.9883 | −0.0326 |
| hsa-miR-1272 | 8.4994 | 7.7516 | 7.8557 | 8.5381 | 7.5494 | 7.9412 | 8.021 | 7.906 | 8.1695 | 8.73 | 7.6607 | 0.9 | 0.9881 | −0.0325 |
| hsa-miR-650 | 7.6612 | 8.0619 | 7.8904 | 8.2364 | 7.7193 | 7.9989 | 7.6286 | 7.7805 | 8.3242 | 8.4304 | 7.5149 | 0.8657 | 0.9877 | −0.0324 |
| hsa-miR-556-5p | 7.571 | 6.8627 | 7.5856 | 7.3951 | 7.6198 | 7.8501 | 7.0881 | 6.9534 | 7.901 | 7.7889 | 7.0478 | 0.8955 | 0.9881 | −0.0314 |
| hsa-miR-522-3p | 8.0431 | 7.7225 | 8.1985 | 8.2025 | 7.315 | 8.0814 | 7.5673 | 7.4911 | 8.3484 | 8.2325 | 7.8429 | 0.8926 | 0.988 | −0.0309 |
| hsa-miR-511 | 8.4994 | 8.237 | 8.6066 | 8.4248 | 8.1101 | 8.1844 | 8.2136 | 8.4586 | 8.5708 | 9.1894 | 7.8183 | 0.8892 | 0.988 | −0.0302 |
| hsa-miR-1258 | 8.3981 | 8.1077 | 7.746 | 7.8976 | 7.6538 | 8.2807 | 7.7161 | 7.8818 | 8.142 | 8.315 | 7.6041 | 0.8753 | 0.9878 | −0.0293 |
| hsa-miR-1284 | 7.8262 | 7.5996 | 7.7076 | 8.0196 | 7.0349 | 7.6484 | 7.5983 | 7.2471 | 8.114 | 8.003 | 7.3866 | 0.8977 | 0.9881 | −0.0286 |
| hsa-miR-513c-5p | 8.2018 | 7.6623 | 7.6274 | 7.6175 | 7.4754 | 7.3264 | 7.5031 | 7.4586 | 8.3957 | 8.2743 | 7.5149 | 0.9025 | 0.9882 | −0.0286 |
| hsa-miR-450b-5p | 9.2462 | 8.8082 | 8.6879 | 8.7643 | 8.5313 | 8.7359 | 8.4531 | 8.6996 | 9.128 | 9.3349 | 8.6607 | 0.8805 | 0.9879 | −0.0278 |
| hsa-miR-567 | 8.6392 | 7.6623 | 8.1128 | 8.0956 | 7.8124 | 7.8811 | 7.7441 | 8.1285 | 8.3484 | 8.6996 | 7.7417 | 0.9116 | 0.9883 | −0.0261 |
| hsa-miR-887 | 7.7042 | 7.5672 | 7.4981 | 7.5651 | 7.3568 | 7.4964 | 6.9017 | 7.2471 | 7.9334 | 8.3545 | 7.4521 | 0.909 | 0.9883 | −0.0259 |
| hsa-miR-718 | 8.0762 | 8.1521 | 8.4288 | 7.7643 | 8.2719 | 8.1594 | 7.6584 | 7.8321 | 8.6895 | 8.873 | 7.7677 | 0.9196 | 0.9884 | −0.0246 |
| hsa-miR-523-3p | 7.571 | 7.1952 | 7.5856 | 7.3951 | 7.6869 | 7.4964 | 7.436 | 6.9992 | 7.727 | 8.2743 | 7.1302 | 0.9112 | 0.9883 | −0.0238 |
| hsa-miR-1537 | 8.4242 | 7.8082 | 8.142 | 8.3951 | 7.6198 | 8.0269 | 7.9506 | 7.8572 | 8.8678 | 8.2325 | 7.6607 | 0.9291 | 0.9885 | −0.0214 |
| hsa-miR-3184-5p | 8.9022 | 8.1077 | 8.668 | 8.3337 | 8.0349 | 8.3488 | 8.5194 | 7.8818 | 8.901 | 8.9264 | 8.0047 | 0.9331 | 0.9886 | −0.021 |
| hsa-miR-188-3p | 8.4994 | 7.6623 | 8.405 | 7.8546 | 8.2719 | 8.1844 | 7.5673 | 8.4586 | 8.486 | 8.0519 | 7.4197 | 0.9196 | 0.9886 | −0.0191 |
| hsa-miR-3192 | 7.7867 | 7.3172 | 7.4981 | 7.2024 | 7.5129 | 7.7029 | 7.5673 | 7.4254 | 7.8338 | 7.7889 | 7.2456 | 0.9147 | 0.9883 | −0.0179 |
| hsa-miR-922 | 8.0431 | 7.6623 | 8.226 | 8.1677 | 8.0088 | 8.0269 | 8.021 | 7.8572 | 8.2744 | 8.393 | 7.6607 | 0.9089 | 0.9883 | −0.0173 |
| hsa-miR-1285-3p | 8.2018 | 7.534 | 7.746 | 7.7643 | 8.0854 | 7.7859 | 7.47 | 7.8065 | 7.9334 | 8.9524 | 7.3526 | 0.9496 | 0.9888 | −0.0171 |
| hsa-miR-1827 | 8.9387 | 8.9657 | 9.1128 | 9.1321 | 8.7032 | 9.172 | 8.7019 | 8.9764 | 9.2617 | 9.3738 | 8.436 | 0.9234 | 0.9884 | −0.0165 |
| hsa-miR-595 | 8.0091 | 7.3557 | 8.0527 | 7.454 | 7.1344 | 7.6118 | 7.0881 | 7.3211 | 8.1964 | 8.003 | 7.4838 | 0.9498 | 0.9888 | −0.0162 |
| hsa-miR-606 | 8.7867 | 8.5507 | 8.746 | 8.77874 | 8.5359 | 8.5559 | 8.6436 | 8.303 | 8.6895 | 9.6528 | 8.1697 | 0.9459 | 0.9887 | −0.0161 |
| hsa-miR-617 | 7.2607 | 7.2777 | 7.746 | 6.8102 | 6.751 | 7.414 | 6.7986 | 6.9534 | 7.3485 | 7.5374 | 7.0478 | 0.9498 | 0.9888 | −0.0141 |
| hsa-miR-3154 | 7.8262 | 7.9151 | 7.7835 | 7.5106 | 7.2275 | 7.2333 | 7.2531 | 7.4911 | 7.9334 | 8.6996 | 7.3866 | 0.9602 | 0.9889 | −0.0136 |
| hsa-miR-1231 | 9.0925 | 8.5672 | 8.7649 | 8.3951 | 8.2936 | 8.6119 | 8.173 | 8.2659 | 8.7991 | 9.467 | 8.4994 | 0.9563 | 0.9888 | −0.0134 |
| hsa-miR-548ai | 9.3311 | 8.9406 | 8.6274 | 8.3337 | 8.3773 | 9.6119 | 7.6584 | 8.1489 | 9.2617 | 7.7889 | 8.2282 | 0.9729 | 0.989 | −0.0133 |
| hsa-miR-4455 | 9.3173 | 9.0736 | 8.9075 | 8.8325 | 8.6369 | 8.9412 | 8.4187 | 8.7406 | 9.5913 | 9.4488 | 8.6327 | 0.9698 | 0.989 | −0.0087 |
| hsa-miR-448 | 9.571 | 9.3839 | 9.3929 | 9.5915 | 9.9279 | 9.6302 | 9.0437 | 8.894 | 9.7991 | 9.7744 | 9.1501 | 0.9675 | 0.989 | −0.0085 |
| hsa-miR-571 | 8.2018 | 7.6927 | 8.4754 | 9.1321 | 7.0854 | 8.0269 | 7.6286 | 7.6716 | 8.5501 | 8.6044 | 7.4521 | 0.9835 | 0.9891 | −0.0071 |
| hsa-miR-455-3p | 9.4497 | 8.9279 | 9.2925 | 8.454 | 8.437 | 9.1466 | 8.5515 | 8.9992 | 8.6895 | 9.467 | 8.6041 | 0.9839 | 0.9891 | −0.0051 |
| hsa-miR-644a | 9.0925 | 8.5172 | 9.0217 | 9.0956 | 8.4754 | 8.9558 | 7.6286 | 8.5537 | 9.0998 | 9.5026 | 8.8429 | 0.9866 | 0.9892 | −0.0035 |
| hsa-miR-564 | 8.9744 | 8.8082 | 8.7835 | 8.565 | 8.4754 | 8.5359 | 8.5194 | 8.4085 | 8.5076 | 9.4118 | 8.6185 | 0.9999 | 0.9893 | 0 |
| hsa-miR-216b | 8.5941 | 8.3172 | 8.668 | 8.717 | 7.928 | 8.2807 | 8.5829 | 8.2471 | 8.5076 | 9.2535 | 7.7932 | 0.9978 | 0.9893 | 0.0007 |
| hsa-miR-593-3p | 8.0762 | 7.6927 | 8.226 | 7.8546 | 7.7821 | 7.9115 | 7.5031 | 7.9299 | 8.1964 | 8.467 | 7.5453 | 0.9966 | 0.9893 | 0.0008 |
| hsa-miR-711 | 8.1087 | 7.9657 | 8.0216 | 7.5106 | 7.5494 | 7.3264 | 7.9744 | 7.8321 | 8.3484 | 8.145 | 7.3526 | 0.9949 | 0.9893 | 0.0014 |
| hsa-miR-1226-3p | 8.6168 | 8.3557 | 8.746 | 8.9394 | 8.2499 | 8.6663 | 8.6584 | 8.1691 | 8.8166 | 9.1223 | 8.0478 | 0.9944 | 0.9893 | 0.0015 |
| hsa-miR-1197 | 8.6168 | 8.3746 | 8.9575 | 8.5106 | 8.2499 | 8.5932 | 8.1522 | 8.507 | 8.6895 | 9.1223 | 8.1697 | 0.9883 | 0.9892 | 0.0029 |
| hsa-miR-1909-3p | 8.5476 | 8.7077 | 8.9244 | 9.0196 | 8.5494 | 8.7527 | 8.5983 | 8.5991 | 8.7635 | 9.3149 | 8.4522 | 0.9855 | 0.9892 | 0.0029 |
| hsa-miR-378c | 8.3447 | 7.6623 | 7.7076 | 7.8546 | 7.9554 | 7.7811 | 7.6286 | 7.3915 | 8.7635 | 8.8175 | 7.575 | 0.9883 | 0.9892 | 0.0037 |
| hsa-miR-520d-5p + hsa-miR-518a-5p + hsa-miR-527 | 8.0091 | 7.8082 | 7.9575 | 9.15 | 7.6198 | 8.0544 | 8.0437 | 7.5227 | 8.1964 | 8.6996 | 8.11 | 0.989 | 0.9892 | 0.0044 |
| hsa-miR-1255b-5p | 8.4994 | 7.7225 | 7.9899 | 8.3647 | 7.8999 | 8.0269 | 7.9506 | 7.8321 | 8.3957 | 8.467 | 7.8672 | 0.9773 | 0.9891 | 0.0054 |
| hsa-miR-1280 | 7.3172 | 7.4297 | 8.0831 | 8.058 | 7.7193 | 7.9412 | 7.4012 | 7.4911 | 8.2229 | 8.1894 | 7.0478 | 0.9817 | 0.9891 | 0.0059 |
| hsa-miR-3180-3p | 8.3717 | 7.3932 | 8.0831 | 7.9394 | 7.4754 | 7.684 | 7.3291 | 7.6139 | 8.3484 | 8.467 | 7.6327 | 0.9802 | 0.9891 | 0.0067 |
| hsa-miR-208b | 7.9744 | 8.085 | 8.331 | 8.2025 | 8.0088 | 8.2572 | 7.8511 | 7.6996 | 8.4415 | 8.5373 | 7.8911 | 0.9636 | 0.9889 | 0.0074 |
| hsa-miR-491-3p | 8.571 | 8.0146 | 8.0831 | 8.3647 | 7.9554 | 7.8501 | 7.9017 | 7.8065 | 8.6115 | 8.8999 | 8.0688 | 0.9718 | 0.989 | 0.008 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-744-5p | 8.8263 | 8.237 | 8.4523 | 8.5915 | 8.0088 | 8.435 | 8.021 | 8.0215 | 8.7083 | 9.0758 | 8.2271 | 0.9706 | 0.989 | 0.0084 |
| hsa-miR-1257 | 8.2607 | 8.085 | 8.142 | 8.3647 | 8.0854 | 7.8811 | 8.0437 | 8.228 | 8.529 | 8.8455 | 7.5453 | 0.9658 | 0.9889 | 0.0088 |
| hsa-miR-670 | 8.4497 | 8.1301 | 8.3055 | 8.8762 | 7.6198 | 8.2572 | 8.173 | 7.9299 | 8.4188 | 8.8175 | 8.0047 | 0.9703 | 0.989 | 0.0094 |
| hsa-miR-219-1-3p | 8.8263 | 8.6623 | 9.1563 | 8.8102 | 8.751 | 8.8342 | 8.673 | 8.4085 | 8.0563 | 9.3545 | 8.6607 | 0.9517 | 0.9888 | 0.01 |
| hsa-miR-1323 | 8.9918 | 8.085 | 8.8731 | 8.8976 | 8.315 | 8.9558 | 8.6584 | 8.228 | 8.6314 | 9.0519 | 8.2082 | 0.9659 | 0.9889 | 0.0102 |
| hsa-miR-552 | 8.4497 | 7.7516 | 8.1985 | 8.2364 | 8.1101 | 8.2572 | 7.6286 | 7.9992 | 8.4639 | 8.5713 | 7.9145 | 0.9574 | 0.9888 | 0.0102 |
| hsa-miR-188-5p | 9.9477 | 9.6776 | 9.9738 | 10.0955 | 9.6198 | 10.02 | 9.6361 | 9.6212 | 10.1489 | 10.0992 | 9.5823 | 0.9364 | 0.9886 | 0.0116 |
| hsa-miR-1976 | 7.4748 | 7.3932 | 7.2529 | 7.2024 | 7.0349 | 7.7188 | 6.3656 | 7.3211 | 7.4859 | 7.5374 | 7.1302 | 0.9571 | 0.9888 | 0.0118 |
| hsa-miR-449c-5p | 8.8647 | 8.4653 | 8.668 | 8.8976 | 8.4173 | 8.435 | 8.4012 | 8.3742 | 8.8509 | 9.6528 | 8.1891 | 0.9615 | 0.9888 | 0.012 |
| hsa-miR-885-3p | 8.5237 | 8.2575 | 8.5425 | 8.5381 | 8.0854 | 8.3265 | 8.1311 | 8.228 | 8.5913 | 9.0277 | 7.9603 | 0.9491 | 0.9889 | 0.012 |
| hsa-miR-483-5p | 8.4748 | 8.1521 | 8.226 | 7.7643 | 7.0854 | 8.1338 | 7.6286 | 7.2471 | 8.4415 | 8.73 | 7.3866 | 0.9716 | 0.989 | 0.0126 |
| hsa-miR-940 | 7.8647 | 7.3557 | 7.0831 | 7.454 | 7.3974 | 7.3709 | 7.2136 | 6.8571 | 7.7991 | 8.3545 | 6.9144 | 0.963 | 0.9889 | 0.0127 |
| hsa-miR-190b | 7.571 | 6.8083 | 7.6274 | 7.3951 | 6.3975 | 7.2807 | 6.9979 | 6.8571 | 7.2489 | 7.5374 | 6.9603 | 0.9626 | 0.9889 | 0.0128 |
| hsa-miR-634 | 7.6168 | 7.6623 | 7.331 | 8.2025 | 7.3568 | 7.8501 | 7.9017 | 7.5227 | 8.114 | 8.145 | 7.3866 | 0.9522 | 0.9888 | 0.0139 |
| hsa-miR-619 | 7.2607 | 7.5996 | 7.8904 | 7.7643 | 7.3974 | 7.8811 | 7.436 | 6.906 | 8.114 | 7.7889 | 7.2823 | 0.9479 | 0.9887 | 0.0145 |
| hsa-miR-1302 | 7.9744 | 7.534 | 7.8904 | 7.8976 | 7.7511 | 7.5359 | 7.2916 | 7.4586 | 8.1964 | 8.5713 | 7.7152 | 0.9477 | 0.9887 | 0.0147 |
| hsa-miR-3614-5p | 8.4497 | 8.2575 | 8.405 | 8.3337 | 7.437 | 8.3488 | 8.0881 | 8.1285 | 7.8678 | 8.7889 | 7.7417 | 0.949 | 0.9888 | 0.0159 |
| hsa-miR-519c-3p | 8.3981 | 7.6927 | 7.9899 | 7.5106 | 7.7193 | 8.0269 | 7.7441 | 7.643 | 7.9334 | 8.6369 | 7.0896 | 0.9506 | 0.9888 | 0.0165 |
| hsa-miR-548ad | 9.5116 | 9.1846 | 9.5961 | 9.705 | 9.1582 | 9.2213 | 9.2035 | 9.2471 | 9.727 | 9.9779 | 9.11 | 0.9289 | 0.9885 | 0.0166 |
| hsa-miR-3182 | 8.4242 | 7.8626 | 8.3808 | 8.717 | 8.1817 | 8.3265 | 8.3656 | 8.0215 | 8.1695 | 8.9524 | 7.9376 | 0.9328 | 0.9886 | 0.0177 |
| hsa-miR-654-5p | 9.0282 | 8.1301 | 8.226 | 8.0956 | 8.2275 | 8.5553 | 8.1098 | 7.643 | 8.2489 | 8.5713 | 8.0896 | 0.911 | 0.9883 | 0.0177 |
| hsa-miR-1298 | 8.8647 | 8.0385 | 8.4981 | 8.5915 | 8.2719 | 8.6303 | 8.173 | 7.7805 | 8.9651 | 9.145 | 8.11 | 0.9493 | 0.9888 | 0.0179 |
| hsa-miR-4431 | 8.8647 | 7.9151 | 8.4523 | 8.1677 | 8.0088 | 8.3265 | 8.173 | 8.0866 | 8.5501 | 8.7889 | 8.0047 | 0.9382 | 0.9886 | 0.0181 |
| hsa-miR-920 | 7.8262 | 7.6313 | 7.5856 | 7.5106 | 7.6538 | 7.4557 | 7.47 | 7.2846 | 7.901 | 8.145 | 7.4838 | 0.9032 | 0.9882 | 0.0181 |
| hsa-miR-331-5p | 8.2315 | 7.9406 | 8.4981 | 7.9394 | 7.928 | 7.684 | 7.825 | 7.9534 | 8.4639 | 8.9264 | 7.9145 | 0.9362 | 0.9886 | 0.0182 |
| hsa-miR-519e-3p | 8.7461 | 8.4828 | 9.0679 | 7.7643 | 8.0854 | 8.8342 | 8.4012 | 7.9534 | 8.6895 | 9.003 | 8.2271 | 0.9382 | 0.9886 | 0.0188 |
| hsa-miR-570-3p | 9.571 | 9.7151 | 9.5749 | 9.9599 | 9.6025 | 9.7777 | 9.651 | 9.5766 | 9.7991 | 10.2536 | 8.9376 | 0.924 | 0.9884 | 0.0188 |
| hsa-miR-1273g-5p | 8.0762 | 7.9151 | 8.1705 | 7.3951 | 7.3974 | 9.7703 | 7.436 | 7.5841 | 7.9651 | 8.4304 | 7.2456 | 0.9395 | 0.9886 | 0.0189 |
| hsa-miR-521 | 8.2018 | 7.7536 | 8.0216 | 7.7643 | 7.3568 | 7.7527 | 7.7161 | 7.5227 | 8.0563 | 8.5026 | 7.2456 | 0.9326 | 0.9886 | 0.0199 |
| hsa-miR-562 | 8.1714 | 7.1078 | 8.253 | 8.643 | 7.3974 | 7.5932 | 7.6584 | 7.6996 | 8.8678 | 8.6686 | 7.2823 | 0.9538 | 0.9888 | 0.0206 |
| hsa-miR-555 | 6.7867 | 6.5671 | 7.1985 | 7.2696 | 6.6199 | 8.435 | 6.3656 | 6.0866 | 8.114 | 8.2325 | 6.4197 | 0.9538 | 0.9888 | 0.0211 |
| hsa-miR-889 | 7.7461 | 7.7225 | 7.9575 | 7.7643 | 7.1817 | 6.85 | 7.6584 | 7.3915 | 8.0265 | 8.0992 | 7.2823 | 0.9101 | 0.9883 | 0.0222 |
| hsa-miR-645 | 8.6612 | 8.0619 | 8.3055 | 7.9394 | 8.0604 | 7.4557 | 8.2916 | 7.8065 | 8.5708 | 8.4304 | 7.7152 | 0.906 | 0.9882 | 0.0231 |
| hsa-miR-526b-5p | 7.5237 | 7.1078 | 7.8557 | 7.7643 | 7.7511 | 7.5359 | 7.1729 | 7.0906 | 7.9962 | 8.6044 | 7.2456 | 0.9368 | 0.9886 | 0.0237 |
| hsa-miR-1303 | 8.1404 | 8.0146 | 8.253 | 8.3951 | 8.2048 | 8.0814 | 7.9506 | 7.5227 | 8.5913 | 9.0758 | 7.8429 | 0.9226 | 0.9884 | 0.0241 |
| hsa-miR-4647 | 8.7666 | 8.1738 | 8.2795 | 8.643 | 8.1344 | 8.0814 | 8.2531 | 8.1077 | 8.8166 | 8.9779 | 8.0047 | 0.906 | 0.9882 | 0.0259 |
| hsa-miR-122-5p | 7.8262 | 7.9151 | 7.8904 | 7.2024 | 6.5494 | 7.2333 | 7.47 | 6.9534 | 7.9651 | 7.73 | 7.3526 | 0.9346 | 0.9886 | 0.026 |
| hsa-miR-301b | 8.2607 | 7.7536 | 8.8019 | 8.5915 | 8.1101 | 8.5932 | 7.6584 | 8.0653 | 8.8678 | 9.0992 | 8.3001 | 0.9105 | 0.9883 | 0.029 |
| hsa-miR-2278 | 8.2607 | 8.534 | 8.4288 | 8.3647 | 7.9554 | 8.435 | 8.0437 | 7.4911 | 8.529 | 8.7889 | 7.5453 | 0.9062 | 0.9882 | 0.0303 |
| hsa-miR-142-5p | 8.2607 | 7.8357 | 8.1128 | 8.5381 | 8.8714 | 8.3265 | 8.2725 | 7.8321 | 8.4639 | 8.6686 | 7.7152 | 0.8786 | 0.9879 | 0.0311 |
| hsa-miR-641 | 8.4994 | 8.0146 | 8.405 | 8.5381 | 8.3974 | 8.3926 | 7.9506 | 8.1077 | 8.8339 | 8.9264 | 8.0688 | 0.8666 | 0.9877 | 0.0312 |
| hsa-miR-1248 | 8.1087 | 7.7802 | 8.331 | 7.9394 | 7.6869 | 7.9115 | 7.7161 | 6.9534 | 7.9651 | 8.393 | 7.6882 | 0.9346 | 0.9886 | 0.0314 |
| hsa-miR-876-3p | 8.8066 | 8.5172 | 9.0217 | 9.0956 | 8.7973 | 8.7015 | 7.6584 | 8.0653 | 8.8678 | 9.6686 | 8.4522 | 0.8736 | 0.9878 | 0.0329 |
| hsa-miR-515-5p | 9.4242 | 8.4288 | 8.7835 | 9.0581 | 8.7973 | 8.8811 | 8.5515 | 7.4911 | 8.529 | 9.145 | 8.5897 | 0.8784 | 0.9878 | 0.033 |
| hsa-miR-513b | 7.6612 | 7.2371 | 7.1985 | 7.3951 | 6.6199 | 7.1338 | 6.5673 | 7.0435 | 7.6115 | 7.9524 | 6.8183 | 0.9011 | 0.9882 | 0.0345 |
| hsa-miR-643 | 7.9388 | 8.0619 | 8.405 | 8.0956 | 8.1101 | 8.0269 | 9.7744 | 7.3568 | 8.3723 | 8.9524 | 7.8429 | 0.8861 | 0.988 | 0.0347 |
| hsa-miR-302e | 8.9022 | 8.1521 | 8.941 | 8.7409 | 8.315 | 8.6303 | 8.5672 | 8.4421 | 8.7453 | 8.9779 | 8.0896 | 0.8667 | 0.9877 | 0.0348 |
| hsa-miR-153 | 8.2315 | 7.9904 | 8.253 | 8.3647 | 8.1101 | 7.9115 | 7.9744 | 7.8065 | 8.4188 | 8.6686 | 8.1501 | 0.8217 | 0.987 | 0.035 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-378f | 8.4994 | 7.6623 | 8.331 | 7.8976 | 7.6198 | 7.9703 | 7.6286 | 7.906 | 8.0265 | 8.5026 | 7.7677 | 0.875 | 0.9878 | 0.0351 |
| hsa-miR-558 | 8.5476 | 8.2163 | 8.4981 | 8.5381 | 8.0349 | 8.2334 | 8.173 | 8.189 | 8.2489 | 9.0992 | 8.0478 | 0.8557 | 0.9875 | 0.0351 |
| hsa-miR-526a + hsa-miR-520c-5p + hsa-miR-518d-5p | 8.4242 | 7.8082 | 7.9575 | 8.2025 | 7.437 | 7.9412 | 7.6876 | 7.6716 | 8.0854 | 8.1894 | 8.0047 | 0.8561 | 0.9875 | 0.0359 |
| hsa-miR-524-3p | 8.7666 | 8.1952 | 7.9575 | 8.6175 | 7.8999 | 8.3926 | 7.9506 | 8.2086 | 8.4188 | 8.8455 | 7.6882 | 0.8819 | 0.9879 | 0.0366 |
| hsa-miR-631 | 9.4497 | 9.3269 | 9.5093 | 9.9187 | 9.2048 | 9.2807 | 9.41 | 9.417 | 9.6014 | 9.9905 | 8.9715 | 0.8464 | 0.9874 | 0.0367 |
| hsa-miR-202-3p | 7.7867 | 7.6623 | 7.9899 | 7.8301 | 7.8999 | 7.7859 | 7.0881 | 7.6716 | 8.4188 | 8.1894 | 7.6041 | 0.8595 | 0.9876 | 0.0368 |
| hsa-miR-127-5p | 8.1404 | 7.5672 | 7.668 | 7.5651 | 7.4754 | 7.5744 | 7.3291 | 7.3211 | 8.0563 | 8.315 | 7.2823 | 0.8676 | 0.9877 | 0.0369 |
| hsa-miR-612 | 9.1714 | 8.822 | 9.1128 | 9.7759 | 9.0978 | 9.2091 | 8.9263 | 8.6857 | 9.3364 | 9.9652 | 8.3056 | 0.8833 | 0.9879 | 0.0371 |
| hsa-miR-548h-5p | 8.3172 | 7.5001 | 8.0527 | 7.8546 | 7.7193 | 7.7188 | 7.5983 | 7.3915 | 8.114 | 8.467 | 7.8183 | 0.8626 | 0.9876 | 0.0375 |
| hsa-miR-548m | 7.7867 | 7.534 | 7.9899 | 7.8976 | 7.7821 | 7.6484 | 7.1729 | 7.8572 | 8.4188 | 8.145 | 7.3179 | 0.8616 | 0.9876 | 0.038 |
| hsa-miR-105-5p | 8.6612 | 8.1077 | 8.1985 | 8.3337 | 8.0088 | 8.0814 | 8.2335 | 8.339 | 8.2489 | 8.4304 | 8.0047 | 0.774 | 0.9862 | 0.039 |
| hsa-miR-486-3p | 8.4497 | 7.7516 | 8.0216 | 8.2025 | 7.7821 | 8.054 | 7.7716 | 7.4911 | 8.3957 | 8.6686 | 7.6327 | 0.8681 | 0.9877 | 0.0391 |
| hsa-miR-320d | 8.5476 | 8.3557 | 9.3054 | 8.5106 | 8.437 | 8.5359 | 8.2136 | 8.4421 | 8.7453 | 8.9779 | 8.6327 | 0.849 | 0.9874 | 0.04 |
| hsa-miR-648 | 8.2892 | 7.8626 | 7.7076 | 8.302 | 7.7821 | 7.684 | 8.0437 | 7.7805 | 8.1964 | 8.315 | 7.7607 | 0.8116 | 0.9869 | 0.042 |
| hsa-miR-891a | 9.0431 | 8.6156 | 8.9575 | 9.15 | 8.7032 | 8.7188 | 8.7302 | 8.569 | 9.236 | 9.5201 | 8.3353 | 0.8431 | 0.9874 | 0.0423 |
| hsa-miR-1910 | 7.2017 | 7.0147 | 7.1985 | 7.3337 | 6.8125 | 7.2333 | 6.6286 | 6.9992 | 7.4859 | 7.467 | 6.6042 | 0.8236 | 0.9871 | 0.0425 |
| hsa-miR-584-5p | 7.7461 | 7.534 | 7.9575 | 7.5106 | 8.1101 | 7.7859 | 7.47 | 7.6716 | 8.0563 | 7.8455 | 7.5453 | 0.7781 | 0.9863 | 0.0426 |
| hsa-miR-642a-5p | 8.0091 | 7.6313 | 7.668 | 7.5651 | 7.4754 | 6.9115 | 7.5355 | 7.3211 | 8.0563 | 8.8455 | 7.0896 | 0.8925 | 0.988 | 0.0432 |
| hsa-miR-302d-3p | 10.5652 | 10.1685 | 10.6118 | 11.2406 | 10.4024 | 10.7188 | 10.5072 | 10.266 | 10.6461 | 11.2272 | 9.9603 | 0.8662 | 0.9877 | 0.0434 |
| hsa-miR-1203 | 8.4748 | 8.2777 | 8.226 | 8.5381 | 8.1101 | 8.3488 | 7.825 | 8.1285 | 8.3242 | 9.0992 | 7.9603 | 0.831 | 0.9873 | 0.0444 |
| hsa-miR-520c-3p | 8.2892 | 7.7225 | 7.8557 | 7.9394 | 7.437 | 7.8183 | 7.7716 | 7.5841 | 8.0854 | 8.145 | 7.4197 | 0.8101 | 0.9868 | 0.0447 |
| hsa-miR-592 | 8.1714 | 7.8891 | 8.0831 | 8.454 | 7.7511 | 7.9703 | 7.6584 | 8.0215 | 8.1964 | 8.5026 | 7.7932 | 0.7953 | 0.9866 | 0.046 |
| hsa-miR-3200-3p | 7.4242 | 7.5001 | 6.9576 | 7.1321 | 7.1344 | 6.7188 | 7.1311 | 7.3915 | 7.2489 | 7.7889 | 6.8183 | 0.8107 | 0.9869 | 0.0468 |
| hsa-miR-548ae | 8.3172 | 8.6623 | 8.7076 | 7.9394 | 8.2275 | 8.5359 | 8.1311 | 8.0436 | 8.2229 | 8.5713 | 7.7932 | 0.7914 | 0.9865 | 0.048 |
| hsa-miR-1538 | 8.2018 | 7.9406 | 8.142 | 8.058 | 7.6538 | 8.0544 | 7.7986 | 7.4911 | 8.0563 | 8.5026 | 7.7793 | 0.7762 | 0.9863 | 0.0499 |
| hsa-miR-4451 | 8.4748 | 7.6623 | 8.5205 | 8.0196 | 7.7193 | 7.8183 | 7.2916 | 7.8321 | 8.4639 | 8.6996 | 8.0688 | 0.8586 | 0.9876 | 0.0502 |
| hsa-miR-934 | 7.9388 | 7.3932 | 8.0216 | 7.3337 | 7.2718 | 7.8501 | 7.2531 | 7.4911 | 7.9962 | 7.7889 | 6.8672 | 0.8347 | 0.9872 | 0.0507 |
| hsa-miR-302a-3p | 8.9744 | 8.6623 | 8.941 | 9.1139 | 8.5494 | 8.6119 | 8.436 | 8.8193 | 8.9493 | 9.5544 | 8.4032 | 0.8032 | 0.9867 | 0.0525 |
| hsa-miR-624-3p | 8.2018 | 7.7516 | 8.2795 | 8.4826 | 8.2275 | 8.0269 | 7.7161 | 7.4586 | 8.7635 | 8.73 | 7.9376 | 0.8321 | 0.9872 | 0.0547 |
| hsa-miR-639 | 8.0091 | 7.8626 | 8.0216 | 7.7643 | 7.7821 | 7.9412 | 7.3291 | 7.9992 | 8.142 | 7.8999 | 7.6882 | 0.6856 | 0.9845 | 0.0547 |
| hsa-miR-621 | 8.5941 | 8.2777 | 8.4288 | 8.454 | 8.0349 | 8.2572 | 7.9744 | 7.9764 | 8.486 | 9.0277 | 8.0896 | 0.7767 | 0.9863 | 0.056 |
| hsa-miR-551a | 7.7461 | 8.2976 | 8.226 | 8.2696 | 7.928 | 7.9703 | 8.1934 | 8.7321 | 8.486 | 8.9779 | 7.9603 | 0.8015 | 0.9867 | 0.0568 |
| hsa-miR-320c | 8.8066 | 8.5835 | 8.4981 | 8.7409 | 8.585 | 8.6663 | 8.173 | 8.2086 | 9.0114 | 9.0519 | 8.4032 | 0.7452 | 0.9857 | 0.0571 |
| hsa-miR-578 | 8.7461 | 7.9657 | 8.6879 | 8.5381 | 8.1582 | 8.1594 | 8.1311 | 8.303 | 8.7991 | 8.8175 | 7.9603 | 0.7932 | 0.9866 | 0.0575 |
| hsa-miR-217 | 7.3172 | 7.3172 | 7.142 | 7.5106 | 7.2718 | 7.1338 | 7.3291 | 7.1285 | 7.3485 | 7.5374 | 7.0478 | 0.5608 | 0.9811 | 0.0576 |
| hsa-miR-1227 | 7.5237 | 8.0146 | 7.9575 | 8.0196 | 7.3568 | 7.4557 | 7.4012 | 7.5227 | 7.9962 | 8.467 | 7.4521 | 0.7991 | 0.9867 | 0.0586 |
| hsa-miR-492 | 8.0431 | 7.3932 | 7.9243 | 7.8101 | 7.2275 | 7.3709 | 7.47 | 7.3568 | 7.9334 | 8.2743 | 7.3179 | 0.7985 | 0.9867 | 0.0591 |
| hsa-miR-1275 | 8.7666 | 8.6156 | 8.8556 | 8.8102 | 8.1101 | 8.5744 | 8.4699 | 8.3567 | 8.7083 | 9.2325 | 8.0896 | 0.781 | 0.9864 | 0.0597 |
| hsa-miR-1225-3p | 8.0091 | 7.6927 | 7.9243 | 7.5651 | 7.2275 | 7.8501 | 7.5673 | 7.3211 | 7.9962 | 8.003 | 7.0047 | 0.7868 | 0.9865 | 0.06 |
| hsa-miR-219-2-3p | 8.4748 | 7.8357 | 8.1985 | 8.1677 | 7.5129 | 7.5744 | 7.5673 | 7.643 | 8.4639 | 8.6996 | 7.9145 | 0.8205 | 0.987 | 0.0608 |
| hsa-miR-548q | 8.0091 | 7.9151 | 8.8379 | 8.3951 | 7.7511 | 8.4964 | 7.9744 | 7.9992 | 8.5076 | 8.003 | 7.7417 | 0.8 | 0.9867 | 0.0613 |
| hsa-miR-3605-5p | 8.4748 | 8.2976 | 8.5856 | 8.6928 | 8.2719 | 8.5359 | 8.3105 | 8.491 | 8.5708 | 8.7597 | 8.2641 | 0.6687 | 0.9841 | 0.0616 |
| hsa-miR-1202 | 9.0925 | 8.6623 | 8.746 | 8.8545 | 8.4754 | 8.4762 | 8.6436 | 8.7406 | 9.1558 | 9.4118 | 8.0478 | 0.7933 | 0.9866 | 0.0618 |
| hsa-miR-516a-5p | 9.2462 | 8.9781 | 9.3183 | 9.2531 | 9.3255 | 9.1466 | 9.0549 | 8.4918 | 9.5605 | 9.6528 | 8.8183 | 0.721 | 0.9852 | 0.0619 |
| hsa-miR-298 | 8.3172 | 7.6927 | 8.331 | 8.1677 | 7.9554 | 8.1078 | 7.0881 | 8.0215 | 8.6314 | 8.73 | 7.6041 | 0.8306 | 0.9872 | 0.0623 |
| hsa-miR-548a-3p | 8.9918 | 8.8357 | 9.2124 | 9.2195 | 8.585 | 8.684 | 8.5515 | 8.7674 | 9.3604 | 9.3349 | 8.7416 | 0.7461 | 0.9857 | 0.0623 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-2052 | 8.571 | 8.1952 | 8.3561 | 8.3951 | 7.9824 | 7.9412 | 8.066 | 7.8572 | 8.8509 | 8.8175 | 7.8911 | 0.7791 | 0.9863 | 0.0626 |
| hsa-miR-103a-3p | 7.8647 | 7.2371 | 7.668 | 7.454 | 7.0349 | 7.7188 | 6.9506 | 6.7541 | 7.7635 | 8.2325 | 6.9144 | 0.8312 | 0.9872 | 0.0628 |
| hsa-miR-632 | 8.1714 | 8.237 | 8.668 | 8.454 | 7.8714 | 8.0269 | 8.2335 | 6.9896 | 8.7635 | 8.7597 | 7.8183 | 0.7899 | 0.9865 | 0.0634 |
| hsa-miR-490-3p | 7.8647 | 7.534 | 8.142 | 7.6175 | 7.1344 | 7.684 | 7.2916 | 7.1285 | 8.142 | 8.2325 | 7.0896 | 0.8161 | 0.9869 | 0.0638 |
| hsa-miR-496 | 8.3981 | 7.7516 | 8.5425 | 8.1321 | 7.5129 | 7.9412 | 7.7716 | 7.8572 | 8.486 | 8.3545 | 7.6041 | 0.7928 | 0.9866 | 0.065 |
| hsa-miR-1304-5p | 8.4242 | 7.6927 | 8.0527 | 7.6175 | 7.7193 | 7.6484 | 7.6286 | 8.0265 | 8.0265 | 8.8455 | 7.6041 | 0.8135 | 0.9869 | 0.0654 |
| hsa-miR-373-3p | 7.4748 | 6.8627 | 7.6274 | 6.717 | 6.3975 | 6.7859 | 6.851 | 6.1691 | 7.6115 | 7.315 | 6.9603 | 0.8326 | 0.9872 | 0.0671 |
| hsa-miR-548f | 8.0091 | 7.3932 | 7.668 | 7.6175 | 7.2718 | 7.684 | 7.2531 | 7.0866 | 8.2744 | 7.8455 | 7.0047 | 0.7854 | 0.9864 | 0.0672 |
| hsa-miR-1207-3p | 7.4242 | 7.5996 | 8.0216 | 6.98 | 7.3568 | 7.5744 | 7.0881 | 6.643 | 8.1695 | 8.0992 | 8.6672 | 0.8293 | 0.9871 | 0.0695 |
| hsa-miR-208a | 9.0091 | 8.3746 | 9.0217 | 8.8102 | 8.8274 | 8.9264 | 8.3105 | 8.2086 | 9.2229 | 9.3738 | 8.3697 | 0.7654 | 0.9861 | 0.0733 |
| hsa-miR-378g | 8.9918 | 9.1952 | 9.226 | 8.5915 | 8.1101 | 7.9989 | 7.7161 | 8.303 | 10.0265 | 10.4396 | 8.0047 | 0.8904 | 0.988 | 0.0748 |
| hsa-miR-599 | 8.3717 | 8.1952 | 8.4523 | 8.302 | 8.1582 | 8.3488 | 8.0437 | 7.6716 | 8.4188 | 8.8175 | 8.0264 | 0.676 | 0.9843 | 0.0748 |
| hsa-miR-544a | 8.6168 | 8.2163 | 8.4981 | 8.7409 | 8.1101 | 8.9114 | 7.9506 | 8.1077 | 8.2995 | 8.873 | 8.0264 | 0.7313 | 0.9854 | 0.075 |
| hsa-miR-369-5p | 8.1087 | 7.3932 | 8.0831 | 7.5651 | 7.437 | 7.7527 | 7.7161 | 7.0435 | 7.8678 | 8.1894 | 7.2823 | 0.7513 | 0.9858 | 0.0754 |
| hsa-miR-658 | 8.9918 | 8.766 | 9.0527 | 8.8325 | 8.6869 | 8.7859 | 8.5031 | 8.4085 | 9.2097 | 9.1894 | 8.6468 | 0.6421 | 0.9835 | 0.0754 |
| hsa-miR-649 | 7.571 | 7.3557 | 7.7835 | 7.454 | 7.3974 | 7.6118 | 6.7986 | 7.3211 | 8.114 | 7.6044 | 7.1697 | 0.7153 | 0.9851 | 0.0757 |
| hsa-miR-144-3p | 10.571 | 11.2293 | 10.9616 | 10.6928 | 10.1284 | 10.2453 | 9.8052 | 10.1025 | 11.4188 | 11.821 | 10.4441 | 0.8423 | 0.9873 | 0.0771 |
| hsa-miR-548e | 8.3981 | 7.5001 | 8.226 | 8.2025 | 8.0349 | 7.8501 | 7.7441 | 7.4911 | 8.6115 | 8.7597 | 7.5149 | 0.7849 | 0.9864 | 0.0771 |
| hsa-miR-514a-3p | 8.1714 | 7.7904 | 8.1128 | 8.4826 | 7.3568 | 8.9264 | 8.3105 | 8.3211 | 8.0563 | 8.6044 | 7.6607 | 0.7724 | 0.9862 | 0.0785 |
| hsa-miR-515-3p | 8.5237 | 7.7516 | 7.8904 | 8.454 | 7.7193 | 7.4557 | 7.5673 | 7.9534 | 8.3242 | 8.6996 | 7.575 | 0.7618 | 0.986 | 0.0785 |
| hsa-miR-4531 | 8.9744 | 8.2575 | 8.7076 | 8.8102 | 7.7821 | 7.6118 | 7.7716 | 8.303 | 8.6115 | 9.145 | 7.7417 | 0.7881 | 0.9865 | 0.0793 |
| hsa-miR-1306-3p | 7.7042 | 7.062 | 7.2529 | 7.2024 | 7.0349 | 8.4139 | 8.3474 | 6.6996 | 7.5708 | 8.0519 | 6.4838 | 0.8423 | 0.9863 | 0.08 |
| hsa-miR-548ag | 8.4748 | 8.4828 | 8.4288 | 8.565 | 7.9554 | 7.3709 | 6.851 | 8.1077 | 8.529 | 9.0519 | 7.7932 | 0.713 | 0.9851 | 0.0804 |
| hsa-miR-514b-5p | 8.5237 | 8.5172 | 8.82 | 9.1321 | 8.8274 | 8.2807 | 8.0437 | 8.6857 | 8.7635 | 9.3149 | 7.9145 | 0.7169 | 0.9852 | 0.0815 |
| hsa-miR-485-5p | 8.5941 | 8.2575 | 8.331 | 8.302 | 7.8124 | 8.8183 | 8.5983 | 8.7065 | 8.5913 | 8.8999 | 8.8672 | 0.7566 | 0.9859 | 0.0828 |
| hsa-miR-198 | 8.4994 | 7.5672 | 8.0831 | 8.2025 | 7.1817 | 8.3037 | 7.7161 | 7.2086 | 8.2489 | 7.9524 | 7.0047 | 0.713 | 0.9851 | 0.0841 |
| hsa-miR-1229 | 7.8262 | 7.9406 | 8.4288 | 7.5106 | 7.4754 | 7.9115 | 7.436 | 7.4586 | 8.0563 | 9.0519 | 7.7932 | 0.7535 | 0.9859 | 0.083 |
| hsa-miR-1288 | 8.571 | 8.1077 | 8.405 | 8.6175 | 8.0088 | 8.4557 | 7.6876 | 7.9299 | 8.4639 | 9.0519 | 7.7932 | 0.7535 | 0.9859 | 0.083 |
| hsa-miR-548ak | 8.8456 | 8.2575 | 8.3055 | 8.4248 | 7.6198 | 8.3488 | 8.8766 | 7.906 | 8.7269 | 8.4304 | 7.8911 | 0.7459 | 0.9857 | 0.0839 |
| hsa-miR-762 | 8.1714 | 7.9151 | 7.7076 | 8.565 | 8.0349 | 7.7527 | 8.2335 | 8.228 | 7.9651 | 8.5026 | 8.0047 | 0.6023 | 0.9824 | 0.0839 |
| hsa-miR-3190-5p | 8.1404 | 7.8891 | 8.0216 | 8.302 | 7.8124 | 8.2091 | 7.2916 | 7.6716 | 8.0854 | 8.145 | 9.3149 | 0.6515 | 0.9837 | 0.0841 |
| hsa-miR-198 | 8.4994 | 8.2575 | 8.0216 | 8.2025 | 7.1817 | 7.9115 | 7.6286 | 7.4586 | 8.2489 | 8.4304 | 8.0047 | 0.7614 | 0.986 | 0.0854 |
| hsa-miR-1262 | 8.4242 | 7.8891 | 8.3561 | 7.8101 | 7.585 | 8.2572 | 7.7441 | 7.6996 | 8.4415 | 7.7889 | 7.6327 | 0.6973 | 0.9847 | 0.0856 |
| hsa-miR-873-5p | 7.5237 | 7.5672 | 7.5856 | 7.8101 | 7.5494 | 7.6484 | 7.1311 | 7.4254 | 7.727 | 8.1894 | 7.0047 | 0.6561 | 0.9838 | 0.0862 |
| hsa-miR-449a | 8.8263 | 8.4653 | 8.7649 | 8.565 | 8.4754 | 8.6303 | 8.066 | 8.3742 | 8.7635 | 9.0277 | 8.3353 | 0.6017 | 0.9824 | 0.0865 |
| hsa-miR-942 | 8.5476 | 8.2976 | 8.3055 | 8.717 | 8.1582 | 8.7527 | 8.1311 | 8.1077 | 8.3484 | 8.5026 | 8.0688 | 0.5751 | 0.9816 | 0.0866 |
| hsa-miR-770-5p | 8.6612 | 8.3746 | 8.5856 | 7.9394 | 8.0604 | 8.6119 | 8.1098 | 8.0653 | 8.5076 | 8.9779 | 7.891 | 0.6669 | 0.9841 | 0.0888 |
| hsa-miR-125a-3p | 8.7867 | 8.1077 | 8.4754 | 7.9394 | 7.928 | 7.7859 | 7.8511 | 8.3915 | 8.901 | 8.5026 | 7.5149 | 0.749 | 0.9858 | 0.0896 |
| hsa-miR-623 | 6.9388 | 7.4653 | 7.2529 | 7.2024 | 6.9279 | 7.2333 | 6.7986 | 6.906 | 7.1964 | 7.6686 | 6.6042 | 0.6409 | 0.9834 | 0.0896 |
| hsa-miR-642b-3p | 7.571 | 7.3557 | 8.5642 | 6.8976 | 6.6869 | 7.1845 | 7.0881 | 7.1691 | 7.142 | 7.315 | 6.6042 | 0.6558 | 0.9838 | 0.0896 |
| hsa-miR-924 | 9.0762 | 8.4653 | 8.8556 | 8.7874 | 8.1582 | 8.3488 | 8.3291 | 8.5383 | 8.9961 | 9.0992 | 8.1501 | 0.6938 | 0.9847 | 0.0916 |
| hsa-miR-1252 | 9.2167 | 8.6776 | 9.1128 | 9.0581 | 8.5673 | 8.85 | 8.4187 | 8.5991 | 9.0854 | 9.6842 | 8.3697 | 0.7107 | 0.985 | 0.092 |
| hsa-miR-149-5p | 9.385 | 8.8492 | 8.9244 | 9.1139 | 9.0477 | 9.1845 | 9.0881 | 8.7541 | 8.8678 | 9.4849 | 8.4522 | 0.6104 | 0.9826 | 0.0921 |
| hsa-miR-518a-3p | 8.0091 | 7.8082 | 8.3055 | 8.3951 | 7.7193 | 8.1338 | 7.5983 | 7.7541 | 8.142 | 8.9779 | 7.9145 | 0.5937 | 0.9821 | 0.0921 |
| hsa-miR-548am-3p | 8.9206 | 8.2976 | 8.4981 | 8.8325 | 8.1817 | 8.5744 | 8.2725 | 8.303 | 8.1695 | 9.2111 | 8.1891 | 0.68 | 0.9844 | 0.0928 |
| hsa-miR-431-5p | 8.3981 | 8.4116 | 8.8731 | 8.3647 | 8.2499 | 8.4964 | 8.1098 | 7.906 | 8.3242 | 9.0758 | 8.2822 | 0.6446 | 0.9835 | 0.0938 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-224-5p | 8.3172 | 7.7516 | 7.9243 | 7.6681 | 7.7821 | 7.9703 | 7.3656 | 7.7271 | 8.114 | 8.2325 | 7.3526 | 0.6327 | 0.9832 | 0.095 |
| hsa-miR-383 | 9.2018 | 8.7225 | 8.6879 | 8.3647 | 8.2048 | 8.5359 | 8.1522 | 8.3742 | 8.7814 | 9.2325 | 8.1697 | 0.7013 | 0.9848 | 0.0953 |
| hsa-miR-588 | 8.1404 | 7.8082 | 8.0216 | 8.2025 | 7.585 | 7.7188 | 7.7161 | 7.4254 | 8.2229 | 8.5373 | 7.5149 | 0.661 | 0.9839 | 0.0956 |
| hsa-miR-608 | 8.0762 | 8.0619 | 8.331 | 8.2364 | 7.6538 | 7.5744 | 7.7716 | 7.906 | 8.486 | 8.6044 | 7.5149 | 0.678 | 0.9843 | 0.0956 |
| hsa-miR-1181 | 8.0762 | 8.0146 | 7.9575 | 8.058 | 8.0088 | 8.1078 | 7.7161 | 7.6996 | 8.3242 | 8.467 | 7.2456 | 0.6289 | 0.9831 | 0.0963 |
| hsa-miR-342-5p | 8.4497 | 8.2976 | 8.8379 | 8.5915 | 8.2719 | 8.3488 | 8.173 | 7.6996 | 9.0415 | 8.0896 | 8.0896 | 0.6987 | 0.9848 | 0.0971 |
| hsa-miR-1281 | 8.8836 | 8.5672 | 8.8019 | 9 | 8.1817 | 8.435 | 8.5983 | 8.5383 | 8.6704 | 9.145 | 8.1501 | 0.6334 | 0.9832 | 0.0973 |
| hsa-miR-597 | 8.2892 | 7.6927 | 7.8201 | 8.5106 | 7.4754 | 8.1594 | 7.7716 | 7.2846 | 8.0563 | 8.5026 | 7.3866 | 0.728 | 0.9854 | 0.0974 |
| hsa-miR-885-5p | 8.3447 | 8.2976 | 8.6479 | 8.3337 | 7.9824 | 8.4557 | 8.0437 | 7.8321 | 8.4639 | 8.6996 | 7.8429 | 0.6047 | 0.9825 | 0.0983 |
| hsa-miR-548o-3p | 8.1404 | 7.7802 | 8.331 | 8.058 | 7.7511 | 8.0269 | 7.6584 | 7.6139 | 8.3957 | 8.0992 | 7.6882 | 0.5729 | 0.9815 | 0.0984 |
| hsa-miR-1271-5p | 8.4242 | 8.0385 | 8.3561 | 8.2696 | 7.5494 | 7.8811 | 8.0437 | 7.7805 | 8.2744 | 8.393 | 7.7932 | 0.6153 | 0.9828 | 0.0999 |
| hsa-miR-551b-3p | 8.1714 | 8.2163 | 8.4288 | 7.9801 | 7.2718 | 7.5359 | 7.5673 | 7.3915 | 8.5913 | 8.7889 | 7.6041 | 0.7595 | 0.986 | 0.1005 |
| hsa-miR-589-5p | 7.9388 | 7.4653 | 8.1128 | 7.8976 | 7.7821 | 7.7859 | 7.6876 | 7.1691 | 7.9651 | 8.73 | 7.0896 | 0.7151 | 0.9851 | 0.1014 |
| hsa-miR-519b-5p + hsa-miR-519c-5p | 9.275 | 8.7516 | 9.0059 | 9.2859 | 8.8568 | 8.8963 | 8.6584 | 8.5383 | 9.3841 | 9.467 | 8.6468 | 0.6123 | 0.9827 | 0.1032 |
| hsa-miR-1470 | 8.8263 | 8.2575 | 8.7835 | 8.565 | 7.9824 | 8.2807 | 8.066 | 8.4085 | 8.5913 | 9.2111 | 7.7152 | 0.7006 | 0.9848 | 0.1041 |
| hsa-miR-1251 | 8.4748 | 7.9406 | 8.226 | 8.5915 | 7.928 | 8.1078 | 7.5983 | 8.0866 | 8.3723 | 8.73 | 8.8672 | 0.6284 | 0.9831 | 0.1052 |
| hsa-miR-210 | 9.1867 | 9.1846 | 9.405 | 8.7643 | 7.3974 | 8.5163 | 8.4163 | 9.1791 | 8.8509 | 9.1223 | 8.0047 | 0.804 | 0.9867 | 0.1056 |
| hsa-miR-1282 | 8.3717 | 8.3932 | 8.0216 | 7.9394 | 7.8999 | 8.0814 | 7.5983 | 7.8818 | 8.4639 | 8.4304 | 7.6607 | 0.5843 | 0.9819 | 0.1058 |
| hsa-miR-651 | 8.7461 | 8.5672 | 8.8904 | 8.7643 | 8.3974 | 8.5163 | 8.1522 | 8.4421 | 8.529 | 9.2535 | 8.4994 | 0.5497 | 0.9807 | 0.1077 |
| hsa-miR-409-5p | 8.3981 | 8.1952 | 7.8201 | 8.2364 | 7.6538 | 7.9989 | 8.8766 | 7.7541 | 8.0563 | 8.2325 | 7.7932 | 0.5141 | 0.9794 | 0.1088 |
| hsa-miR-647 | 9.0598 | 8.8746 | 9.0059 | 9.0196 | 8.8274 | 8.8022 | 8.2531 | 8.8321 | 9.2489 | 9.5201 | 8.3353 | 0.6213 | 0.9829 | 0.1094 |
| hsa-miR-450b-5p | 8.5941 | 8.3746 | 8.7835 | 8.643 | 7.8422 | 8.3265 | 8.0881 | 7.9534 | 8.5501 | 8.8999 | 8.2082 | 0.625 | 0.983 | 0.1098 |
| hsa-miR-600 | 8.4497 | 8.1077 | 8.5642 | 7.8976 | 7.8999 | 8.0544 | 7.9744 | 7.6139 | 8.4639 | 8.6686 | 7.6607 | 0.6282 | 0.9831 | 0.1112 |
| hsa-miR-5481 | 8.3981 | 8.4653 | 7.8201 | 8.4826 | 8.1338 | 8.1338 | 7.8511 | 7.906 | 8.2489 | 8.5713 | 7.7932 | 0.5864 | 0.9819 | 0.1116 |
| hsa-miR-488-3p | 8.3717 | 8.0146 | 8.5205 | 7.8546 | 8.7193 | 8.0269 | 7.436 | 7.6139 | 8.2489 | 8.6369 | 7.9376 | 0.6403 | 0.9834 | 0.1128 |
| hsa-miR-615-5p | 8.571 | 8.5996 | 8.6274 | 8.9801 | 8.315 | 8.5359 | 8.0881 | 8.4749 | 8.8339 | 9.2311 | 7.8911 | 0.6282 | 0.9831 | 0.1128 |
| hsa-miR-520a-5p | 8.3172 | 8.0619 | 8.0831 | 8.3337 | 8.0854 | 8.0544 | 7.6876 | 7.9764 | 8.142 | 8.8455 | 7.6607 | 0.5585 | 0.981 | 0.1152 |
| hsa-miR-1324 | 8.4497 | 7.7802 | 8.0527 | 8.454 | 8.8422 | 7.4964 | 7.9506 | 7.7541 | 8.2489 | 8.6369 | 7.9145 | 0.608 | 0.9825 | 0.1155 |
| hsa-miR-622 | 8.571 | 7.8626 | 8.226 | 8.0956 | 7.9824 | 7.8811 | 8.021 | 7.9299 | 8.114 | 8.73 | 7.5149 | 0.5835 | 0.9818 | 0.1157 |
| hsa-miR-888-5p | 8.8066 | 8.4653 | 8.8904 | 8.6175 | 8.5494 | 8.7527 | 8.3291 | 8.5537 | 8.7814 | 8.8999 | 7.9827 | 0.4925 | 0.9785 | 0.1159 |
| hsa-miR-548i | 8.7867 | 7.9406 | 8.142 | 8.6175 | 8.0088 | 8.7501 | 8.2531 | 7.643 | 8.6115 | 8.873 | 7.8672 | 0.6659 | 0.984 | 0.1162 |
| hsa-miR-944 | 7.9744 | 8.1521 | 7.9575 | 8.1321 | 7.585 | 7.5744 | 7.5673 | 7.5541 | 8.0265 | 8.5026 | 7.6327 | 0.5336 | 0.9802 | 0.1173 |
| hsa-miR-2117 | 9.0091 | 8.9279 | 8.9738 | 9.2696 | 8.6704 | 8.7359 | 8.7302 | 8.6574 | 8.901 | 9.3349 | 8.7547 | 0.4208 | 0.975 | 0.1178 |
| hsa-miR-520b | 8.7461 | 8.5172 | 8.5642 | 8.717 | 8.315 | 8.7188 | 8.2136 | 8.339 | 8.6314 | 8.9779 | 7.8429 | 0.539 | 0.9804 | 0.118 |
| hsa-miR-3187-3p | 8.2892 | 8.237 | 8.3561 | 8.302 | 7.9824 | 7.9989 | 8.8766 | 8.0215 | 8.2744 | 8.5373 | 7.9827 | 0.3514 | 0.9702 | 0.1181 |
| hsa-miR-1236 | 8.7253 | 8.4297 | 8.7835 | 8.0956 | 8.4754 | 8.3709 | 8.173 | 8.0653 | 8.9807 | 9.0519 | 7.6607 | 0.6537 | 0.9837 | 0.1182 |
| hsa-miR-561-3p | 8.5237 | 8.2163 | 8.4523 | 8.6681 | 7.8999 | 8.0814 | 8.1311 | 7.9992 | 8.5501 | 8.8999 | 7.7417 | 0.6002 | 0.9823 | 0.1182 |
| hsa-miR-545-3p | 8.1714 | 8.2575 | 8.3808 | 8.4248 | 7.928 | 7.5359 | 8.173 | 7.9299 | 8.2489 | 8.9524 | 7.8429 | 0.6003 | 0.9823 | 0.1187 |
| hsa-miR-499a-3p | 9.4497 | 9.119 | 9.3561 | 9.5516 | 8.6869 | 9.0814 | 9.1205 | 8.8695 | 9.2744 | 9.5544 | 8.7805 | 0.5522 | 0.9808 | 0.1192 |
| hsa-miR-554 | 8.1087 | 7.8891 | 7.9243 | 7.9801 | 7.3974 | 7.6484 | 7.5355 | 7.3915 | 8.142 | 8.2743 | 7.4521 | 0.5567 | 0.981 | 0.1193 |
| hsa-miR-4741 | 8.8066 | 8.5001 | 8.8019 | 8.8325 | 8.1582 | 8.5359 | 8.4187 | 8.1691 | 8.9807 | 9.0277 | 8.8672 | 0.6097 | 0.9826 | 0.12 |
| hsa-miR-760 | 8.3981 | 8.0385 | 8.3808 | 8.058 | 7.8999 | 8.1078 | 7.5673 | 7.8065 | 8.529 | 8.6369 | 7.5453 | 0.5888 | 0.982 | 0.1229 |
| hsa-miR-1911-5p | 8.5237 | 7.8357 | 8.1128 | 7.8546 | 7.8714 | 7.684 | 7.6584 | 7.8818 | 8.3242 | 8.467 | 7.4838 | 0.5681 | 0.9813 | 0.1231 |
| hsa-miR-2116-5p | 8.9206 | 9.0266 | 8.8556 | 8.8545 | 8.6704 | 9.0544 | 8.1522 | 8.7134 | 9.0265 | 9.2743 | 8.2271 | 0.5538 | 0.9809 | 0.1243 |
| hsa-miR-4485 | 8.2315 | 7.8082 | 7.9899 | 6.6175 | 6.3975 | 7.1845 | 7.2531 | 8.5721 | 6.9651 | 7.73 | 6.7152 | 0.7749 | 0.9863 | 0.1247 |
| hsa-miR-3131 | 8.9022 | 8.2777 | 8.6879 | 8.2025 | 8.0854 | 8.0544 | 8.1311 | 8.0215 | 8.6704 | 8.9779 | 7.9827 | 0.6007 | 0.9823 | 0.1248 |
| hsa-miR-512-5p | 8.8066 | 8.4476 | 7.8201 | 8.0956 | 7.7821 | 8.1338 | 8.1522 | 7.8065 | 8.4188 | 8.0992 | 7.7677 | 0.5812 | 0.9818 | 0.1274 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-656 | 9.5476 | 9.1952 | 9.6066 | 9.5915 | 8.969 | 9.1338 | 9.099 | 8.9534 | 9.4968 | 9.73 | 9.11 | 0.4849 | 0.9782 | 0.1281 |
| hsa-miR-320b | 8.2892 | 8.1738 | 8.3561 | 8.2696 | 8.0088 | 8.1844 | 8.0437 | 7.7805 | 8.4639 | 8.2325 | 7.8429 | 0.3198 | 0.9673 | 0.1282 |
| hsa-miR-1204 | 8.2892 | 8.1738 | 8.4754 | 8.454 | 8.1101 | 7.9703 | 7.9979 | 7.6716 | 8.5708 | 8.9524 | 8.8672 | 0.5638 | 0.9812 | 0.1288 |
| hsa-miR-628-3p | 9.0762 | 8.7943 | 8.7835 | 8.7409 | 8.437 | 8.8656 | 8.436 | 8.3567 | 8.9651 | 9.0519 | 8.1501 | 0.4992 | 0.9788 | 0.1288 |
| hsa-miR-572 | 8.0762 | 7.6313 | 7.9575 | 8.302 | 7.6198 | 8.8183 | 7.436 | 7.5841 | 8.0265 | 8.73 | 7.1302 | 0.634 | 0.9833 | 0.1298 |
| hsa-miR-323b-3p | 8.2315 | 7.7516 | 8.331 | 8.1677 | 8.1582 | 7.8183 | 7.825 | 8.0653 | 8.3957 | 8.5026 | 7.3179 | 0.5372 | 0.9803 | 0.1301 |
| hsa-miR-3161 | 8.1714 | 7.6623 | 8.4754 | 7.9801 | 7.7193 | 7.9703 | 7.6584 | 7.4911 | 8.1695 | 8.393 | 7.5453 | 0.5526 | 0.9808 | 0.1304 |
| hsa-miR-548d-3p | 9.4748 | 9.1301 | 9.2124 | 9.4249 | 8.6869 | 8.9703 | 8.8381 | 8.8571 | 9.3242 | 9.5201 | 8.8183 | 0.4979 | 0.9788 | 0.1311 |
| hsa-miR-9-5p | 7.9022 | 7.8082 | 9.0217 | 8.8976 | 7.8999 | 7.7859 | 7.9263 | 7.7271 | 8.5708 | 9.0519 | 7.9827 | 0.7108 | 0.985 | 0.1318 |
| hsa-miR-18b-5p | 8.2018 | 7.534 | 8.226 | 7.8546 | 7.6198 | 7.8183 | 7.2136 | 7.643 | 7.9334 | 8.5713 | 7.3526 | 0.6026 | 0.9824 | 0.1319 |
| hsa-miR-549 | 2.6159 | 2.1077 | 2.4983 | 2.8094 | 2.2265 | 2.3277 | 2.0426 | 2 | 2.441 | 3.14571 | 1.9598 | 0.5694 | 0.9814 | 0.1321 |
| hsa-miR-1292 | 8.5476 | 7.9151 | 8.0527 | 7.5651 | 7.8422 | 7.7859 | 7.2531 | 7.8065 | 8.3242 | 8.3545 | 7.575 | 0.5856 | 0.9819 | 0.1347 |
| hsa-miR-569 | 8.6612 | 8.0385 | 8.5642 | 8.0956 | 7.585 | 7.7188 | 8.066 | 7.7271 | 8.2995 | 8.73 | 7.7677 | 0.6048 | 0.9825 | 0.1374 |
| hsa-miR-371a-5p | 7.8647 | 7.9406 | 7.5425 | 7.9394 | 7.437 | 7.5744 | 7.2136 | 7.4911 | 8.0854 | 8.145 | 7.1302 | 0.5181 | 0.9796 | 0.1382 |
| hsa-miR-580 | 9.437 | 8.5001 | 8.941 | 9.1139 | 8.5494 | 8.5163 | 8.6135 | 8.507 | 9.0265 | 9.4118 | 8.5453 | 0.5669 | 0.9813 | 0.1382 |
| hsa-miR-587 | 8.1087 | 7.7802 | 8.4754 | 8.2025 | 7.585 | 7.9703 | 7.7716 | 7.4586 | 7.9334 | 8.5026 | 7.7152 | 0.5321 | 0.9801 | 0.1384 |
| hsa-miR-548aj-3p | 9.4112 | 8.534 | 9.226 | 8.8976 | 8.2274 | 8.7694 | 8.6584 | 8.6285 | 9.2489 | 9.1894 | 8.5453 | 0.5008 | 0.9789 | 0.1393 |
| hsa-miR-1250 | 8.4497 | 8.3746 | 8.5856 | 8.5381 | 7.9824 | 8.4964 | 7.9979 | 7.7541 | 8.4639 | 9.0758 | 7.6882 | 0.5807 | 0.9817 | 0.14 |
| hsa-miR-581 | 8.7043 | 7.8082 | 8.82 | 8.454 | 7.9554 | 8.1594 | 8.1934 | 7.7805 | 8.3484 | 8.8999 | 7.8672 | 0.6023 | 0.9824 | 0.1403 |
| hsa-miR-34c-5p | 8.4994 | 8.0385 | 8.5642 | 8.2025 | 8.1817 | 8.3488 | 7.9979 | 7.7271 | 8.7083 | 8.6369 | 7.5149 | 0.5454 | 0.9806 | 0.1416 |
| hsa-miR-302b-3p | 8.9206 | 8.4653 | 8.4754 | 8.9187 | 8.1344 | 8.3488 | 8.6584 | 8.0436 | 8.8509 | 9.2535 | 8.3353 | 0.6015 | 0.9824 | 0.1437 |
| hsa-miR-34c-3p | 8.5237 | 8.1077 | 8.142 | 8.0956 | 7.8999 | 8.0814 | 7.7161 | 7.7541 | 8.4639 | 8.6369 | 7.6041 | 0.5199 | 0.9797 | 0.1444 |
| hsa-miR-759 | 8.6329 | 8.5001 | 8.8904 | 8.717 | 8.1817 | 8.3488 | 8.1522 | 7.9764 | 8.9173 | 8.8999 | 8.3526 | 0.485 | 0.9782 | 0.1445 |
| hsa-miR-410 | 8.2315 | 8.1952 | 8.0216 | 8.2696 | 7.8124 | 7.9135 | 7.9744 | 7.8321 | 7.9962 | 8.73 | 7.3179 | 0.497 | 0.9787 | 0.1458 |
| hsa-miR-579 | 9.6829 | 9.3932 | 9.7555 | 9.4684 | 9.0978 | 9.2923 | 9.3198 | 8.9649 | 9.68 | 9.9524 | 8.7932 | 0.5089 | 0.9792 | 0.1458 |
| hsa-miR-1825 | 8.2315 | 7.9904 | 8.253 | 8.7643 | 7.6582 | 8.0544 | 7.5031 | 7.8321 | 8.2995 | 8.873 | 7.6327 | 0.6067 | 0.9825 | 0.1461 |
| hsa-miR-3151 | 8.2018 | 7.8626 | 7.9899 | 7.9394 | 7.7821 | 7.8501 | 7.6286 | 7.3915 | 8.1695 | 8.6044 | 7.2082 | 0.5342 | 0.9802 | 0.1465 |
| hsa-miR-668 | 8.1404 | 7.6623 | 7.9575 | 8.1677 | 8.1101 | 7.6484 | 6.8786 | 7.5841 | 8.3242 | 8.0992 | 7.8183 | 0.3566 | 0.9706 | 0.1473 |
| hsa-miR-151b | 8.0762 | 8.0385 | 7.9555 | 7.6681 | 7.9554 | 8.0269 | 7.2916 | 7.3915 | 8.142 | 8.4304 | 7.4521 | 0.4912 | 0.9785 | 0.1501 |
| hsa-miR-1193 | 8.7461 | 8.534 | 8.746 | 8.6681 | 7.8999 | 8.0544 | 8.4699 | 8.0436 | 8.7814 | 8.8999 | 7.9603 | 0.5304 | 0.98 | 0.1506 |
| hsa-miR-1225-5p | 9.2315 | 8.6313 | 9.1128 | 8.7409 | 8.3773 | 8.684 | 8.1934 | 8.3742 | 9.128 | 9.3738 | 8.2457 | 0.5644 | 0.9812 | 0.1522 |
| hsa-miR-139-5p | 8.7666 | 8.3366 | 8.7269 | 8.0956 | 8.2048 | 8.0269 | 7.9979 | 8.1285 | 8.529 | 8.8455 | 8.11 | 0.4517 | 0.9767 | 0.1531 |
| hsa-miR-133b | 9.2892 | 8.6469 | 9.1275 | 8.6681 | 8.5129 | 8.6484 | 8.6584 | 8.3211 | 8.8678 | 9.4118 | 8.2641 | 0.5173 | 0.9796 | 0.1537 |
| hsa-miR-590-5p | 9.3447 | 7.9904 | 9.417 | 8.8325 | 8.8857 | 8.7015 | 8.2251 | 8.918 | 9.1695 | 9.5201 | 8.7152 | 0.4028 | 0.9739 | 0.1537 |
| hsa-miR-525-3p | 8.4497 | 8.4981 | 8.4981 | 7.9801 | 7.928 | 8.4762 | 7.7441 | 7.5841 | 8.4639 | 8.5026 | 7.3179 | 0.5534 | 0.9809 | 0.1544 |
| hsa-miR-378b | 8.6168 | 8.1301 | 8.6479 | 7.9394 | 7.6538 | 7.8183 | 7.6876 | 7.6996 | 8.1964 | 8.6996 | 7.7152 | 0.5454 | 0.9806 | 0.1544 |
| hsa-miR-330-5p | 9.2892 | 8.7516 | 9.1128 | 8.6681 | 7.9554 | 8.5553 | 7.2916 | 8.9992 | 8.142 | 9.3738 | 8.0688 | 0.5389 | 0.9804 | 0.155 |
| hsa-miR-338-5p | 8.1404 | 8.534 | 8.4981 | 8.7409 | 7.8999 | 8.684 | 8.4699 | 8.0436 | 8.6314 | 8.4304 | 7.4197 | 0.5275 | 0.9799 | 0.1551 |
| hsa-miR-921 | 8.0762 | 7.534 | 8.1705 | 8.1321 | 8.3773 | 7.414 | 8.1934 | 8.3742 | 7.9651 | 8.0992 | 7.7677 | 0.4178 | 0.9748 | 0.1552 |
| hsa-miR-139-3p | 8.2018 | 7.9151 | 8.668 | 8.454 | 7.5494 | 7.9412 | 7.7441 | 7.4254 | 8.4415 | 8.6044 | 7.4838 | 0.5667 | 0.9813 | 0.1565 |
| hsa-miR-568 | 9.1087 | 9.0266 | 9.331 | 9 | 8.7667 | 8.9114 | 8.066 | 7.5537 | 8.9267 | 8.6044 | 8.5602 | 0.3942 | 0.9733 | 0.1566 |
| hsa-miR-367-3p | 8.4242 | 8.3172 | 8.5425 | 7.7643 | 8.0854 | 8.1338 | 8.6135 | 8.5991 | 9.2617 | 9.0277 | 7.6882 | 0.5669 | 0.9813 | 0.1568 |
| hsa-miR-548b-3p | 7.8647 | 7.6313 | 7.8904 | 8.058 | 7.928 | 7.8183 | 7.9744 | 7.4254 | 8.1695 | 8.5373 | 7.4521 | 0.4908 | 0.9785 | 0.1569 |
| hsa-miR-499b-5p | 7.9388 | 8.2163 | 8.0216 | 7.9394 | 7.5494 | 8.0269 | 7.1729 | 7.3568 | 7.9651 | 8.2325 | 7.3179 | 0.5003 | 0.9789 | 0.1574 |
| hsa-miR-566 | 8.6168 | 8.7802 | 8.7076 | 8.9187 | 8.6704 | 8.684 | 7.825 | 7.6996 | 7.9962 | 8.6996 | 7.7152 | 0.3481 | 0.9699 | 0.1585 |
| hsa-miR-330-5p | 9.9744 | 7.6623 | 7.8201 | 7.3337 | 7.315 | 7.1845 | 8.3835 | 8.303 | 8.7635 | 9.2948 | 8.4681 | 0.3481 | 0.9699 | 0.1608 |
| hsa-miR-324-3p | 8.1404 | 7.6623 | 8.4981 | 8.2364 | 8.2048 | 7.0546 | 7.4012 | 7.5841 | 7.9651 | 7.73 | 7.0896 | 0.4539 | 0.9768 | 0.1619 |
| hsa-miR-875-5p | 8.2018 | 8.3932 | 8.4288 | 8.4248 | 8.8714 | 7.8811 | 8.2916 | 8.1077 | 8.2229 | 8.393 | 7.7152 | 0.3085 | 0.9662 | 0.1621 |
| hsa-miR-933 | 8.5476 | 8.3172 | 8.7649 | 8.3337 | 8.0854 | 8.4557 | 7.7441 | 7.9534 | 8.4188 | 8.9264 | 7.9827 | 0.4624 | 0.9772 | 0.1629 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-935 | 7.7461 | 7.8626 | 8.2795 | 7.9801 | 7.315 | 7.8183 | 7.2916 | 7.2846 | 8.0854 | 8.315 | 7.2456 | 0.5252 | 0.9799 | 0.1632 |
| hsa-miR-33b-5p | 8.2315 | 7.8082 | 7.9899 | 7.9801 | 7.8422 | 7.9412 | 7.2136 | 7.7541 | 7.8678 | 8.393 | 7.6607 | 0.3735 | 0.9719 | 0.1653 |
| hsa-miR-646 | 7.8262 | 7.6927 | 7.8904 | 7.5106 | 7.7511 | 7.4964 | 7.3656 | 7.0866 | 7.8678 | 8.2325 | 7.3526 | 0.3888 | 0.973 | 0.1673 |
| hsa-miR-3180 | 8.8456 | 8.6313 | 8.4981 | 8.8976 | 8.315 | 7.9703 | 8.1522 | 8.5227 | 9.1558 | 8.6996 | 8.3179 | 0.4348 | 0.9758 | 0.1678 |
| hsa-miR-1255a | 8.0762 | 7.6313 | 8.2795 | 7.9394 | 8.2275 | 7.7527 | 7.3656 | 7.7805 | 8.2489 | 8.8175 | 7.2082 | 0.5497 | 0.9807 | 0.1685 |
| hsa-miR-3127-5p | 8.3447 | 7.8626 | 7.8201 | 7.5106 | 7.6869 | 8.4557 | 7.0881 | 7.3915 | 7.6115 | 8.1894 | 7.3179 | 0.5312 | 0.9801 | 0.1693 |
| hsa-miR-548u | 7.6168 | 6.9152 | 7.668 | 7.6175 | 7.1817 | 7.1338 | 7.0881 | 6.906 | 7.8678 | 7.467 | 6.9144 | 0.4462 | 0.9764 | 0.1703 |
| hsa-miR-1286 | 8.7253 | 8.4297 | 8.746 | 8.5915 | 8.7032 | 8.7188 | 8.2335 | 8.5991 | 8.7453 | 8.3545 | 8.1501 | 0.1893 | 0.946 | 0.1723 |
| hsa-miR-4458 | 8.8066 | 8.4653 | 8.7269 | 8.9599 | 8.437 | 8.3709 | 8.3291 | 8.4254 | 8.5501 | 9.0992 | 8.2457 | 0.3044 | 0.9657 | 0.1758 |
| hsa-miR-618 | 7.9388 | 7.2371 | 7.4981 | 7.8976 | 7.4754 | 7.5359 | 6.851 | 7.3568 | 7.7991 | 7.8455 | 7.2082 | 0.4094 | 0.9743 | 0.1766 |
| hsa-miR-505-3p | 8.2315 | 7.1952 | 8.0527 | 7.7171 | 7.2718 | 7.414 | 7.5673 | 6.906 | 7.9334 | 8.315 | 6.9603 | 0.5734 | 0.9815 | 0.1777 |
| hsa-miR-657 | 8.6829 | 8.1738 | 8.4754 | 8.2025 | 7.9824 | 8.435 | 7.7986 | 7.4911 | 8.2229 | 8.8455 | 7.9603 | 0.4652 | 0.9773 | 0.1778 |
| hsa-miR-412 | 9.0925 | 8.5172 | 8.4288 | 8.7643 | 8.1101 | 8.5163 | 8.6135 | 7.7805 | 8.651 | 8.73 | 8.11 | 0.4388 | 0.976 | 0.1824 |
| hsa-miR-323a-5p | 8.0762 | 7.5001 | 8.226 | 8.0196 | 7.1344 | 7.5359 | 7.5031 | 7.5227 | 7.5708 | 8.2325 | 7.2823 | 0.4758 | 0.9778 | 0.1834 |
| hsa-miR-939 | 8.1087 | 8.0619 | 8.1985 | 8.2364 | 8.315 | 8.0544 | 7.8766 | 7.9534 | 8.1964 | 8.5026 | 7.4197 | 0.2781 | 0.9626 | 0.1836 |
| hsa-miR-101-3p | 8.1087 | 7.6313 | 8.5856 | 8.0196 | 7.5494 | 7.6484 | 7.47 | 7.5537 | 8.114 | 8.393 | 7.575 | 0.4591 | 0.977 | 0.1866 |
| hsa-miR-654-3p | 9.3982 | 8.8759 | 9.0059 | 9.2025 | 8.8714 | 9.1338 | 8.4699 | 8.5383 | 9.2229 | 9.2111 | 7.7285 | 0.3127 | 0.9666 | 0.1867 |
| hsa-miR-586 | 8.4994 | 8.2777 | 8.4288 | 8.5915 | 7.9554 | 8.1594 | 7.8766 | 7.8818 | 8.5076 | 8.7889 | 7.7677 | 0.376 | 0.9721 | 0.1869 |
| hsa-miR-378d | 7.5237 | 7.3557 | 7.9899 | 8.1677 | 7.8422 | 7.4557 | 7.2136 | 7.2846 | 7.8678 | 8.393 | 7.3179 | 0.4543 | 0.9768 | 0.1871 |
| hsa-miR-411-5p | 8.5476 | 7.7802 | 8.4754 | 8.717 | 7.585 | 7.8811 | 7.9017 | 7.9299 | 8.4188 | 8.5713 | 7.4838 | 0.5145 | 0.9794 | 0.1899 |
| hsa-miR-124-3p | 8.5237 | 8.2976 | 8.3561 | 8.1321 | 8.1101 | 7.9115 | 7.9017 | 7.8572 | 8.3723 | 8.5713 | 9.9376 | 0.2215 | 0.9535 | 0.192 |
| hsa-miR-603 | 8.0431 | 8.3932 | 8.4288 | 8.3647 | 8.0604 | 7.8811 | 7.9017 | 7.9764 | 8.2229 | 8.5373 | 7.8672 | 0.1949 | 0.9475 | 0.1936 |
| hsa-miR-3136-5p | 8.3717 | 7.6313 | 8.0831 | 8.3337 | 7.7193 | 7.7188 | 7.6876 | 7.5841 | 8.114 | 8.0992 | 7.7932 | 0.3108 | 0.9664 | 0.195 |
| hsa-miR-637 | 8.1714 | 7.8891 | 8.1705 | 7.8976 | 7.585 | 7.8811 | 7.2916 | 7.5537 | 7.9651 | 8.0519 | 7.7417 | 0.2508 | 0.9587 | 0.1952 |
| hsa-miR-1287 | 8.3447 | 8.5672 | 9.2124 | 8.7643 | 8.437 | 8.6119 | 8.2136 | 8.228 | 8.7635 | 8.9524 | 8.0478 | 0.3815 | 0.9725 | 0.1956 |
| hsa-miR-2115-5p | 7.4748 | 7.0147 | 7.8201 | 7.7643 | 7.3568 | 7.4557 | 6.9979 | 7.1691 | 7.8678 | 7.5374 | 6.7152 | 0.4037 | 0.9739 | 0.1956 |
| hsa-miR-339-5p | 8.0762 | 7.7802 | 8.3055 | 7.5106 | 7.2275 | 7.6484 | 7.2916 | 7.0866 | 7.5708 | 8.393 | 7.5149 | 0.4796 | 0.978 | 0.1958 |
| hsa-miR-602 | 7.3172 | 6.9658 | 7.0831 | 6.8102 | 6.8714 | 7.1845 | 6.2135 | 6.5841 | 7.7635 | 6.467 | 6.6608 | 0.4536 | 0.9768 | 0.1973 |
| hsa-miR-487a | 8.3717 | 8.1521 | 8.2795 | 8.5381 | 7.2275 | 8.0544 | 7.8766 | 7.4254 | 7.9651 | 8.5713 | 7.6041 | 0.5043 | 0.979 | 0.1976 |
| hsa-miR-211-5p | 8.2018 | 8.3746 | 8.4754 | 8.3337 | 7.7821 | 7.8811 | 7.825 | 7.906 | 8.0854 | 8.8455 | 7.6607 | 0.3682 | 0.9715 | 0.1995 |
| hsa-miR-3690 | 9.1714 | 8.6623 | 9.0372 | 8.9187 | 8.2499 | 8.2807 | 8.2725 | 8.5227 | 9.0265 | 9.2535 | 8.2822 | 0.4217 | 0.975 | 0.2015 |
| hsa-miR-495 | 10.4112 | 10.1952 | 10.683 | 10.8158 | 9.8999 | 10.02 | 10.099 | 10.1387 | 10.4968 | 10.5962 | 9.8368 | 0.3488 | 0.97 | 0.2031 |
| hsa-miR-2277-3p | 8.6168 | 8.3172 | 8.405 | 8.7874 | 8.1101 | 8.3709 | 8.066 | 7.9992 | 8.3957 | 8.8175 | 7.7932 | 0.3038 | 0.9657 | 0.2069 |
| hsa-miR-129-2-3p | 8.3717 | 8.1077 | 9.0527 | 8.4248 | 7.6198 | 8.0814 | 8.2725 | 7.6139 | 8.3484 | 8.6369 | 7.6882 | 0.485 | 0.9782 | 0.2085 |
| hsa-miR-1228-3p | 9.571 | 8.9279 | 9.331 | 9.2859 | 8.7032 | 8.9847 | 8.7441 | 8.6716 | 8.8961 | 9.7149 | 8.6185 | 0.3797 | 0.9724 | 0.2088 |
| hsa-miR-370 | 8.4748 | 8.237 | 8.6479 | 8.3951 | 8.0604 | 8.3488 | 7.9744 | 7.7441 | 8.2995 | 8.6044 | 8.0264 | 0.2461 | 0.958 | 0.2088 |
| hsa-miR-507 | 8.2607 | 8.1952 | 8.5856 | 8.454 | 7.5494 | 7.9703 | 7.5355 | 7.7541 | 8.529 | 8.2743 | 7.9376 | 0.3911 | 0.9711 | 0.2088 |
| hsa-miR-590-3p | 9.0262 | 8.6776 | 8.8731 | 8.6681 | 7.8422 | 7.8807 | 7.9744 | 8.3915 | 8.6895 | 9.1674 | 7.9376 | 0.4708 | 0.9776 | 0.2106 |
| hsa-miR-376b | 8.8647 | 8.7371 | 9.1275 | 8.2696 | 8.315 | 8.2334 | 8.3105 | 8.507 | 9.0563 | 8.6686 | 7.9376 | 0.3796 | 0.9723 | 0.2106 |
| hsa-miR-663b | 8.4748 | 7.8357 | 8.2795 | 8.4826 | 7.8124 | 7.8501 | 8.1098 | 7.643 | 8.2995 | 8.8455 | 7.0478 | 0.4882 | 0.9784 | 0.2111 |
| hsa-miR-485-3p | 8.3981 | 7.8626 | 8.0831 | 8.058 | 8.2275 | 8.1338 | 7.3656 | 7.3211 | 8.5076 | 8.6996 | 7.4521 | 0.4537 | 0.9768 | 0.2126 |
| hsa-miR-3178 | 8.2315 | 6.927 | 8.5425 | 7.8546 | 6.6538 | 7.9115 | 7.6876 | 7.4254 | 8.0854 | 8.1894 | 7.3866 | 0.3571 | 0.9706 | 0.214 |
| hsa-miR-369-3p | 9.1087 | 8.2777 | 8.4981 | 8.1677 | 8.1582 | 8.2572 | 7.9506 | 7.8572 | 8.6704 | 9.0277 | 7.6041 | 0.467 | 0.9774 | 0.2142 |
| hsa-miR-3164 | 8.4242 | 8.4297 | 8.5425 | 8.565 | 8.1101 | 8.0544 | 8.7441 | 7.9992 | 8.6115 | 8.6686 | 7.9603 | 0.2239 | 0.954 | 0.215 |
| hsa-miR-345-5p | 8.4242 | 7.8082 | 8.331 | 8.058 | 8.8714 | 7.7188 | 7.9744 | 7.9534 | 7.9651 | 8.2325 | 7.4521 | 0.2208 | 0.9534 | 0.2158 |
| hsa-miR-510 | 8.7043 | 8.3746 | 8.7649 | 8.3951 | 7.7193 | 8.1844 | 7.825 | 8.2086 | 8.4188 | 8.5713 | 7.8429 | 0.3623 | 0.9711 | 0.2164 |
| hsa-miR-512-3p | 8.6168 | 7.6313 | 8.3808 | 8.5106 | 8.0349 | 8.1594 | 7.9506 | 7.9992 | 8.1695 | 8.315 | 7.5149 | 0.3427 | 0.9695 | 0.2168 |
| hsa-miR-1206 | 7.9022 | 8.2976 | 8.9575 | 8.2696 | 7.928 | 8.1338 | 7.5355 | 7.9534 | 8.0563 | 9.0992 | 7.5453 | 0.4898 | 0.9784 | 0.2171 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-1270 | 7.7867 | 7.4297 | 7.8904 | 7.7171 | 7.4754 | 7.8501 | 7.2136 | 7.2086 | 7.9334 | 7.467 | 6.9603 | 0.2588 | 0.9599 | 0.221 |
| hsa-miR-513a-5p | 8.1404 | 7.8891 | 8.331 | 8.0956 | 8.1817 | 7.8811 | 7.6584 | 7.5537 | 8.2744 | 8.5373 | 7.5149 | 0.2668 | 0.9611 | 0.2242 |
| hsa-miR-140-3p | 8.7461 | 8.7225 | 8.9738 | 8.8545 | 8.0349 | 8.1338 | 8.3291 | 8.189 | 8.8166 | 9.0519 | 8.1302 | 0.355 | 0.9705 | 0.2246 |
| hsa-miR-550b-3p | 8.1714 | 8.085 | 8.1128 | 8.5915 | 8.2048 | 8.3265 | 7.6584 | 7.6139 | 8.0854 | 8.7889 | 7.575 | 0.338 | 0.969 | 0.2251 |
| hsa-miR-1912 | 7.7461 | 7.1078 | 7.8201 | 8.0956 | 7.6198 | 7.0814 | 7.4012 | 7.3915 | 7.4859 | 8.003 | 7.3526 | 0.3024 | 0.9655 | 0.2253 |
| hsa-miR-532-3p | 7.8647 | 7.5001 | 7.746 | 7.1321 | 7.1344 | 7.414 | 6.851 | 7.1285 | 7.727 | 7.6044 | 6.7677 | 0.3335 | 0.9686 | 0.2267 |
| hsa-miR-3185 | 8.7666 | 7.9406 | 8.2795 | 8.2696 | 7.8999 | 7.684 | 7.6286 | 7.5841 | 8.3957 | 8.8175 | 7.9145 | 0.3989 | 0.9736 | 0.2271 |
| hsa-miR-498 | 8.5941 | 8.3932 | 8.5205 | 8.302 | 7.8124 | 8.684 | 7.5983 | 8.3211 | 8.0563 | 8.2325 | 7.6882 | 0.3192 | 0.9673 | 0.2277 |
| hsa-miR-491-5p | 8.9022 | 8.4653 | 8.6479 | 8.3647 | 8.1582 | 8.1844 | 8.1934 | 7.7271 | 8.5076 | 8.8175 | 8.2457 | 0.2723 | 0.9619 | 0.2284 |
| hsa-miR-501-3p | 8.2315 | 8.3366 | 8.3055 | 7.9394 | 7.9554 | 7.9412 | 7.7161 | 7.4911 | 8.3484 | 8.393 | 7.6607 | 0.2298 | 0.9551 | 0.2286 |
| hsa-miR-3196 | 9.1714 | 8.9657 | 8.8019 | 8.9394 | 8.6537 | 8.6303 | 8.4699 | 8.5227 | 8.9651 | 8.9779 | 8.4994 | 0.1095 | 0.9103 | 0.2289 |
| hsa-miR-509-5p | 7.8647 | 7.7623 | 7.3561 | 7.8101 | 7.7193 | 7.4964 | 6.9017 | 7.3211 | 7.7991 | 8.1894 | 7.0047 | 0.3259 | 0.9679 | 0.2304 |
| hsa-miR-3141 | 8.0762 | 8.0146 | 7.8201 | 8.454 | 7.6869 | 7.6484 | 8.8766 | 7.6716 | 8.0563 | 7.7889 | 7.6327 | 0.1665 | 0.9391 | 0.2313 |
| hsa-miR-1200 | 8.3981 | 8.1738 | 8.4523 | 8.2696 | 8.0088 | 8.2091 | 7.744 | 7.7541 | 8.3484 | 8.6044 | 7.5149 | 0.2617 | 0.9604 | 0.2314 |
| hsa-miR-330-3p | 8.8836 | 8.4476 | 9.142 | 8.9801 | 8.315 | 8.2807 | 8.2136 | 8.4749 | 8.7814 | 9.2325 | 8.1501 | 0.3458 | 0.9697 | 0.2314 |
| hsa-miR-4448 | 9.1087 | 8.5001 | 9.1275 | 8.302 | 8.0854 | 8.2334 | 7.8511 | 8.4586 | 8.7991 | 9.1223 | 7.8911 | 0.4526 | 0.9767 | 0.2321 |
| hsa-miR-130b-3p | 8.8836 | 8.4476 | 9.226 | 8.565 | 8.8124 | 8.435 | 7.9263 | 7.9299 | 8.9493 | 9.145 | 7.7417 | 0.5075 | 0.9792 | 0.2324 |
| hsa-miR-493-3p | 8.3981 | 8.0385 | 8.0527 | 8.1677 | 7.6198 | 7.5359 | 7.7716 | 7.4254 | 8.2489 | 8.467 | 7.4838 | 0.3152 | 0.9669 | 0.2332 |
| hsa-miR-1296 | 7.3172 | 7.5001 | 7.746 | 7.7171 | 6.9824 | 7.684 | 6.7986 | 7.0435 | 7.5708 | 7.73 | 6.4838 | 0.3837 | 0.9726 | 0.2341 |
| hsa-miR-422a | 9.0598 | 8.766 | 8.8556 | 8.7643 | 8.0854 | 8.3265 | 8.3291 | 7.906 | 8.7269 | 9.1894 | 8.3526 | 0.359 | 0.9708 | 0.2345 |
| hsa-miR-503 | 8.7043 | 8.4476 | 9.0527 | 8.6681 | 8.1582 | 8.1078 | 8.2916 | 8.339 | 8.9493 | 8.8455 | 7.6882 | 0.356 | 0.9706 | 0.2359 |
| hsa-miR-1307-3p | 8.8836 | 8.4653 | 9.0527 | 8.4248 | 8.2936 | 8.5359 | 8.0881 | 8.1489 | 8.7991 | 8.9524 | 7.7677 | 0.3335 | 0.9686 | 0.242 |
| hsa-miR-4435 | 8.2607 | 7.7802 | 8.1128 | 8.6175 | 7.7511 | 7.8183 | 7.7161 | 6.9992 | 8.2489 | 8.6996 | 7.6882 | 0.4168 | 0.9747 | 0.2427 |
| hsa-miR-627 | 9.1404 | 9.0503 | 9.142 | 9.2364 | 8.8274 | 8.684 | 8.7161 | 8.6996 | 9.2229 | 9.3738 | 8.3179 | 0.2057 | 0.9501 | 0.2436 |
| hsa-miR-519d | 9.0091 | 8.4297 | 9.1275 | 8.5106 | 7.9554 | 8.1844 | 8.2531 | 7.7541 | 8.6704 | 8.73 | 8.0264 | 0.3162 | 0.967 | 0.2448 |
| hsa-miR-509-3p | 8.1087 | 7.5672 | 8.1705 | 7.7371 | 7.6198 | 7.7527 | 6.9979 | 7.3211 | 8.529 | 7.8455 | 7.0896 | 0.3816 | 0.9725 | 0.2473 |
| hsa-miR-548a-5p | 8.4497 | 7.9151 | 8.82 | 8.8545 | 7.6538 | 7.9412 | 8.1522 | 7.7805 | 8.0563 | 8.873 | 7.575 | 0.426 | 0.9753 | 0.2507 |
| hsa-miR-212-3p | 9.1246 | 8.822 | 9.2925 | 8.8102 | 8.6198 | 8.7359 | 8.3291 | 8.5991 | 8.8509 | 9.0992 | 8.4839 | 0.2508 | 0.9379 | 0.2508 |
| hsa-miR-635 | 8.7253 | 8.0146 | 8.6479 | 8.8325 | 8.2275 | 8.5163 | 7.9744 | 7.9534 | 8.486 | 8.6044 | 7.8911 | 0.3162 | 0.9595 | 0.252 |
| hsa-miR-596 | 8.5941 | 8.534 | 8.8556 | 8.7874 | 7.9824 | 8.2807 | 7.7986 | 8.0866 | 8.3242 | 9.2535 | 8.0478 | 0.3816 | 0.9703 | 0.2522 |
| hsa-miR-409-3p | 9.4748 | 8.9657 | 9.1705 | 9.0956 | 8.8714 | 8.2572 | 8.1522 | 8.3211 | 9.475 | 9.4849 | 8.0478 | 0.426 | 0.9797 | 0.254 |
| hsa-miR-758 | 8.1714 | 7.5001 | 8.1128 | 8.3337 | 7.6198 | 7.5359 | 7.1311 | 7.1691 | 8.1695 | 8.3545 | 7.7932 | 0.3591 | 0.9708 | 0.2553 |
| hsa-miR-323a-3p | 9.0262 | 8.822 | 9.226 | 9.1852 | 8.6025 | 8.684 | 8.4531 | 8.643 | 9.0854 | 9.0992 | 8.3353 | 0.1765 | 0.9423 | 0.2557 |
| hsa-miR-517b-3p | 7.4748 | 6.8083 | 6.8201 | 6.8976 | 9.6279 | 6.6485 | 6.2135 | 5.4584 | 7.7991 | 7.3929 | 8.8672 | 0.5064 | 0.9791 | 0.2558 |
| hsa-miR-1468 | 8.0762 | 7.8891 | 8.3561 | 8.1677 | 7.585 | 7.6118 | 7.2136 | 7.4911 | 8.0854 | 8.6996 | 7.4521 | 0.3502 | 0.9701 | 0.2559 |
| hsa-miR-432-5p | 9.0925 | 8.5672 | 8.7269 | 9.0956 | 8.437 | 8.3926 | 8.3291 | 8.339 | 8.7991 | 9.3929 | 7.9145 | 0.3301 | 0.9683 | 0.256 |
| hsa-miR-329 | 9.0762 | 8.4828 | 9.0831 | 9.0196 | 8.3568 | 8.6484 | 8.436 | 8.4749 | 8.8678 | 8.9524 | 7.8911 | 0.2744 | 0.9621 | 0.2586 |
| hsa-miR-18a-5p | 9.6936 | 9.1412 | 9.7173 | 9.0581 | 8.336 | 8.9847 | 8.5194 | 8.9534 | 9.2489 | 9.5713 | 8.3001 | 0.4363 | 0.9758 | 0.2596 |
| hsa-miR-190a | 8.6612 | 8.534 | 8.9738 | 8.3951 | 7.8999 | 8.3488 | 7.4012 | 7.7805 | 8.6314 | 9.145 | 8.0896 | 0.4222 | 0.9751 | 0.2601 |
| hsa-miR-146b-3p | 8.0091 | 7.5001 | 8.3337 | 8.3337 | 7.5129 | 7.9115 | 7.2916 | 7.2471 | 7.8338 | 8.2743 | 7.0896 | 0.3212 | 0.9675 | 0.2612 |
| hsa-miR-767-3p | 7.8461 | 7.6927 | 7.9899 | 8.2364 | 7.928 | 7.6484 | 7.6876 | 7.6716 | 8.1964 | 8.145 | 7.7417 | 0.248 | 0.9583 | 0.2637 |
| hsa-miR-424-5p | 9.3717 | 9.0736 | 7.9575 | 9.1852 | 8.751 | 8.6663 | 8.5672 | 8.5227 | 9.6412 | 9.5026 | 8.6882 | 0.3143 | 0.9668 | 0.2683 |
| hsa-miR-326 | 7.7867 | 6.8083 | 9.617 | 7.3337 | 7.1344 | 7.3264 | 6.7442 | 6.8066 | 7.529 | 7.0519 | 7.0047 | 0.2515 | 0.9588 | 0.2691 |
| hsa-miR-328 | 8.4497 | 7.5996 | 7.668 | 7.668 | 7.437 | 7.2333 | 7.876 | 7.4911 | 8.0854 | 8.0992 | 7.5149 | 0.304 | 0.9657 | 0.2731 |
| hsa-miR-335-5p | 8.7666 | 8.5001 | 8.331 | 8.8325 | 8.336 | 8.7188 | 7.9506 | 8.1285 | 8.8339 | 9.3929 | 8.11 | 0.3974 | 0.9735 | 0.2731 |
| hsa-miR-3928 | 8.6829 | 8.2575 | 9.5425 | 8.3337 | 8.315 | 8.2334 | 7.7161 | 7.7271 | 8.5708 | 8.9779 | 7.6327 | 0.2897 | 0.9641 | 0.2744 |
| hsa-miR-520h | 9.3033 | 9.0503 | 8.4981 | 8.8976 | 8.5494 | 8.7015 | 8.4187 | 8.3742 | 8.901 | 9.5713 | 8.3353 | 0.2694 | 0.9615 | 0.2744 |
| hsa-miR-499b-3p | 8.5941 | 7.6927 | 8.4288 | 7.8976 | 7.7193 | 7.6484 | 7.2136 | 7.7541 | 8.0563 | 8.5026 | 7.575 | 0.3184 | 0.9672 | 0.2748 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-1224-5p | 8.3981 | 8.6469 | 8.6066 | 7.8546 | 6.9824 | 7.8501 | 7.7986 | 7.6716 | 7.9334 | 8.393 | 7.2823 | 0.4559 | 0.9769 | 0.2763 |
| hsa-miR-513a-3p | 8.3717 | 7.7225 | 7.9899 | 8.058 | 7.5129 | 7.6118 | 7.6876 | 7.2846 | 7.901 | 8.4304 | 7.0047 | 0.2964 | 0.9648 | 0.2777 |
| hsa-miR-1260b | 7.7461 | 7.9151 | 8.2795 | 8.0196 | 7.6198 | 7.6484 | 7.0436 | 8.0215 | 8.0563 | 7.8455 | 7.2082 | 0.2148 | 0.9521 | 0.2788 |
| hsa-miR-633 | 8.1404 | 7.9657 | 8.0527 | 8.302 | 8.3773 | 8.1844 | 7.6286 | 7.4911 | 8.2229 | 8.315 | 7.4838 | 0.1584 | 0.9362 | 0.28 |
| hsa-miR-1247-5p | 7.9388 | 7.3932 | 8.1128 | 8.7409 | 7.315 | 7.3709 | 7.5983 | 7.1285 | 8.4188 | 8.2325 | 6.9603 | 0.4483 | 0.9765 | 0.2819 |
| hsa-miR-379-5p | 8.4242 | 7.7225 | 7.8557 | 8.2025 | 7.315 | 7.1845 | 7.47 | 7.6716 | 7.9651 | 8.145 | 7.2823 | 0.2833 | 0.9633 | 0.2842 |
| hsa-miR-339-3p | 8.3447 | 8.0146 | 8.1705 | 8.4826 | 7.4754 | 7.5744 | 7.6584 | 7.3568 | 8.0563 | 8.5713 | 7.6607 | 0.2827 | 0.9632 | 0.2846 |
| hsa-miR-662 | 8.0431 | 7.9657 | 7.8904 | 8.1321 | 7.3568 | 7.5359 | 7.436 | 7.3211 | 7.7635 | 8.145 | 7.3526 | 0.1627 | 0.9378 | 0.2853 |
| hsa-miR-1268a | 8.7867 | 8.2777 | 8.253 | 7.9394 | 7.7511 | 7.9412 | 7.6286 | 7.7271 | 8.3723 | 8.467 | 7.3526 | 0.282 | 0.9631 | 0.2868 |
| hsa-miR-1279 | 8.4623 | 9.0736 | 9.0831 | 8.8976 | 8.0088 | 8.4964 | 8.2916 | 8.8193 | 8.6314 | 9.3545 | 8.11 | 0.3683 | 0.9715 | 0.2879 |
| hsa-miR-296-5p | 7.8647 | 7.4297 | 8.6066 | 8.2696 | 7.8124 | 7.414 | 7.47 | 7.2471 | 8.114 | 8.873 | 7.1302 | 0.4168 | 0.9748 | 0.2886 |
| hsa-miR-504 | 8.2892 | 7.6927 | 8.226 | 8.565 | 7.437 | 7.9412 | 7.4012 | 7.1691 | 8.2995 | 8.3545 | 7.3526 | 0.3527 | 0.9703 | 0.289 |
| hsa-miR-609 | 8.0091 | 7.534 | 7.9899 | 7.5106 | 7.6869 | 6.85 | 7.2531 | 7.3568 | 7.6115 | 8.1894 | 7.4521 | 0.2004 | 0.9489 | 0.294 |
| hsa-miR-302f | 8.5941 | 8.3746 | 8.3808 | 8.5915 | 7.928 | 8.2334 | 7.9744 | 7.5227 | 8.4639 | 8.6369 | 6.6327 | 0.2122 | 0.9516 | 0.2964 |
| hsa-miR-516a-3p | 8.9387 | 8.4476 | 8.4523 | 8.6928 | 8.1344 | 9.9703 | 8.2136 | 7.9992 | 8.5501 | 8.73 | 7.9376 | 0.1528 | 0.934 | 0.2997 |
| hsa-miR-611 | 8.0091 | 8.1738 | 8.1128 | 8.2364 | 7.9824 | 7.9412 | 7.5673 | 7.3915 | 8.2489 | 8.315 | 7.3526 | 0.1495 | 0.9326 | 0.3002 |
| hsa-miR-514b-3p | 8.1714 | 7.9657 | 8.253 | 8.0196 | 8.4422 | 7.9115 | 7.2136 | 7.1691 | 8.5501 | 8.1894 | 7.4521 | 0.2547 | 0.9593 | 0.3027 |
| hsa-miR-4792 | 8.571 | 8.5996 | 8.7269 | 8.4826 | 7.7193 | 7.9703 | 7.7716 | 7.7541 | 8.5708 | 9.003 | 7.6327 | 0.3186 | 0.9672 | 0.3028 |
| hsa-miR-1180 | 8.2892 | 7.7225 | 8.1705 | 7.9801 | 7.6538 | 7.6484 | 7.6584 | 7.1285 | 7.8678 | 8.145 | 7.4838 | 0.1337 | 0.9253 | 0.3079 |
| hsa-miR-543 | 8.3447 | 8.1301 | 8.4981 | 8.6681 | 7.585 | 8.0814 | 7.436 | 7.8572 | 8.486 | 8.2743 | 7.4838 | 0.2579 | 0.9598 | 0.3088 |
| hsa-miR-7-5p | 9.4112 | 8.534 | 9.9075 | 8.8325 | 8.4754 | 7.9989 | 8.5355 | 8.2659 | 9.0092 | 9.5201 | 8.11 | 0.4871 | 0.9783 | 0.3089 |
| hsa-miR-382-5p | 8.8836 | 8.822 | 9.1128 | 9 | 8.0349 | 8.435 | 8.3291 | 7.9299 | 8.7991 | 9.145 | 8.11 | 0.2678 | 0.9612 | 0.3126 |
| hsa-miR-652-3p | 9.0598 | 8.1952 | 8.6274 | 7.8546 | 7.1817 | 7.8811 | 7.436 | 7.7805 | 8.0854 | 8.6686 | 7.3526 | 0.43 | 0.9755 | 0.3164 |
| hsa-miR-19a-3p | 8.9387 | 8.8626 | 10.068 | 8.454 | 7.0854 | 7.7859 | 7.9263 | 8.7805 | 8.9493 | 9.3929 | 7.3526 | 0.6003 | 0.9823 | 0.3172 |
| hsa-miR-134 | 9.275 | 9.1301 | 9.5315 | 8.2696 | 8.8999 | 8.5744 | 8.5355 | 8.6857 | 8.6314 | 8.9264 | 7.6607 | 0.4073 | 0.9742 | 0.3189 |
| hsa-miR-483-3p | 8.8263 | 8.4297 | 9.3807 | 8.8545 | 7.928 | 8.0269 | 8.021 | 8.228 | 8.486 | 9.0758 | 8.3353 | 0.3036 | 0.9657 | 0.3217 |
| hsa-miR-1180 | 8.9744 | 8.2575 | 8.7835 | 8.4826 | 7.6538 | 7.8183 | 7.6876 | 8.0866 | 8.5913 | 8.6686 | 7.7932 | 0.296 | 0.9648 | 0.3227 |
| hsa-miR-663a | 10.0762 | 9.5916 | 9.746 | 9.3337 | 8.5494 | 8.8183 | 9.021 | 9.3829 | 9.3723 | 9.6369 | 8.575 | 0.3215 | 0.9675 | 0.325 |
| hsa-miR-4461 | 9.3173 | 8.9904 | 9.4639 | 9.1321 | 8.7353 | 8.9703 | 8.5194 | 8.6857 | 9.0854 | 9.0277 | 8.4839 | 0.08 | 0.8811 | 0.3324 |
| hsa-miR-500a-5p + hsa-miR-501-5p | 9.385 | 9.0147 | 9.2925 | 8.5381 | 8.1101 | 8.5359 | 7.9263 | 8.3567 | 9.2229 | 9.3349 | 7.7932 | 0.3643 | 0.9712 | 0.3398 |
| hsa-miR-183-5p | 8.9567 | 8.8492 | 9.142 | 7.5651 | 7.4754 | 8.4557 | 7.5355 | 7.7805 | 8.0563 | 8.8455 | 7.6607 | 0.4408 | 0.9761 | 0.342 |
| hsa-miR-206 | 7.6612 | 7.7802 | 7.7076 | 7.9801 | 7.3568 | 7.2333 | 6.7442 | 7.0435 | 7.8338 | 7.8455 | 7.4197 | 0.134 | 0.9254 | 0.3438 |
| hsa-miR-1182 | 8.0091 | 7.1522 | 8.1128 | 7.3337 | 7.0854 | 6.7188 | 6.6286 | 7.4586 | 7.529 | 7.9524 | 8.8672 | 0.2893 | 0.964 | 0.3462 |
| hsa-miR-638 | 8.7461 | 8.5672 | 8.2795 | 8.5106 | 7.7511 | 8.1338 | 7.6876 | 7.5227 | 8.4639 | 8.5713 | 7.7677 | 0.1937 | 0.9472 | 0.3464 |
| hsa-miR-542-5p | 8.2018 | 7.9406 | 8.5856 | 8.2025 | 7.7821 | 8.0814 | 7.5031 | 7.3915 | 7.6894 | 8.5373 | 7.5149 | 0.1501 | 0.9329 | 0.3562 |
| hsa-miR-517c-3p + hsa-miR-519a-3p | 9.2607 | 9.2676 | 9.2925 | 8.643 | 8.0088 | 8.5163 | 8.3474 | 8.7805 | 8.9173 | 8.9524 | 7.7152 | 0.2938 | 0.9645 | 0.3563 |
| hsa-miR-542-3p | 8.571 | 7.4297 | 8.6479 | 8.6928 | 7.3974 | 7.8501 | 8.8766 | 7.3915 | 8.3242 | 8.0519 | 7.2082 | 0.3293 | 0.9683 | 0.364 |
| hsa-miR-4532 | 10.2167 | 9.3839 | 9.5315 | 9.1321 | 8.437 | 8.4964 | 8.9263 | 10.9879 | 8.7991 | 8.73 | 7.8911 | 0.4962 | 0.9787 | 0.3684 |
| hsa-miR-1238 | 8.7043 | 8.5172 | 8.8019 | 8.9394 | 8.0854 | 8.3709 | 8.1098 | 7.9992 | 8.5913 | 8.6044 | 7.7677 | 0.1025 | 0.9047 | 0.3691 |
| hsa-miR-484 | 9.2167 | 8.8357 | 9.0831 | 9.3493 | 8.7973 | 8.8183 | 8.6135 | 8.2471 | 8.9807 | 9.1674 | 8.2457 | 0.0786 | 0.8792 | 0.3776 |
| hsa-miR-1178 | 10.4347 | 9.5754 | 10.068 | 9.0956 | 8.0604 | 9.0544 | 8.6876 | 9.2846 | 9.4073 | 9.6045 | 7.8911 | 0.4271 | 0.9753 | 0.3786 |
| hsa-miR-433 | 7.8647 | 7.1522 | 7.746 | 8.2696 | 7.315 | 7.3709 | 6.6286 | 6.9534 | 7.727 | 8.0992 | 6.9603 | 0.2382 | 0.9566 | 0.3796 |
| hsa-miR-874 | 7.9388 | 7.9151 | 8.142 | 7.6175 | 6.751 | 6.9115 | 6.9017 | 7.2471 | 7.6894 | 8.1894 | 6.8183 | 0.2821 | 0.9631 | 0.38 |
| hsa-miR-1305 | 7.7867 | 7.6623 | 7.4523 | 7.3951 | 6.9824 | 7.2333 | 6.9506 | 10.9879 | 7.1964 | 7.0519 | 6.9144 | 0.0441 | 0.8772 | 0.3907 |
| hsa-miR-628-5p | 7.7461 | 7.5672 | 8.253 | 8.0956 | 7.6538 | 7.4557 | 6.7442 | 6.9992 | 8.2229 | 8.1894 | 7.2082 | 0.207 | 0.9504 | 0.3932 |
| hsa-miR-1322 | 10.5237 | 9.3269 | 9.5554 | 9.2859 | 8.5673 | 8.45 | 8.3474 | 8.5227 | 10.3303 | 10.1108 | 8.575 | 0.4382 | 0.976 | 0.3944 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-450a-5p | 9.1404 | 9.0147 | 9.617 | 9.2231 | 8.4943 | 8.5163 | 8.2335 | 8.4254 | 9.4639 | 9.4849 | 8.1302 | 0.2333 | 0.9558 | 0.3948 |
| hsa-miR-802 | 7.8647 | 7.534 | 8.142 | 7.8846 | 7.1817 | 7.7188 | 7.3656 | 7.0435 | 7.8338 | 7.3929 | 6.5452 | 0.1494 | 0.9326 | 0.3988 |
| hsa-miR-381 | 8.9744 | 8.4297 | 8.8379 | 8.3337 | 7.8422 | 7.9115 | 7.5983 | 7.8572 | 8.3484 | 8.8175 | 7.9376 | 0.1663 | 0.939 | 0.4052 |
| hsa-miR-375 | 11.2534 | 10.8323 | 14.1492 | 10.1411 | 9.8641 | 10.5261 | 10.2725 | 10.5499 | 11.6388 | 12.1021 | 9.949 | 0.6451 | 0.9835 | 0.4083 |
| hsa-miR-708-5p | 7.9388 | 7.5672 | 8.8019 | 7.9801 | 7.437 | 7.2807 | 7.2916 | 7.4254 | 7.7991 | 8.393 | 7.0047 | 0.2216 | 0.9535 | 0.4126 |
| hsa-miR-299-5p | 8.3717 | 7.9151 | 8.5425 | 8.5915 | 7.315 | 7.7859 | 7.47 | 7.3568 | 8.0563 | 8.4304 | 7.2823 | 0.2051 | 0.95 | 0.4169 |
| hsa-miR-423-3p | 8.9744 | 8.4116 | 9.6066 | 8.7643 | 7.2718 | 8.3037 | 7.9979 | 8.3567 | 8.6314 | 9.2743 | 7.8183 | 0.2159 | 0.9524 | 0.4173 |
| hsa-miR-653 | 8.0091 | 7.3932 | 7.9243 | 7.8101 | 7.2718 | 7.5744 | 7.0881 | 6.906 | 7.5708 | 7.9524 | 6.4838 | 0.1485 | 0.9322 | 0.4191 |
| hsa-miR-96-5p | 9.0925 | 9.3172 | 9.9819 | 8.2364 | 8.1817 | 8.6303 | 7.825 | 8.6139 | 8.8845 | 9.2535 | 8.0478 | 0.3328 | 0.9686 | 0.4195 |
| hsa-miR-128 | 8.6612 | 8.2575 | 9.2794 | 8.1321 | 7.3974 | 7.3264 | 7.9506 | 7.8572 | 8.2995 | 8.5713 | 7.5149 | 0.2817 | 0.9631 | 0.4255 |
| hsa-miR-33a-5p | 9.3583 | 9.3557 | 9.9738 | 8.6681 | 8.4173 | 8.6484 | 8.3835 | 9.1181 | 8.8509 | 9.0758 | 8.2822 | 0.218 | 0.9528 | 0.4282 |
| hsa-miR-147a | 8.3172 | 7.7516 | 8.226 | 7.7171 | 7.7511 | 7.7527 | 7.1729 | 7.4911 | 7.7991 | 7.9524 | 6.8672 | 0.0677 | 0.8772 | 0.4467 |
| hsa-miR-378e | 11.8408 | 11.2163 | 11.604 | 11.2696 | 10.7153 | 10.9882 | 10.8413 | 10.5383 | 10.8424 | 11.6764 | 10.3949 | 0.1245 | 0.9202 | 0.4489 |
| hsa-miR-182-5p | 9.3583 | 9.4565 | 10.2463 | 8.7409 | 8.6704 | 8.5163 | 8.4187 | 8.5227 | 9.183 | 9.9652 | 8.4197 | 0.2645 | 0.9608 | 0.4569 |
| hsa-miR-301a-3p | 9.7357 | 8.6927 | 9.6978 | 9.7988 | 8.0854 | 8.7188 | 8.3656 | 8.7271 | 9.0998 | 9.2743 | 8.2641 | 0.2752 | 0.9622 | 0.4605 |
| hsa-miR-95 | 9.8836 | 9.5001 | 10.5642 | 9.565 | 8.7821 | 9.3818 | 8.851 | 9.9299 | 9.8315 | 9.8315 | 8.0896 | 0.2805 | 0.9629 | 0.4617 |
| hsa-miR-425-5p | 9.5941 | 9.0026 | 9.811 | 8.717 | 7.9554 | 7.8183 | 8.1934 | 8.7271 | 9.1558 | 9.4849 | 7.9145 | 0.3103 | 0.9664 | 0.467 |
| hsa-miR-92a-3p | 9.1246 | 8.4653 | 10.3183 | 9.2195 | 8.315 | 8.7694 | 8.1934 | 8.7271 | 8.7814 | 9.2535 | 8.0047 | 0.2866 | 0.9637 | 0.467 |
| hsa-miR-582-3p | 8.2892 | 8.2163 | 8.4754 | 7.8101 | 7.315 | 7.8183 | 7.4012 | 7.0866 | 7.6894 | 8.2325 | 7.0478 | 0.1243 | 0.9201 | 0.4752 |
| hsa-miR-154-5p | 7.8647 | 8.0146 | 8.5856 | 8.0196 | 7.2275 | 7.9412 | 7.2916 | 7.0435 | 7.4859 | 7.7889 | 7.2456 | 0.1074 | 0.9086 | 0.4763 |
| hsa-miR-193a-3p | 9.1867 | 8.7516 | 9.4754 | 8.8545 | 7.9554 | 8.5359 | 8.0437 | 8.569 | 8.5076 | 8.7597 | 7.7932 | 0.1554 | 0.935 | 0.4765 |
| hsa-miR-362-3p | 8.9918 | 8.6776 | 9.5534 | 7.7643 | 7.9554 | 8.054 | 7.4012 | 7.9764 | 8.7814 | 8.9524 | 7.4838 | 0.288 | 0.9639 | 0.4802 |
| hsa-miR-487b | 8.571 | 7.8891 | 8.253 | 8.4826 | 7.8714 | 7.5744 | 7.47 | 7.2846 | 7.727 | 8.5713 | 7.7677 | 0.0699 | 0.8772 | 0.4809 |
| hsa-miR-548v | 9.0262 | 9.119 | 8.9575 | 8.1677 | 8.2936 | 8.2807 | 8.0437 | 8.0866 | 8.5913 | 8.467 | 7.9145 | 0.0756 | 0.8772 | 0.4822 |
| hsa-miR-135a-5p | 8.8836 | 8.8492 | 9.405 | 9.302 | 8.0088 | 7.8183 | 7.9744 | 8.894 | 8.8845 | 8.9264 | 7.9145 | 0.1787 | 0.943 | 0.4877 |
| hsa-miR-500b | 8.8066 | 8.4476 | 8.5425 | 8.2025 | 7.928 | 7.684 | 7.47 | 7.7541 | 8.5501 | 8.315 | 7.5453 | 0.0621 | 0.8772 | 0.499 |
| hsa-miR-320a | 8.7253 | 8.3746 | 9.4406 | 8.454 | 7.7511 | 7.9989 | 8.066 | 7.8572 | 8.486 | 8.5026 | 7.3526 | 0.1643 | 0.9383 | 0.5052 |
| hsa-miR-764 | 9.7665 | 9.5835 | 9.8379 | 8.9599 | 8.0604 | 8.5163 | 8.5194 | 8.9299 | 9.0415 | 9.3349 | 8.0688 | 0.2298 | 0.9551 | 0.5065 |
| hsa-miR-186-5p | 9.4994 | 9.5172 | 10.746 | 8.7409 | 7.2275 | 7.7188 | 8.0437 | 8.3567 | 10.3899 | 9.3349 | 7.9827 | 0.4972 | 0.9787 | 0.5084 |
| hsa-miR-337-3p | 9.2892 | 9.0736 | 9.1985 | 9.3647 | 7.9554 | 8.5163 | 8.2725 | 8.569 | 9.0063 | 9.145 | 7.6607 | 0.1137 | 0.9133 | 0.5116 |
| hsa-miR-378a-3p + hsa-miR-378i | 10.86 | 11.6352 | 10.8775 | 9.7409 | 8.751 | 8.8656 | 8.7716 | 9.5538 | 11.3424 | 11.9427 | 8.6882 | 0.5233 | 0.9798 | 0.5122 |
| hsa-miR-27a-3p | 9.437 | 9.1522 | 10.1563 | 9.3951 | 7.7193 | 8.684 | 8.3291 | 8.5991 | 9.0563 | 9.4304 | 7.7932 | 0.2975 | 0.965 | 0.5233 |
| hsa-miR-451a | 13.822 | 14.3154 | 14.4432 | 10.8491 | 12.1223 | 10.531 | 10.1934 | 12.2244 | 14.8263 | 14.8293 | 12.9021 | 0.6378 | 0.9834 | 0.526 |
| hsa-miR-489 | 9.9477 | 9.7298 | 9.4754 | 8.8976 | 8.437 | 8.9558 | 8.7441 | 8.6574 | 8.8845 | 9.145 | 8.2271 | 0.1376 | 0.9272 | 0.5285 |
| hsa-miR-31-5p | 9.1867 | 9.062 | 11.1456 | 8.643 | 7.9824 | 8.5359 | 7.8766 | 8.5841 | 9.236 | 9.5713 | 8.2082 | 0.3991 | 0.9737 | 0.5352 |
| hsa-miR-604 | 9.7767 | 9.4915 | 9.8731 | 9.38 | 8.7353 | 8.8656 | 8.7579 | 9.1691 | 9.128 | 9.2535 | 8.3179 | 0.063 | 0.8772 | 0.536 |
| hsa-miR-197-3p | 8.4497 | 7.9904 | 8.6879 | 9.8976 | 8.336 | 8.1338 | 8.066 | 8.507 | 8.2229 | 8.6686 | 7.2082 | 0.207 | 0.9504 | 0.5379 |
| hsa-miR-573 | 9.3982 | 9.0503 | 9.3561 | 8.6175 | 7.8422 | 8.3265 | 8.1098 | 8.7406 | 8.5913 | 8.6996 | 7.4197 | 0.1688 | 0.9399 | 0.5383 |
| hsa-miR-193b-3p | 9.5357 | 9.085 | 9.916 | 9.9497 | 8.4563 | 9.1338 | 8.4699 | 9.0215 | 8.8509 | 9.2535 | 8.3526 | 0.1378 | 0.9273 | 0.5415 |
| hsa-miR-377-3p | 8.5476 | 8.3557 | 8.6879 | 8.8976 | 7.7511 | 7.8501 | 7.5355 | 7.643 | 8.6314 | 8.3545 | 7.4197 | 0.0832 | 0.8852 | 0.5423 |
| hsa-miR-3147 | 9.8836 | 10.237 | 10.286 | 9.1321 | 8.5494 | 8.9412 | 8.7852 | 9.5149 | 9.4188 | 9.5026 | 8.2082 | 0.2062 | 0.9502 | 0.5558 |
| hsa-miR-185-5p | 9.4112 | 9.2575 | 10.1054 | 8.6928 | 8.0854 | 8.6663 | 8.4699 | 8.3567 | 9.287 | 9.0992 | 8.0478 | 0.1374 | 0.9271 | 0.5559 |
| hsa-miR-877-5p | 9.5476 | 8.8904 | 8.6879 | 8.058 | 8.585 | 8.0544 | 8.1522 | 8.189 | 8.0265 | 8.73 | 7.5453 | 0.1312 | 0.924 | 0.5576 |
| hsa-miR-193a-5p | 8.4994 | 8.1521 | 9.2794 | 8.9599 | 7.9554 | 8.1338 | 7.6286 | 7.6716 | 8.5076 | 8.467 | 7.6041 | 0.0988 | 0.9015 | 0.5671 |
| hsa-miR-362-3p | 9.0925 | 8.5996 | 9.3436 | 8.9801 | 7.7511 | 7.8811 | 7.4012 | 8.491 | 8.5913 | 8.9524 | 7.7932 | 0.1574 | 0.9358 | 0.5683 |
| hsa-miR-181c-5p | 8.4748 | 7.9904 | 9.331 | 8.2364 | 7.6869 | 7.4557 | 7.2916 | 8.0653 | 8.142 | 8.393 | 7.2456 | 0.1335 | 0.9252 | 0.5784 |
| hsa-miR-200c-3p | 14.5252 | 14.5458 | 15.5791 | 11.1455 | 11.8605 | 12.1641 | 12.4825 | 12.8454 | 14.2278 | 14.5336 | 11.3845 | 0.5707 | 0.9814 | 0.5916 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-127-3p | 9.7253 | 9.3269 | 9.7649 | 9.9394 | 8.336 | 8.3488 | 8.4699 | 8.4749 | 9.9572 | 9.3149 | 8.3866 | 0.1688 | 0.9399 | 0.5931 |
| hsa-miR-4284 | 10.365 | 9.4115 | 9.5425 | 8.565 | 7.928 | 8.1338 | 8.066 | 9.6716 | 8.6895 | 8.7597 | 7.9145 | 0.251 | 0.9587 | 0.6232 |
| hsa-miR-299-3p | 8.6392 | 8.5507 | 9.0679 | 8.454 | 7.7821 | 7.9115 | 7.5031 | 7.4911 | 8.4639 | 8.6044 | 7.2456 | 0.072 | 0.8772 | 0.6288 |
| hsa-miR-107 | 10.0598 | 9.4297 | 10.6879 | 9.8436 | 8.4173 | 8.8342 | 8.6286 | 9.1077 | 9.5396 | 9.8315 | 8.4032 | 0.1958 | 0.9477 | 0.6302 |
| hsa-miR-152 | 9.3583 | 8.8492 | 8.8556 | 9.6556 | 8.6537 | 8.5163 | 8.4187 | 8.4254 | 9.142 | 9.2535 | 8.11 | 0.0644 | 0.8772 | 0.6302 |
| hsa-miR-660-5p | 9.3447 | 9.119 | 9.9899 | 8.7874 | 7.6538 | 8.3265 | 7.5983 | 8.5227 | 8.9961 | 8.9264 | 7.7152 | 0.208 | 0.9506 | 0.6314 |
| hsa-miR-601 | 10.2534 | 10.1246 | 9.811 | 8.7409 | 8.0088 | 8.5932 | 8.436 | 9.643 | 8.5708 | 8.9779 | 8.2641 | 0.2334 | 0.9558 | 0.6402 |
| hsa-miR-574-5p | 10.4933 | 10.3074 | 11.408 | 9.6175 | 8.8422 | 8.9558 | 9.1832 | 9.6285 | 8.5708 | 10.0875 | 8.4839 | 0.2563 | 0.9596 | 0.6522 |
| hsa-miR-10a-5p | 11.4402 | 9.9407 | 13.5662 | 9.6556 | 9.0219 | 8.8022 | 8.6436 | 9.2938 | 11.6918 | 12.467 | 9.5302 | 0.549 | 0.9807 | 0.6535 |
| hsa-miR-361-3p | 9.9655 | 9.2163 | 10.7742 | 9.0581 | 8.4754 | 8.6663 | 8.5672 | 8.5991 | 9.2744 | 9.6686 | 8.2282 | 0.195 | 0.9475 | 0.6549 |
| hsa-miR-421 | 8.9567 | 8.9151 | 9.2396 | 8.454 | 7.8422 | 7.7527 | 7.8766 | 8.2846 | 8.5708 | 8.2743 | 7.3866 | 0.0627 | 0.8772 | 0.6572 |
| hsa-miR-337-5p | 8.6612 | 8.2575 | 8.8904 | 8.9187 | 7.437 | 7.9115 | 7.5983 | 7.5227 | 8.142 | 8.145 | 7.2823 | 0.0752 | 0.8772 | 0.666 |
| hsa-miR-454-3p | 9.7665 | 8.6927 | 10.0138 | 8.8976 | 8.1344 | 8.3926 | 7.9506 | 8.3211 | 9.0709 | 9.0277 | 7.8183 | 0.1458 | 0.931 | 0.6708 |
| hsa-miR-32-5p | 9.7665 | 9.1078 | 10.6978 | 9.2195 | 8.1582 | 8.5163 | 7.825 | 9.2566 | 9.0563 | 9.7449 | 7.9145 | 0.2351 | 0.9561 | 0.671 |
| hsa-miR-331-3p | 9.5116 | 9.1739 | 10.286 | 9.6928 | 8.4754 | 8.3488 | 8.4187 | 8.918 | 9.0415 | 9.2535 | 8.4994 | 0.0884 | 0.8911 | 0.6813 |
| hsa-miR-214-3p | 9.7148 | 8.7802 | 9.916 | 10.3415 | 8.5494 | 8.6303 | 8.4866 | 8.569 | 8.9807 | 9.4488 | 8.5149 | 0.1196 | 0.9172 | 0.6887 |
| hsa-miR-221-3p | 9.2892 | 9.3366 | 10.4465 | 9.8436 | 8.3773 | 9.1968 | 8.1934 | 8.4668 | 8.8509 | 9.003 | 7.8429 | 0.1399 | 0.9283 | 0.6996 |
| hsa-miR-151a-3p | 9.8456 | 9.7872 | 11.1275 | 9.6681 | 8.2725 | 8.3926 | 8.2725 | 8.8447 | 10.651 | 9.8999 | 8.11 | 0.2887 | 0.9639 | 0.7027 |
| hsa-miR-196a-5p | 9.6168 | 9.8357 | 10.8904 | 8.3951 | 7.8714 | 8.3488 | 8.173 | 7.9299 | 9.529 | 9.7449 | 7.8183 | 0.2883 | 0.9639 | 0.7312 |
| hsa-miR-151a-5p | 9.3982 | 9.237 | 10.3623 | 9.3337 | 8.585 | 8.5163 | 8.5983 | 8.6574 | 9.0709 | 9.0992 | 7.9603 | 0.0647 | 0.8772 | 0.7329 |
| hsa-miR-135b-5p | 11.1206 | 10.9873 | 12.849 | 8.9394 | 8.4754 | 9.2807 | 8.6436 | 10.503 | 10.5657 | 10.7671 | 8.6745 | 0.4414 | 0.9761 | 0.7353 |
| hsa-miR-187-3p | 9.3583 | 9.6391 | 9.8556 | 8.8325 | 8.6369 | 8.7188 | 8.2725 | 8.303 | 8.9651 | 8.8455 | 7.9603 | 0.0304 | 0.8772 | 0.7536 |
| hsa-miR-518b | 10.7201 | 9.6235 | 11.2158 | 9.1187 | 8.7667 | 8.8963 | 9.0095 | 8.9534 | 9.8166 | 10.0758 | 9.0047 | 0.1643 | 0.9383 | 0.7562 |
| hsa-miR-155-5p | 11.1942 | 10.1952 | 11.683 | 9.1852 | 7.585 | 8.7188 | 9.1417 | 9.1285 | 9.3242 | 10.3738 | 8.5301 | 0.3713 | 0.9717 | 0.7657 |
| hsa-miR-25-3p | 11.86 | 11.6604 | 12.9348 | 11.3876 | 10.2275 | 10.3151 | 10.1832 | 11.2892 | 11.7702 | 11.7816 | 9.6814 | 0.2069 | 0.9504 | 0.7772 |
| hsa-miR-1290 | 9.3583 | 8.7802 | 8.4754 | 7.5651 | 7.1344 | 7.684 | 6.7442 | 7.8065 | 7.4859 | 7.73 | 7.4197 | 0.1284 | 0.9224 | 0.7843 |
| hsa-miR-455-5p | 8.9206 | 8.9781 | 10.5886 | 8.2696 | 7.8124 | 7.7859 | 7.436 | 7.906 | 9.0563 | 8.8175 | 7.6688 | 0.1876 | 0.9456 | 0.7983 |
| hsa-miR-582-5p | 8.9567 | 9.0736 | 9.5749 | 8.7409 | 7.8124 | 7.414 | 7.2916 | 7.9534 | 8.5913 | 9.0519 | 7.8911 | 0.078 | 0.8784 | 0.7995 |
| hsa-miR-15b-5p | 12.5622 | 12.0236 | 12.6743 | 11.5684 | 10.2664 | 11.3293 | 9.9744 | 12.1116 | 10.7177 | 11.8489 | 10.0998 | 0.1931 | 0.947 | 0.8054 |
| hsa-miR-146b-5p | 8.4994 | 8.3746 | 9.6978 | 8.1677 | 7.585 | 7.5359 | 7.0881 | 7.6996 | 7.727 | 8.5026 | 7.3526 | 0.0832 | 0.8852 | 0.8139 |
| hsa-miR-196a-5p | 11.1829 | 10.3792 | 9.9657 | 8.3647 | 7.928 | 8.3709 | 7.9744 | 7.9534 | 9.6895 | 10.0277 | 8.3526 | 0.2831 | 0.9633 | 0.836 |
| hsa-miR-320e | 10.3717 | 10.6623 | 10.994 | 9.7759 | 8.969 | 8.85 | 9.2628 | 9.5614 | 9.9092 | 9.5373 | 8.7805 | 0.0815 | 0.883 | 0.8377 |
| hsa-miR-1260a | 13.7735 | 13.342 | 14.0957 | 13.76 | 12.8367 | 14.0776 | 13.6268 | 15.1302 | 11.6461 | 12.3786 | 9.4032 | 0.3624 | 0.9711 | 0.8511 |
| hsa-miR-664-3p | 9.5593 | 8.822 | 0.746 | 9.5783 | 8.2719 | 8.4139 | 8.1522 | 8.9649 | 8.8166 | 9.145 | 7.7152 | 0.1165 | 0.9152 | 0.8609 |
| hsa-miR-574-3p | 9.9206 | 9.1412 | 10.3868 | 10.8101 | 9.585 | 8.8663 | 8.8766 | 9.0104 | 9.4416 | 9.7597 | 8.4994 | 0.0404 | 0.8772 | 0.8687 |
| hsa-miR-20a-5p + hsa-miR-20b-5p | 11.2714 | 10.9688 | 12.2413 | 9.643 | 7.9554 | 9.3926 | 8.8381 | 10.0653 | 10.0854 | 10.393 | 8.4522 | 0.3222 | 0.9676 | 0.8783 |
| hsa-miR-340-5p | 8.8456 | 8.1301 | 9.811 | 8.8545 | 7.437 | 7.684 | 7.2136 | 7.3915 | 8.2489 | 8.393 | 7.4838 | 0.0953 | 0.8982 | 0.8798 |
| hsa-miR-548aa | 10.6502 | 10.7225 | 10.8335 | 9.565 | 8.1344 | 10.02 | 8.4866 | 10.5804 | 8.8166 | 8.873 | 7.8183 | 0.2189 | 0.953 | 0.882 |
| hsa-miR-28-3p | 9.8456 | 10.0735 | 11.1599 | 10.0675 | 8.5313 | 8.5744 | 8.5355 | 8.7271 | 10.3364 | 9.8032 | 8.3353 | 0.1372 | 0.927 | 0.8836 |
| hsa-miR-10b-5p | 9.9114 | 9.1078 | 10.2463 | 9.5783 | 8.2936 | 7.8183 | 8.2136 | 8.5227 | 9.2489 | 9.4849 | 7.9145 | 0.0771 | 0.8772 | 0.8937 |
| hsa-miR-324-5p | 9.5826 | 9.3557 | 10.5696 | 9.8436 | 7.5494 | 8.684 | 8.4012 | 8.906 | 8.7814 | 9.0277 | 7.0478 | 0.1666 | 0.9391 | 0.9055 |
| hsa-miR-4488 | 12.7942 | 11.3581 | 11.2827 | 10.0293 | 9.1817 | 9.8963 | 10.5828 | 13.256 | 8.9651 | 9.2111 | 8.2082 | 0.3657 | 0.9713 | 0.9093 |
| hsa-miR-181b-5p + hsa-miR-181d | 9.0762 | 8.6927 | 9.5642 | 8.6175 | 8.0088 | 7.7527 | 7.5983 | 7.1285 | 8.6314 | 8.467 | 7.7152 | 0.0285 | 0.8772 | 0.9097 |
| hsa-miR-146a-5p | 10.6112 | 9.8151 | 11.0943 | 9.729 | 8.9279 | 8.5932 | 8.851 | 9.4338 | 9.6607 | 9.8315 | 8.3001 | 0.0793 | 0.8801 | 0.9238 |
| hsa-miR-19b-3p | 11.0304 | 10.8357 | 12.3561 | 10.2696 | 8.7973 | 9.4245 | 8.7302 | 10.499 | 10.4472 | 10.8865 | 8.3866 | 0.2317 | 0.9555 | 0.9288 |
| hsa-miR-1233 | 8.9567 | 8.766 | 9.6479 | 10.4101 | 8.2936 | 8.0814 | 8.3835 | 8.1285 | 8.3723 | 9.0277 | 7.7152 | 0.0653 | 0.8772 | 0.9301 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-365a-3p | 8.4994 | 8.4116 | 10.0906 | 9.7526 | 8.1582 | 8.3488 | 7.2916 | 8.1285 | 8.4415 | 8.5373 | 7.5453 | 0.0784 | 0.879 | 0.9336 |
| hsa-miR-1973 | 10.7409 | 10.0326 | 9.82 | 8.5915 | 8.1582 | 8.3265 | 8.4187 | 9.5149 | 8.4639 | 8.9779 | 7.4521 | 0.1349 | 0.9259 | 0.943 |
| hsa-miR-376c | 9.5593 | 9.062 | 9.6879 | 9.7988 | 8.1817 | 8.0814 | 8.2531 | 8.3567 | 8.7814 | 8.6996 | 7.7152 | 0.0301 | 0.8772 | 0.9434 |
| hsa-miR-136-5p | 9.1087 | 8.8492 | 9.405 | 9.039 | 6.9824 | 7.684 | 7.2136 | 7.5227 | 8.2995 | 8.5026 | 7.1697 | 0.1004 | 0.9029 | 0.9448 |
| hsa-miR-1253 | 2.6159 | 2.1077 | 6.5856 | 2.8094 | 2.2265 | 2.3277 | 2.0426 | 2 | 2.441 | 3.1457 | 1.9598 | 0.3257 | 0.9679 | 0.9496 |
| hsa-miR-93-5p | 11.6963 | 11.4498 | 12.6235 | 10.2195 | 9.0219 | 9.1466 | 9.173 | 10.2938 | 11.236 | 11.4211 | 9.0156 | 0.252 | 0.9589 | 0.9545 |
| hsa-miR-200b-3p | 13.7344 | 14.1498 | 15.3189 | 10.2696 | 11.5539 | 10.4298 | 10.5113 | 12.3764 | 14.0831 | 13.7771 | 10.9603 | 0.4127 | 0.9745 | 0.9823 |
| hsa-miR-99b-5p | 10.0762 | 9.7516 | 10.9698 | 10.9343 | 9.1223 | 8.5163 | 9.2136 | 9.1077 | 9.9651 | 10.0398 | 8.1501 | 0.0628 | 0.8772 | 1.0054 |
| hsa-miR-141-3p | 12.2875 | 12.5086 | 14.1451 | 9.38 | 9.8857 | 9.7443 | 9.4866 | 11.3501 | 11.7657 | 12.0905 | 9.309 | 0.3544 | 0.9704 | 1.017 |
| hsa-miR-148b-3p | 10.8893 | 10.2473 | 11.3746 | 11.0147 | 9.0219 | 9.2213 | 8.6286 | 9.9707 | 9.9414 | 10.5201 | 8.6468 | 0.0867 | 0.8893 | 1.0193 |
| hsa-miR-137 | 11.6936 | 13.8323 | 13.4406 | 8.8325 | 9.1223 | 8.9703 | 9.0771 | 10.6538 | 11.1175 | 11.4165 | 8.5301 | 0.3482 | 0.9699 | 1.0234 |
| hsa-miR-204-5p | 8.7253 | 8.5996 | 10.3498 | 8.3951 | 7.9824 | 7.6484 | 7.2916 | 7.6996 | 8.2995 | 8.145 | 7.4838 | 0.0585 | 0.8772 | 1.0491 |
| hsa-miR-191-5p | 12.2334 | 11.9564 | 12.8568 | 12.0793 | 10.1875 | 9.6663 | 10.0152 | 10.5538 | 11.9592 | 12.5629 | 9.9318 | 0.1369 | 0.9269 | 1.0811 |
| hsa-miR-429 | 11.3033 | 11.7766 | 12.1438 | 8.8545 | 9.2498 | 8.8656 | 8.3105 | 10.0215 | 10.8079 | 10.7671 | 8.5301 | 0.2125 | 0.9516 | 1.1152 |
| hsa-miR-148a-3p | 12.8777 | 12.4104 | 13.1146 | 11.7497 | 9.6869 | 9.9264 | 9.6584 | 11.6786 | 11.9092 | 12.0728 | 9.8672 | 0.1876 | 0.9456 | 1.1158 |
| hsa-miR-28-5p | 10.3447 | 9.9151 | 11.4377 | 10.9187 | 8.7194 | 8.8022 | 8.7441 | 8.7541 | 9.7991 | 10.1337 | 8.6185 | 0.0768 | 0.8772 | 1.1252 |
| hsa-miR-338-3p | 10.6775 | 9.8627 | 11.0138 | 11.2067 | 8.751 | 8.4762 | 7.9744 | 8.6285 | 9.901 | 11.4258 | 8.6185 | 0.1348 | 0.9258 | 1.1316 |
| hsa-miR-3195 | 9.3173 | 8.5507 | 9.3054 | 7.9394 | 7.9824 | 7.6118 | 7.2136 | 7.3211 | 7.901 | 8.2325 | 6.6042 | 0.0177 | 0.8772 | 1.1383 |
| hsa-miR-218-5p | 9.1714 | 8.2163 | 10.9327 | 9.2531 | 7.8714 | 7.7527 | 7.8511 | 7.9299 | 8.486 | 8.1894 | 7.4838 | 0.0988 | 0.9015 | 1.1401 |
| hsa-miR-4508 | 11.4592 | 11.1549 | 11.1383 | 9.6303 | 9.4659 | 9.4139 | 9.6361 | 9.4749 | 9.5708 | 9.6045 | 8.7932 | 0.0497 | 0.8772 | 1.1541 |
| hsa-miR-22-3p | 11.4145 | 12.0011 | 12.3669 | 11.1276 | 9.2275 | 9.172 | 8.9263 | 10.0104 | 11.1245 | 12.1337 | 9.0371 | 0.1633 | 0.938 | 1.1602 |
| hsa-miR-30d-5p | 11.0598 | 10.6469 | 12.411 | 10.8545 | 9.1582 | 8.8811 | 8.8892 | 9.507 | 11.5022 | 10.9066 | 8.2271 | 0.146 | 0.9312 | 1.1739 |
| hsa-miR-132-3p | 10.0262 | 9.0266 | 9.5315 | 10.3724 | 8.4173 | 7.9115 | 8.0437 | 8.303 | 8.6704 | 9.0519 | 7.6882 | 0.0227 | 0.8772 | 1.1967 |
| hsa-miR-194-5p | 14.4968 | 14.6721 | 15.6572 | 10.86 | 12.6284 | 8.0544 | 10.3429 | 12.5383 | 14.7422 | 16.1826 | 12.9369 | 0.4386 | 0.976 | 1.1967 |
| hsa-miR-1 | 9.2607 | 8.766 | 11.0755 | 10.4175 | 8.2719 | 7.9989 | 8.2531 | 8.1691 | 8.7083 | 8.8999 | 8.11 | 0.081 | 0.8823 | 1.2017 |
| hsa-miR-192-5p | 13.0587 | 13.6136 | 14.5971 | 9.9187 | 11.0604 | 9.013 | 9.673 | 10.921 | 12.8783 | 14.0534 | 10.9145 | 0.3254 | 0.9679 | 1.2075 |
| hsa-miR-1469 | 11.3515 | 10.062 | 9.0831 | 8.5381 | 7.8124 | 8.1078 | 8.6135 | 9.1988 | 7.8678 | 7.8999 | 7.2456 | 0.1262 | 0.9212 | 1.2138 |
| hsa-miR-15a-5p | 12.3982 | 12.2267 | 13.6561 | 11.8923 | 9.6704 | 10.1907 | 9.2531 | 11.6249 | 11.5049 | 12.1422 | 9.8058 | 0.1699 | 0.9402 | 1.2151 |
| hsa-miR-106a-5p + hsa-miR-17-5p | 12.1752 | 11.4093 | 12.7245 | 10.2448 | 8.6869 | 9.7188 | 9.3475 | 10.3915 | 10.2424 | 10.5544 | 8.6041 | 0.1704 | 0.9404 | 1.2383 |
| hsa-miR-106b-5p | 11.6447 | 11.5235 | 12.5802 | 9.454 | 8.315 | 8.8656 | 8.5672 | 9.8757 | 10.3119 | 10.5629 | 8.6041 | 0.2052 | 0.95 | 1.2389 |
| hsa-miR-720 | 16.9648 | 16.4432 | 17.309 | 17.1436 | 16.5724 | 17.0344 | 16.4224 | 15.5944 | 14.8499 | 16.1911 | 13.7825 | 0.0495 | 0.8772 | 1.2408 |
| hsa-miR-423-5p | 9.9297 | 9.8826 | 11.0295 | 9.6681 | 8.6025 | 8.1844 | 8.4012 | 8.0215 | 9.0265 | 9.8315 | 8.0047 | 0.034 | 0.8772 | 1.2442 |
| hsa-miR-376a-3p | 10.1482 | 10.0793 | 10.6428 | 10.6928 | 8.4943 | 8.2572 | 8.6584 | 8.8447 | 9.3484 | 9.2948 | 8.1891 | 0.0318 | 0.8772 | 1.246 |
| hsa-miR-133a | 8.7043 | 8.1301 | 10.6014 | 10.211 | 8.0088 | 7.684 | 7.5355 | 7.8321 | 8.0854 | 8.6369 | 7.4197 | 0.0769 | 0.8772 | 1.2655 |
| hsa-miR-30e-5p | 9.1867 | 8.5001 | 10.7835 | 10.2448 | 7.9824 | 7.9703 | 7.5673 | 7.8816 | 8.6486 | 8.73 | 7.6607 | 0.0677 | 0.8772 | 1.2901 |
| hsa-miR-98 | 10.4748 | 9.9151 | 11.537 | 9.7409 | 8.0854 | 8.5553 | 7.9979 | 9.0544 | 8.9807 | 9.467 | 7.7677 | 0.0811 | 0.8825 | 1.3135 |
| hsa-miR-200a-3p | 12.7396 | 12.6871 | 14.4347 | 9.7874 | 11.2499 | 9.5359 | 9.6657 | 11.3323 | 12.4373 | 12.4095 | 10.9145 | 0.2108 | 0.9513 | 1.3153 |
| hsa-miR-30e-5p | 11.2998 | 11.2448 | 12.8268 | 11.0049 | 9.4943 | 9.2923 | 9.2236 | 9.6927 | 11.1385 | 10.9066 | 8.7677 | 0.0785 | 0.8791 | 1.3372 |
| hsa-miR-24-3p | 11.1087 | 10.5996 | 12.1846 | 10.6175 | 8.437 | 9.2572 | 8.79986 | 10.3435 | 9.5605 | 9.8315 | 7.6882 | 0.1044 | 0.9063 | 1.3429 |
| hsa-let-7d-5p | 11.6392 | 11.1738 | 12.526 | 10.6743 | 9.1101 | 9.2334 | 9.1417 | 9.9534 | 10.1763 | 10.6764 | 8.8672 | 0.078 | 0.8784 | 1.35 |
| hsa-miR-140-5p | 10.2679 | 9.8357 | 11.2925 | 9.6175 | 8.0088 | 7.9989 | 8.0437 | 8.2846 | 9.2744 | 9.1223 | 7.8183 | 0.0596 | 0.8772 | 1.3808 |
| hsa-miR-502-5p | 10.6883 | 10.5465 | 10.2663 | 8.8976 | 7.9554 | 8.435 | 8.021 | 7.8321 | 8.5076 | 8.7889 | 7.8672 | 0.0532 | 0.8772 | 1.4289 |
| hsa-miR-374b-5p | 10.5593 | 10.3172 | 11.8087 | 10.3258 | 8.6537 | 8.4139 | 8.436 | 9.0544 | 9.5396 | 9.8455 | 8.0264 | 0.0438 | 0.8772 | 1.447 |
| hsa-miR-16-5p | 13.2534 | 13.0296 | 14.5483 | 11.7438 | 10.2105 | 10.3926 | 9.9079 | 11.7237 | 11.8636 | 12.6705 | 9.8058 | 0.1324 | 0.9246 | 1.4965 |
| hsa-miR-222-3p | 12.7227 | 11.9247 | 13.517 | 11.0816 | 10.2554 | 9.684 | 9.8381 | 10.8289 | 11.5553 | 11.1337 | 9.1202 | 0.0611 | 0.8772 | 1.5403 |
| hsa-miR-195-5p | 10.4872 | 9.5835 | 11.6402 | 10.8045 | 8.315 | 8.3488 | 8.4187 | 8.6857 | 9.0563 | 9.3149 | 7.8672 | 0.0497 | 0.8772 | 1.5508 |
| hsa-miR-374a-5p | 12.9929 | 12.2689 | 13.8059 | 12.8073 | 10.17 | 10.153 | 9.5751 | 11.6609 | 11.8424 | 12.0368 | 9.8368 | 0.0762 | 0.8772 | 1.5582 |

TABLE 1-continued

Results from 800 miRNA tested

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-4454 | 20.6902 | 20.4538 | 20.9389 | 19.1773 | 17.4403 | 18.7722 | 18.3003 | 19.7471 | 18.8923 | 18.8484 | 14.5201 | 0.1523 | 0.9338 | 1.56 |
| hsa-miR-125a-5p | 10.7564 | 9.7731 | 11.6066 | 12.0955 | 9.6025 | 8.4964 | 9.3383 | 9.7065 | 10.2489 | 9.8174 | 7.5149 | 0.0379 | 0.8772 | 1.5798 |
| hsa-miR-34a-5p | 11.456 | 11.0936 | 12.0334 | 12.2025 | 9.1223 | 9.2807 | 8.8892 | 10.5149 | 10.3604 | 10.2111 | 7.9827 | 0.0448 | 0.8772 | 1.6417 |
| hsa-miR-497-5p | 9.2462 | 8.7371 | 10.5554 | 9.039 | 7.3568 | 6.85 | 6.6286 | 7.4911 | 8.2229 | 8.315 | 6.5452 | 0.0302 | 0.8772 | 1.6444 |
| hsa-miR-29a-3p | 12.0241 | 12.3955 | 13.9534 | 11.228 | 9.2162 | 9.2334 | 8.9744 | 10.9736 | 11.4044 | 11.4024 | 8.6745 | 0.1191 | 0.9169 | 1.653 |
| hsa-let-7g-5p | 14.7115 | 14.5494 | 15.899 | 14.0281 | 11.4049 | 11.5539 | 11.3835 | 13.3177 | 13.2513 | 13.9763 | 11.0344 | 0.0988 | 0.9015 | 1.702 |
| hsa-miR-1915-3p | 10.7666 | 10.0444 | 10.4981 | 9.729 | 8.7194 | 8.2334 | 8.5355 | 8.9992 | 8.529 | 7.8455 | 7.3179 | 0.005 | 0.8772 | 1.7081 |
| hsa-miR-361-5p | 10.4994 | 9.8826 | 11.6953 | 10.5783 | 8.5313 | 8.2807 | 8.2136 | 9.1489 | 8.8339 | 9.3149 | 7.3179 | 0.0256 | 0.8772 | 1.7191 |
| hsa-miR-575 | 11.8906 | 12.3855 | 11.8644 | 9.8101 | 8.5673 | 8.8342 | 9.8892 | 9.8757 | 9.7453 | 9.0758 | 7.9145 | 0.0851 | 0.8875 | 1.7212 |
| hsa-let-7f-5p | 11.7842 | 11.6547 | 13.3561 | 10.9239 | 8.9957 | 9.2334 | 8.4531 | 10.2086 | 9.901 | 10.9524 | 8.7018 | 0.069 | 0.8772 | 1.7679 |
| hsa-miR-630 | 12.9644 | 13.3972 | 12.0527 | 10.4322 | 8.8714 | 9.3926 | 10.0935 | 11.2183 | 10.0926 | 9.2948 | 8.5149 | 0.1053 | 0.907 | 1.7758 |
| hsa-miR-181a-5p | 11.5623 | 11.5403 | 13.0217 | 10.5717 | 9.1344 | 7.7527 | 8.4531 | 9.499 | 12.0171 | 10.6045 | 7.8911 | 0.0884 | 0.8912 | 1.7965 |
| hsa-let-7i-5p | 11.8552 | 11.4631 | 13.0859 | 11.3219 | 8.8124 | 9.1209 | 8.7579 | 9.9061 | 10.0782 | 10.7597 | 8.436 | 0.0613 | 0.8772 | 1.7979 |
| hsa-miR-342-3p | 12.1364 | 10.9054 | 13.046 | 12.8422 | 10.4124 | 9.7359 | 9.992 | 10.6857 | 10.2229 | 10.6449 | 8.9827 | 0.0207 | 0.8772 | 1.8245 |
| hsa-let-7c | 12.1848 | 11.4229 | 12.9586 | 11.9055 | 8.4943 | 9.4964 | 9.099 | 10.4043 | 9.6989 | 10.3545 | 8.2822 | 0.0742 | 0.8772 | 1.8373 |
| hsa-miR-29c-3p | 11.7122 | 11.515 | 13.6177 | 11.294 | 9.1817 | 8.8656 | 8.9625 | 9.7271 | 10.9294 | 10.7224 | 8.4994 | 0.0608 | 0.8772 | 1.8464 |
| hsa-miR-223-3p | 11.8456 | 10.7298 | 12.2729 | 11.7409 | 9.9486 | 8.5553 | 8.7302 | 9.7871 | 10.5553 | 10.3642 | 8.7677 | 0.01 | 0.8772 | 1.8476 |
| hsa-let-7b-5p | 15.3961 | 14.7346 | 16.1304 | 14.3805 | 12.2623 | 11.9989 | 12.6145 | 13.1995 | 13.6776 | 14.1036 | 10.6256 | 0.0537 | 0.8772 | 1.8775 |
| hsa-miR-199a-5p | 10.6721 | 9.6235 | 11.8357 | 11.2737 | 8.5494 | 7.684 | 8.3656 | 8.8065 | 8.9961 | 9.4118 | 7.7932 | 0.029 | 0.8772 | 1.8813 |
| hsa-let-7a-5p | 16.3279 | 15.6121 | 17.2522 | 14.9618 | 12.4825 | 12.9766 | 12.8234 | 14.275 | 14.1588 | 14.7351 | 11.6131 | 0.0848 | 0.8871 | 1.897 |
| hsa-miR-27b-3p | 12.0241 | 12.0721 | 13.7701 | 12.6712 | 8.7353 | 10.435 | 9.3835 | 11.6176 | 10.2933 | 9.9524 | 7.9827 | 0.0934 | 0.8964 | 1.9105 |
| hsa-miR-30b-5p | 12.5898 | 11.8908 | 13.8715 | 12.4594 | 9.9348 | 9.9847 | 9.1832 | 10.8225 | 10.529 | 11.7149 | 9.16 | 0.0397 | 0.8772 | 1.9169 |
| hsa-miR-23a-3p | 14.3646 | 13.7727 | 15.6204 | 14.511 | 11.3176 | 11.7231 | 11.3198 | 13.5813 | 12.5798 | 12.6938 | 9.5897 | 0.0592 | 0.8772 | 2.0027 |
| hsa-miR-30a-5p | 11.7538 | 11.3462 | 12.7578 | 11.5036 | 9.0088 | 8.3488 | 8.4866 | 9.3301 | 11.3986 | 10.1108 | 7.8911 | 0.0376 | 0.8772 | 2.013 |
| hsa-miR-4286 | 13.7357 | 12.0326 | 13.5093 | 11.598 | 9.4943 | 9.5163 | 10.7476 | 12.612 | 10.1964 | 9.3545 | 7.9376 | 0.077 | 0.8772 | 2.0133 |
| hsa-miR-21-5p | 15.2471 | 15.5306 | 14.1215 | 13.9956 | 12.5528 | 11.2894 | 11.6712 | 13.0188 | 10.5553 | 14.9028 | 11.9687 | 0.0632 | 0.8772 | 2.0321 |
| hsa-miR-23b-3p | 13.4779 | 12.7793 | 14.6434 | 14.0024 | 12.2623 | 11.2183 | 10.6694 | 12.6618 | 11.2031 | 11.2588 | 8.7677 | 0.0599 | 0.8772 | 2.0595 |
| hsa-miR-29b-3p | 15.0008 | 14.403 | 16.1465 | 14.1633 | 11.9622 | 11.2453 | 10.9171 | 13.2823 | 13.5224 | 13.5744 | 11.0688 | 0.0448 | 0.8772 | 2.0667 |
| hsa-miR-100-5p | 11.6748 | 11.0116 | 12.6014 | 12.4684 | 8.751 | 8.0544 | 9.0437 | 9.2846 | 10.7814 | 9.8032 | 7.8911 | 0.0352 | 0.8772 | 2.1584 |
| hsa-miR-199b-5p | 10.8976 | 9.9595 | 12.4711 | 11.9901 | 8.7032 | 7.8811 | 7.9506 | 8.7271 | 9.4388 | 9.6842 | 7.4838 | 0.0384 | 0.8772 | 2.2024 |
| hsa-miR-99a-5p | 12.7162 | 11.8151 | 13.3662 | 13.183 | 9.2719 | 10.1013 | 9.4274 | 11.2376 | 10.2617 | 9.8593 | 7.7932 | 0.0532 | 0.8772 | 2.2188 |
| hsa-miR-130a-3p | 11.5652 | 10.7114 | 12.5037 | 11.9471 | 12.1744 | 11.8422 | 12.2773 | 9.8572 | 9.8252 | 9.2535 | 7.0478 | 0.0227 | 0.8772 | 2.2258 |
| hsa-miR-266-5p | 12.924 | 11.9038 | 14.1215 | 11.8353 | 10.9723 | 10.1845 | 10.3383 | 10.7305 | 10.6065 | 10.8524 | 8.4681 | 0.0451 | 0.8772 | 2.2353 |
| hsa-let-7e-5p | 10.9962 | 10.3835 | 12.1017 | 11.3647 | 9.3568 | 9.0679 | 9.0324 | 8.5227 | 9.2097 | 9.3738 | 7.0896 | 0.0126 | 0.8772 | 2.2399 |
| hsa-miR-26a-5p | 12.8777 | 11.9688 | 14.068 | 12.3647 | 8.7032 | 8.1338 | 8.7302 | 10.4708 | 9.8762 | 10.8797 | 8.3866 | 0.0342 | 0.8772 | 2.421 |
| hsa-miR-125b-5p | 14.9954 | 14.1832 | 15.9825 | 16.3726 | 12.1744 | 9.2213 | 9.3011 | 13.618 | 12.9622 | 12.8524 | 9.9827 | 0.0276 | 0.8772 | 2.4859 |
| hsa-miR-4516 | 13.8159 | 12.5298 | 12.4005 | 11.4026 | 10.9723 | 10.1845 | 10.3383 | 10.764 | 9.2489 | 9.7449 | 7.9145 | 0.0042 | 0.8772 | 2.525 |
| hsa-miR-142-3p | 13.4362 | 13.2038 | 15.1302 | 11.9187 | 10.17 | 9.4863 | 9.2434 | 11.084 | 10.969 | 11.2165 | 8.8183 | 0.0296 | 0.8772 | 2.6355 |
| hsa-miR-126-3p | 15.4053 | 14.1322 | 15.6413 | 13.9869 | 10.7233 | 9.7273 | 11.1205 | 12.1616 | 12.509 | 12.9313 | 9.2457 | 0.0385 | 0.8772 | 2.6953 |
| hsa-miR-199a-3p + hsa-miR-199b-3p | 12.9875 | 12.2714 | 13.9925 | 13.4817 | 9.6284 | 8.4762 | 9.0881 | 10.7674 | 10.6847 | 11.0817 | 8.4839 | 0.0206 | 0.8772 | 2.7086 |
| hsa-miR-150-5p | 14.1036 | 12.1965 | 14.3038 | 12.2777 | 10.4418 | 8.6303 | 10.5113 | 11.2376 | 9.7177 | 10.6764 | 7.9827 | 0.012 | 0.8772 | 2.8721 |
| hsa-miR-494 | 16.5685 | 16.7831 | 15.8968 | 13.7468 | 11.2664 | 12.4775 | 13.4775 | 16.1657 | 10.9051 | 10.2111 | 8.11 | 0.0884 | 0.8912 | 2.9599 |
| hsa-miR-145-5p | 14.0336 | 12.8331 | 16.0434 | 16.7293 | 12.3282 | 8.2334 | 11.3835 | 11.3256 | 10.8845 | 11.0338 | 7.9603 | 0.0046 | 0.8772 | 4.2567 |
| hsa-miR-1246 | 13.0431 | 14.0539 | 12.4552 | 2.8094 | 2.2265 | 2.3277 | 2.0426 | 10.8257 | 2.441 | 3.1457 | 1.9598 | 0.1347 | 0.9258 | 5.1272 |
| hsa-miR-143-3p | 14.2575 | 14.2683 | 16.7873 | 15.9869 | 11.4321 | 2.3277 | 9.5113 | 11.0706 | 12.7522 | 11.6725 | 5.5454 | 0.0172 | 0.8772 | 5.7331 |

*progress vs non-progress

TABLE 2

| mirna | s01 | s02 | s03 | s04 | s05 | s06 | s07 | s08 | s09 | s10 | s11 | P-value (t-test) | Q-value (FDR) | log2 fold change* |
|---|---|---|---|---|---|---|---|---|---|---|---|---|---|---|
| hsa-miR-143-3p | 14.2575 | 14.2683 | 16.7873 | 15.9869 | 11.4321 | 2.3277 | 9.5113 | 11.0706 | 12.7522 | 11.6725 | 5.5454 | 0.0172 | 0.8772 | 5.7331 |
| hsa-miR-145-5p | 14.0336 | 12.8331 | 16.0434 | 16.7293 | 12.3282 | 8.2334 | 11.3835 | 11.3256 | 10.8845 | 11.0338 | 7.9603 | 0.0046 | 0.8772 | 4.2567 |
| hsa-miR-150-5p | 14.1036 | 12.1965 | 14.3038 | 12.2777 | 10.4418 | 8.6303 | 10.5113 | 11.2376 | 9.7177 | 10.6764 | 7.9827 | 0.012 | 0.8772 | 2.8721 |
| hsa-miR-199a-3p + hsa-miR-199b-3p | 12.9875 | 12.2714 | 13.9925 | 13.4817 | 9.6284 | 8.4762 | 9.0881 | 10.7674 | 10.6847 | 11.0817 | 8.4839 | 0.0206 | 0.8772 | 2.7086 |
| hsa-miR-126-3p | 15.4053 | 14.1322 | 15.6413 | 13.9869 | 10.7233 | 9.7273 | 11.1205 | 12.1616 | 12.509 | 12.9313 | 9.2457 | 0.0385 | 0.8772 | 2.6953 |
| hsa-miR-142-3p | 13.4362 | 13.2038 | 15.1302 | 11.9187 | 10.17 | 9.4863 | 9.2434 | 11.084 | 10.969 | 11.2165 | 8.8183 | 0.0296 | 0.8772 | 2.6355 |
| hsa-miR-4516 | 13.8159 | 12.5298 | 12.4005 | 11.4026 | 10.9723 | 10.1845 | 10.3383 | 10.764 | 9.2489 | 9.7449 | 7.9145 | 0.0042 | 0.8772 | 2.525 |
| hsa-miR-125b-5p | 14.9954 | 14.1832 | 15.9825 | 16.3726 | 12.1744 | 11.8422 | 12.2773 | 13.618 | 12.9622 | 12.8524 | 9.9827 | 0.0276 | 0.8772 | 2.4859 |
| hsa-miR-26a-5p | 12.8777 | 11.9688 | 14.068 | 12.3647 | 9.2719 | 9.2213 | 9.3011 | 10.4708 | 9.8762 | 10.8797 | 8.3866 | 0.0342 | 0.8772 | 2.421 |
| hsa-let-7e-5p | 10.9962 | 10.5835 | 12.1017 | 11.3647 | 8.7032 | 8.1338 | 8.7302 | 8.5227 | 9.2097 | 9.3738 | 7.0896 | 0.0126 | 0.8772 | 2.2399 |
| hsa-miR-26b-5p | 12.924 | 11.9038 | 14.1215 | 11.8353 | 9.3568 | 9.0679 | 9.0324 | 10.7305 | 10.6065 | 10.8524 | 8.4681 | 0.0451 | 0.8772 | 2.2353 |
| hsa-miR-130a-3p | 11.5652 | 10.7114 | 12.5037 | 11.9471 | 8.8274 | 8.4762 | 8.851 | 9.8572 | 9.8252 | 9.2535 | 7.0478 | 0.0227 | 0.8772 | 2.2258 |
| hsa-miR-199b-5p | 10.8976 | 9.9595 | 12.4711 | 11.9901 | 8.315 | 7.8811 | 7.9506 | 8.7271 | 9.4188 | 9.6842 | 7.4838 | 0.0384 | 0.8772 | 2.2024 |
| hsa-miR-100-5p | 11.6748 | 11.0116 | 12.6014 | 12.4684 | 8.751 | 8.0544 | 9.0437 | 9.2846 | 10.7814 | 9.8032 | 7.8911 | 0.0352 | 0.8772 | 2.1584 |
| hsa-miR-29b-3p | 15.0008 | 14.403 | 16.1465 | 14.1633 | 11.9622 | 11.2453 | 10.9171 | 13.2823 | 13.5224 | 13.5744 | 11.0688 | 0.0448 | 0.8772 | 2.0667 |
| hsa-miR-30a-5p | 11.7538 | 11.3462 | 12.7578 | 11.5036 | 9.0088 | 8.3488 | 8.4866 | 9.3301 | 11.3986 | 10.1108 | 7.8911 | 0.0376 | 0.8772 | 2.013 |
| hsa-miR-30b-5p | 12.5898 | 11.8908 | 13.8715 | 12.4594 | 9.9348 | 9.9847 | 9.1832 | 10.8225 | 10.529 | 11.7149 | 9.16 | 0.0397 | 0.8772 | 1.9169 |
| hsa-miR-199a-5p | 10.6721 | 9.6235 | 11.8357 | 11.2737 | 8.5494 | 7.684 | 8.3656 | 8.8065 | 8.9961 | 9.4118 | 7.7932 | 0.029 | 0.8772 | 1.8813 |
| hsa-miR-223-3p | 11.8456 | 10.7298 | 12.2729 | 11.7409 | 9.9486 | 8.5553 | 8.7302 | 9.7871 | 10.5553 | 10.3642 | 8.7677 | 0.01 | 0.8772 | 1.8476 |
| hsa-miR-342-3p | 12.1364 | 10.9054 | 13.046 | 12.8422 | 10.4124 | 9.7359 | 9.992 | 10.6857 | 10.2229 | 10.6449 | 8.9827 | 0.0207 | 0.8772 | 1.8245 |
| hsa-miR-361-5p | 10.4994 | 9.8826 | 11.6953 | 10.5783 | 8.5313 | 8.2807 | 8.2136 | 9.1489 | 8.8339 | 9.3149 | 7.3179 | 0.0256 | 0.8772 | 1.7191 |
| hsa-miR-1915-3p | 10.7666 | 10.0444 | 10.4981 | 9.729 | 8.7194 | 8.2334 | 8.5355 | 8.9992 | 8.529 | 7.8455 | 7.3179 | 0.005 | 0.8772 | 1.7081 |
| hsa-miR-497-5p | 9.2462 | 8.7371 | 10.5534 | 9.039 | 7.3568 | 6.85 | 6.6286 | 7.4911 | 8.2229 | 8.315 | 6.5452 | 0.0302 | 0.8772 | 1.6444 |
| hsa-miR-34a-5p | 11.456 | 11.0936 | 12.0334 | 12.2025 | 9.1223 | 9.2807 | 8.8892 | 10.5149 | 10.3604 | 10.2111 | 7.9827 | 0.0448 | 0.8772 | 1.6417 |
| hsa-miR-125a-5p | 10.7564 | 9.7731 | 11.6066 | 12.0955 | 9.6025 | 8.4964 | 9.3383 | 9.7065 | 10.2489 | 9.8174 | 7.5149 | 0.0379 | 0.8772 | 1.5798 |
| hsa-miR-195-5p | 10.4872 | 9.5835 | 11.6402 | 10.8045 | 8.315 | 8.3488 | 8.4187 | 8.6857 | 9.0563 | 9.3149 | 7.8672 | 0.0497 | 0.8772 | 1.5508 |
| hsa-miR-374b-5p | 10.5593 | 10.3172 | 11.8087 | 10.3258 | 8.6537 | 8.4139 | 8.436 | 9.0544 | 9.5396 | 9.8455 | 8.0264 | 0.0438 | 0.8772 | 1.447 |
| hsa-miR-376a-3p | 10.1482 | 10.0793 | 10.6428 | 10.6928 | 8.4943 | 8.2572 | 8.6584 | 8.8447 | 9.3484 | 9.2948 | 8.1891 | 0.0318 | 0.8772 | 1.246 |
| hsa-miR-423-5p | 9.9297 | 9.8826 | 11.0295 | 9.6681 | 8.6025 | 8.1844 | 8.4012 | 8.0215 | 9.0265 | 9.8315 | 8.0047 | 0.034 | 0.8772 | 1.2442 |
| hsa-miR-720 | 16.9648 | 16.4432 | 17.309 | 17.1436 | 16.5724 | 17.0344 | 16.4224 | 15.5944 | 14.8499 | 16.1911 | 13.7825 | 0.0495 | 0.8772 | 1.2408 |
| hsa-miR-132-3p | 10.0262 | 9.0266 | 9.5315 | 10.3724 | 8.4173 | 7.9115 | 8.0437 | 8.303 | 8.6704 | 9.0519 | 7.6882 | 0.0227 | 0.8772 | 1.1967 |
| hsa-miR-4508 | 11.4592 | 11.1549 | 11.1383 | 9.6303 | 9.4659 | 9.4139 | 9.6361 | 9.4749 | 9.5708 | 9.6045 | 8.7932 | 0.0497 | 0.8772 | 1.1541 |
| hsa-miR-3195 | 9.3173 | 8.5507 | 9.3054 | 7.9394 | 7.9824 | 7.6118 | 7.2136 | 7.3211 | 7.901 | 8.2325 | 6.6042 | 0.0177 | 0.8772 | 1.1383 |

*progress vs non-progress

What is claimed is:

1. A method for treating a subject diagnosed with Barrett's esophagus but not dysplasia or carcinoma, comprising
   a) determining elevated expression levels of miRNA in a biological sample from a subject diagnosed with Barrett's esophagus but not dysplasia or carcinoma, as compared to the expression levels in a control sample, wherein the miRNA comprises hsa-miR-720, hsa-miR-143-3p, and hsa-miR-4508; and
   b) treating the subject with surgery, laser treatment, radiofrequency ablation, chemotherapy, or any combination thereof.

2. The method of claim 1, further comprising calculating a risk score from the miRNA expression levels.

3. The method of claim 1, wherein the biological sample is RNA derived from formalin fixed paraffin embedded tissue.

4. The method of claim 1, wherein the miRNA further comprises hsa-miR-145-5p, hsa-miR-150-5p, hsa-miR-199a-3p+/hsa-miR-199b-3p, hsa-miR-126-3p, has-miR-142-3p, hsa-miR-4516, hsa-miR-125b-5p, hsa-miR-26a-5p, hsa-let-7e-5p, hsa-miR-26b-5p, hsa-miR-130a-3p, hsa-miR-199b-5p, hsa-miR-100-5p, hsa-miR-29b-3p, hsa-miR-30a-5p, hsa-miR-30b-5p, hsa-miR-199a-5p, hsa-miR-223-3p, hsa-miR-342-3p, hsa-miR-361-5p, hsa-miR-1915-3p, hsa-miR-497-5p, hsa-miR-34a-5p, hsa-miR-125a-5p, hsa-miR-195-5p, hsa-miR-374b-5p, hsa-miR-376a-3p, hsa-miR-423-5p, hsa-niR-132-3p, and hsa-miR-3195, and wherein the expression levels are determined using a nanoreporter code system.

* * * * *